(12) United States Patent
Sinha et al.

(10) Patent No.: US 10,732,600 B2
(45) Date of Patent: *Aug. 4, 2020

(54) MULTI-FUNCTION THERMOSTAT WITH HEALTH MONITORING FEATURES

(71) Applicant: Johnson Controls Technology Company, Auburn Hills, MI (US)

(72) Inventors: Sudhi Sinha, Milwaukee, WI (US); Joseph R. Ribbich, Waukesha, WI (US); Michael L. Ribbich, Oconomowoc, WI (US); Charles J. Gaidish, South Milwaukee, WI (US); John P. Cipolla, Inverness, IL (US)

(73) Assignee: Johnson Controls Technology Company, Auburn Hills, MI (US)

(*) Notice: Subject to any disclaimer, the term of this patent is extended or adjusted under 35 U.S.C. 154(b) by 0 days.

This patent is subject to a terminal disclaimer.

(21) Appl. No.: 16/450,027

(22) Filed: Jun. 24, 2019

(65) Prior Publication Data

US 2019/0310598 A1 Oct. 10, 2019

Related U.S. Application Data

(63) Continuation of application No. 15/336,789, filed on Oct. 28, 2016, now Pat. No. 10,345,781.
(Continued)

(51) Int. Cl.
*G08C 19/22* (2006.01)
*H04Q 9/00* (2006.01)
(Continued)

(52) U.S. Cl.
CPC ........ *G05B 19/048* (2013.01); *A61B 5/02055* (2013.01); *A61B 5/681* (2013.01);
(Continued)

(58) Field of Classification Search
CPC ...... G08B 21/10; G08B 7/062; G08B 25/005; G08B 21/0453; H05B 37/0218;
(Continued)

(56) References Cited

U.S. PATENT DOCUMENTS 4,107,464 A 8/1978 Lynch et al.
4,942,613 A 7/1990 Lynch
(Continued)

FOREIGN PATENT DOCUMENTS

CA 2466854 C 4/2008
CA 2633200 C 1/2011
(Continued)

OTHER PUBLICATIONS

U.S. Appl. No. 14/543,354, filed Nov. 17, 2014, Vivint, Inc.
(Continued)

*Primary Examiner* — Tanmay K Shah
(74) *Attorney, Agent, or Firm* — Foley & Lardner LLP

(57) ABSTRACT

A multi-function thermostat for a building includes a sensor configured to measure an environmental condition of a building space, a communication interface, and a processing circuit. The communications interface is configured to communicate with an emergency server and receive occupant health data from a health sensor configured to monitor an occupant. The processing circuit is configured to determine a health metric associated with the occupant based on the occupant health data and cause the communications interface to send a distress message to the emergency server when the health metric associated with the occupant indicates a medical emergency.

20 Claims, 37 Drawing Sheets

Related U.S. Application Data

(60) Provisional application No. 62/247,672, filed on Oct. 28, 2015, provisional application No. 62/274,750, filed on Jan. 4, 2016, provisional application No. 62/275,202, filed on Jan. 5, 2016, provisional application No. 62/275,204, filed on Jan. 5, 2016, provisional application No. 62/275,199, filed on Jan. 5, 2016, provisional application No. 62/275,711, filed on Jan. 6, 2016.

(51) Int. Cl.

| | | |
|---|---|---|
| *G05B 19/048* | (2006.01) | |
| *F24F 11/30* | (2018.01) | |
| *F24F 11/62* | (2018.01) | |
| *G08B 7/06* | (2006.01) | |
| *G06Q 20/38* | (2012.01) | |
| *H04W 64/00* | (2009.01) | |
| *A61B 5/0205* | (2006.01) | |
| *A61B 5/00* | (2006.01) | |
| *A61M 5/172* | (2006.01) | |
| *G08B 21/04* | (2006.01) | |
| *H04L 29/08* | (2006.01) | |
| *G06F 3/16* | (2006.01) | |
| *G06Q 20/10* | (2012.01) | |
| *G06Q 20/40* | (2012.01) | |
| *G06Q 50/12* | (2012.01) | |
| *G06Q 50/30* | (2012.01) | |
| *G07F 17/00* | (2006.01) | |
| *G07G 5/00* | (2006.01) | |
| *G06F 16/2457* | (2019.01) | |
| *A61M 5/14* | (2006.01) | |
| *F24F 110/10* | (2018.01) | |
| *F24F 120/10* | (2018.01) | |
| *F24F 120/12* | (2018.01) | |
| *F24F 120/14* | (2018.01) | |
| *F24F 120/20* | (2018.01) | |
| *F24F 11/63* | (2018.01) | |
| *F24F 11/52* | (2018.01) | |
| *G08B 19/00* | (2006.01) | |
| *G08B 27/00* | (2006.01) | |
| *A61B 5/11* | (2006.01) | |
| *A61B 5/117* | (2016.01) | |
| *H05B 47/11* | (2020.01) | |
| *H05B 47/105* | (2020.01) | |
| *A61B 5/024* | (2006.01) | |
| *G06F 3/0488* | (2013.01) | |

(52) U.S. Cl.
CPC .......... *A61M 5/1723* (2013.01); *F24F 11/30* (2018.01); *F24F 11/62* (2018.01); *G06F 3/167* (2013.01); *G06Q 20/10* (2013.01); *G06Q 20/382* (2013.01); *G06Q 20/383* (2013.01); *G06Q 20/405* (2013.01); *G06Q 50/12* (2013.01); *G06Q 50/30* (2013.01); *G07F 17/0057* (2013.01); *G07G 5/00* (2013.01); *G08B 7/066* (2013.01); *G08B 21/0453* (2013.01); *H04L 67/12* (2013.01); *H04W 64/003* (2013.01); *A61B 5/02405* (2013.01); *A61B 5/02438* (2013.01); *A61B 5/117* (2013.01); *A61B 5/1113* (2013.01); *A61M 5/14* (2013.01); *A61M 2209/088* (2013.01); *F24F 11/52* (2018.01); *F24F 11/63* (2018.01); *F24F 2110/10* (2018.01); *F24F 2120/10* (2018.01); *F24F 2120/12* (2018.01); *F24F 2120/14* (2018.01); *F24F 2120/20* (2018.01); *G05B 2219/15117* (2013.01); *G05B 2219/2614* (2013.01); *G05B 2219/2642* (2013.01); *G06F 3/04883* (2013.01); *G06F 16/24575* (2019.01); *G08B 19/00* (2013.01); *G08B 27/00* (2013.01); *H04W 64/00* (2013.01); *H05B 47/105* (2020.01); *H05B 47/11* (2020.01)

(58) Field of Classification Search
CPC . H04W 64/003; G07F 17/0057; G06Q 20/10; G06Q 20/405; G06Q 50/12; G06Q 50/30; F24F 11/006; F24F 11/0012; F24F 2011/0057; F24F 2011/0035; F24F 2011/0061; F24F 2011/0036; F24F 2011/0091; F24F 11/0086; F24F 11/0034; H04L 67/12; G07G 5/00; G06F 3/167; G06F 3/04883; G06F 17/30528; A61M 2209/088; A61M 5/1723; G05B 2219/15117; G05B 2219/2642; G05B 2219/2614; G05B 19/048; A61B 5/02055; A61B 5/681; A61B 5/02405; A61B 5/02438
USPC ...................................................... 340/407.1
See application file for complete search history.

(56) References Cited

U.S. PATENT DOCUMENTS

| | | |
|---|---|---|
| 5,052,186 A | 10/1991 | Dudley et al. |
| 5,062,276 A | 11/1991 | Dudley |
| 5,797,729 A | 8/1998 | Rafuse et al. |
| 6,121,885 A | 9/2000 | Masone et al. |
| 6,164,374 A | 12/2000 | Rhodes et al. |
| 6,169,937 B1 | 1/2001 | Peterson |
| 6,227,961 B1 | 5/2001 | Moore et al. |
| 6,260,765 B1 | 7/2001 | Natale et al. |
| 6,314,750 B1 | 11/2001 | Ishikawa et al. |
| 6,351,693 B1 | 2/2002 | Monie et al. |
| 6,435,418 B1 | 8/2002 | Toth et al. |
| 6,487,869 B1 | 12/2002 | Sulc et al. |
| 6,557,771 B2 | 5/2003 | Shah |
| 6,641,054 B2 | 11/2003 | Morey |
| 6,726,112 B1 | 4/2004 | Ho |
| 6,726,113 B2 | 4/2004 | Guo |
| 6,810,307 B1 | 10/2004 | Addy |
| 6,824,069 B2 | 11/2004 | Rosen |
| 6,851,621 B1 | 2/2005 | Wacker et al. |
| 6,874,691 B1 | 4/2005 | Hildebrand et al. |
| 6,888,441 B2 | 5/2005 | Carey |
| 6,995,518 B2 | 2/2006 | Havlik et al. |
| 7,028,912 B1 | 4/2006 | Rosen |
| 7,083,109 B2 | 8/2006 | Pouchak |
| 7,099,748 B2 | 8/2006 | Rayburn |
| 7,140,551 B2 | 11/2006 | De Pauw et al. |
| 7,146,253 B2 | 12/2006 | Hoog et al. |
| 7,152,806 B1 | 12/2006 | Rosen |
| 7,156,317 B1 | 1/2007 | Moore |
| 7,156,318 B1 | 1/2007 | Rosen |
| 7,159,789 B2 | 1/2007 | Schwendinger et al. |
| 7,159,790 B2 | 1/2007 | Schwendinger et al. |
| 7,167,079 B2 | 1/2007 | Smyth et al. |
| 7,188,002 B2 | 3/2007 | Chapman et al. |
| 7,212,887 B2 | 5/2007 | Shah et al. |
| 7,225,054 B2 | 5/2007 | Amundson et al. |
| 7,232,075 B1 | 6/2007 | Rosen |
| 7,261,243 B2 | 8/2007 | Butler et al. |
| 7,274,972 B2 | 9/2007 | Amundson et al. |
| 7,287,709 B2 | 10/2007 | Proffitt et al. |
| 7,296,426 B2 | 11/2007 | Butler et al. |
| 7,299,996 B2 | 11/2007 | Garrett et al. |
| 7,306,165 B2 | 12/2007 | Shah |
| 7,308,384 B2 | 12/2007 | Shah et al. |
| 7,317,970 B2 | 1/2008 | Pienta et al. |
| 7,331,187 B2 | 2/2008 | Kates |
| 7,343,751 B2 | 3/2008 | Kates |
| 7,383,158 B2 | 6/2008 | Krocker et al. |

(56) References Cited

U.S. PATENT DOCUMENTS

| | | |
|---|---|---|
| 7,402,780 B2 | 7/2008 | Mueller et al. |
| 7,434,744 B2 | 10/2008 | Garozzo et al. |
| 7,442,012 B2 | 10/2008 | Moens |
| 7,469,550 B2 | 12/2008 | Chapman et al. |
| 7,475,558 B2 | 1/2009 | Perry |
| 7,475,828 B2 | 1/2009 | Bartlett et al. |
| 7,556,207 B2 | 7/2009 | Mueller et al. |
| 7,565,813 B2 | 7/2009 | Pouchak |
| 7,575,179 B2 | 8/2009 | Morrow et al. |
| 7,584,897 B2 | 9/2009 | Schultz et al. |
| 7,614,567 B2 | 11/2009 | Chapman et al. |
| 7,624,931 B2 | 12/2009 | Chapman et al. |
| 7,633,743 B2 | 12/2009 | Barton et al. |
| 7,636,604 B2 | 12/2009 | Bergman et al. |
| 7,638,739 B2 | 12/2009 | Rhodes et al. |
| 7,641,126 B2 | 1/2010 | Schultz et al. |
| 7,645,158 B2 | 1/2010 | Mulhouse et al. |
| 7,667,163 B2 | 2/2010 | Ashworth et al. |
| 7,726,581 B2 | 6/2010 | Naujok et al. |
| 7,731,096 B2 | 6/2010 | Lorenz et al. |
| 7,731,098 B2 | 6/2010 | Butler et al. |
| 7,740,184 B2 | 6/2010 | Schnell et al. |
| 7,748,225 B2 | 7/2010 | Butler et al. |
| 7,748,639 B2 | 7/2010 | Perry |
| 7,748,640 B2 | 7/2010 | Roher et al. |
| 7,755,220 B2 | 7/2010 | Sorg et al. |
| 7,765,826 B2 | 8/2010 | Nichols |
| 7,774,102 B2 | 8/2010 | Butler et al. |
| 7,775,452 B2 | 8/2010 | Shah et al. |
| 7,784,291 B2 | 8/2010 | Butler et al. |
| 7,784,704 B2 | 8/2010 | Harter |
| 7,802,618 B2 | 9/2010 | Simon et al. |
| 7,832,221 B2 | 11/2010 | Wijaya et al. |
| 7,832,652 B2 | 11/2010 | Barton et al. |
| 7,845,576 B2 | 12/2010 | Siddaramanna et al. |
| 7,861,941 B2 | 1/2011 | Schultz et al. |
| 7,867,646 B2 | 1/2011 | Rhodes |
| 7,908,116 B2 | 3/2011 | Steinberg et al. |
| 7,908,117 B2 | 3/2011 | Steinberg et al. |
| 7,918,406 B2 | 4/2011 | Rosen |
| 7,938,336 B2 | 5/2011 | Rhodes et al. |
| 7,941,294 B2 | 5/2011 | Shahi et al. |
| 7,954,726 B2 | 6/2011 | Siddaramanna et al. |
| 7,963,454 B2 | 6/2011 | Sullivan et al. |
| 7,979,164 B2 | 7/2011 | Garozzo et al. |
| 7,992,794 B2 | 8/2011 | Leen et al. |
| 8,010,237 B2 | 8/2011 | Cheung et al. |
| 8,032,254 B2 | 10/2011 | Amundson et al. |
| 8,078,326 B2 | 12/2011 | Harrod et al. |
| 8,082,065 B2 | 12/2011 | Imes et al. |
| 8,083,154 B2 | 12/2011 | Schultz et al. |
| 8,089,032 B2 | 1/2012 | Beland et al. |
| 8,091,794 B2 | 1/2012 | Siddaramanna et al. |
| 8,099,195 B2 | 1/2012 | Imes et al. |
| 8,108,076 B2 | 1/2012 | Imes et al. |
| 8,131,506 B2 | 3/2012 | Steinberg et al. |
| 8,141,791 B2 | 3/2012 | Rosen |
| 8,167,216 B2 | 5/2012 | Schultz et al. |
| 8,180,492 B2 | 5/2012 | Steinberg |
| 8,190,296 B2 | 5/2012 | Alhilo |
| 8,195,313 B1 | 6/2012 | Fadell et al. |
| 8,196,185 B2 | 6/2012 | Geadelmann et al. |
| 8,209,059 B2 | 6/2012 | Stockton |
| 8,239,066 B2 | 8/2012 | Jennings et al. |
| 8,276,829 B2 | 10/2012 | Stoner et al. |
| 8,280,536 B1 | 10/2012 | Fadell et al. |
| 8,289,182 B2 | 10/2012 | Vogel et al. |
| 8,289,226 B2 | 10/2012 | Takach et al. |
| 8,299,919 B2 | 10/2012 | Dayton et al. |
| 8,321,058 B2 | 11/2012 | Zhou et al. |
| 8,346,396 B2 | 1/2013 | Amundson et al. |
| 8,387,891 B1 | 3/2013 | Simon et al. |
| 8,393,550 B2 | 3/2013 | Simon et al. |
| 8,412,488 B2 | 4/2013 | Steinberg et al. |
| 8,429,566 B2 | 4/2013 | Koushik et al. |
| 8,456,293 B1 | 6/2013 | Trundle et al. |
| 8,473,109 B1 | 6/2013 | Imes et al. |
| 8,476,964 B1 | 7/2013 | Atri |
| 8,489,243 B2 | 7/2013 | Fadell et al. |
| 8,504,180 B2 | 8/2013 | Imes et al. |
| 8,510,255 B2 | 8/2013 | Fadell et al. |
| 8,511,576 B2 | 8/2013 | Warren et al. |
| 8,511,577 B2 | 8/2013 | Warren et al. |
| 8,517,088 B2 | 8/2013 | Moore et al. |
| 8,523,083 B2 | 9/2013 | Warren et al. |
| 8,523,084 B2 | 9/2013 | Siddaramanna et al. |
| 8,527,096 B2 | 9/2013 | Pavlak et al. |
| 8,532,827 B2 | 9/2013 | Stefanski et al. |
| 8,544,285 B2 | 10/2013 | Stefanski et al. |
| 8,549,658 B2 | 10/2013 | Kolavennu et al. |
| 8,550,368 B2 | 10/2013 | Butler et al. |
| 8,554,374 B2 | 10/2013 | Lunacek et al. |
| 8,555,662 B2 | 10/2013 | Peterson et al. |
| 8,558,179 B2 | 10/2013 | Filson et al. |
| 8,560,127 B2 | 10/2013 | Leen et al. |
| 8,560,128 B2 | 10/2013 | Ruff et al. |
| 8,571,518 B2 | 10/2013 | Imes et al. |
| 8,596,550 B2 | 12/2013 | Steinberg et al. |
| 8,600,564 B2 | 12/2013 | Imes et al. |
| 8,606,409 B2 | 12/2013 | Amundson et al. |
| 8,613,792 B2 | 12/2013 | Ragland et al. |
| 8,620,841 B1 | 12/2013 | Filson et al. |
| 8,622,314 B2 | 1/2014 | Fisher et al. |
| 8,626,344 B2 | 1/2014 | Imes et al. |
| 8,630,741 B1 | 1/2014 | Matsuoka et al. |
| 8,630,742 B1 | 1/2014 | Stefanski et al. |
| 8,644,009 B2 | 2/2014 | Rylski et al. |
| 8,659,302 B1 | 2/2014 | Warren et al. |
| 8,671,702 B1 | 3/2014 | Shotey et al. |
| 8,674,816 B2 | 3/2014 | Trundle et al. |
| 8,689,572 B2 | 4/2014 | Evans et al. |
| 8,695,887 B2 | 4/2014 | Helt et al. |
| 8,706,270 B2 | 4/2014 | Fadell et al. |
| 8,708,242 B2 | 4/2014 | Conner et al. |
| 8,712,590 B2 | 4/2014 | Steinberg |
| 8,718,826 B2 | 5/2014 | Ramachandran et al. |
| 8,726,680 B2 | 5/2014 | Schenk et al. |
| 8,727,611 B2 | 5/2014 | Huppi et al. |
| 8,738,327 B2 | 5/2014 | Steinberg et al. |
| 8,746,583 B2 | 6/2014 | Simon et al. |
| 8,752,771 B2 | 6/2014 | Warren et al. |
| 8,754,780 B2 | 6/2014 | Petite et al. |
| 8,766,194 B2 | 7/2014 | Filson et al. |
| 8,770,490 B2 | 7/2014 | Drew |
| 8,770,491 B2 | 7/2014 | Warren et al. |
| 8,788,103 B2 | 7/2014 | Warren et al. |
| 8,802,981 B2 | 8/2014 | Wallaert et al. |
| 8,830,267 B2 | 9/2014 | Brackney |
| 8,838,282 B1 | 9/2014 | Ratliff et al. |
| 8,843,239 B2 | 9/2014 | Mighdoll et al. |
| 8,850,348 B2 | 9/2014 | Fadell et al. |
| 8,855,830 B2 | 10/2014 | Imes et al. |
| 8,868,219 B2 | 10/2014 | Fadell et al. |
| 8,870,086 B2 | 10/2014 | Tessier et al. |
| 8,870,087 B2 | 10/2014 | Pienta et al. |
| 8,880,047 B2 | 11/2014 | Konicek et al. |
| 8,893,032 B2 | 11/2014 | Bruck et al. |
| 8,903,552 B2 | 12/2014 | Amundson et al. |
| 8,918,219 B2 | 12/2014 | Sloo et al. |
| 8,942,853 B2 | 1/2015 | Stefanski et al. |
| 8,944,338 B2 | 2/2015 | Warren et al. |
| 8,950,686 B2 | 2/2015 | Matsuoka et al. |
| 8,950,687 B2 | 2/2015 | Bergman et al. |
| 8,961,005 B2 | 2/2015 | Huppi et al. |
| 8,978,994 B2 | 3/2015 | Moore et al. |
| 8,998,102 B2 | 4/2015 | Fadell et al. |
| 9,014,686 B2 | 4/2015 | Ramachandran et al. |
| 9,014,860 B2 | 4/2015 | Moore et al. |
| 9,020,647 B2 | 4/2015 | Johnson et al. |
| 9,026,232 B2 | 5/2015 | Fadell et al. |
| 9,033,255 B2 | 5/2015 | Tessier et al. |
| RE45,574 E | 6/2015 | Harter |
| 9,074,784 B2 | 7/2015 | Sullivan et al. |
| 9,075,419 B2 | 7/2015 | Sloo et al. |

(56) References Cited

U.S. PATENT DOCUMENTS

| | | |
|---|---|---|
| 9,077,055 B2 | 7/2015 | Yau |
| 9,080,782 B1 | 7/2015 | Sheikh |
| 9,081,393 B2 | 7/2015 | Lunacek et al. |
| 9,086,703 B2 | 7/2015 | Warren et al. |
| 9,088,306 B1 | 7/2015 | Ramachandran et al. |
| 9,092,039 B2 | 7/2015 | Fadell et al. |
| 9,098,279 B2 | 8/2015 | Mucignat et al. |
| 9,116,529 B2 | 8/2015 | Warren et al. |
| 9,121,623 B2 | 9/2015 | Filson et al. |
| 9,122,283 B2 | 9/2015 | Rylski et al. |
| 9,125,049 B2 | 9/2015 | Huang et al. |
| 9,127,853 B2 | 9/2015 | Filson et al. |
| 9,134,710 B2 | 9/2015 | Cheung et al. |
| 9,134,715 B2 | 9/2015 | Geadelmann et al. |
| 9,146,041 B2 | 9/2015 | Novotny et al. |
| 9,151,510 B2 | 10/2015 | Leen |
| 9,154,001 B2 | 10/2015 | Dharwada et al. |
| 9,157,764 B2 | 10/2015 | Shetty et al. |
| 9,164,524 B2 | 10/2015 | Imes et al. |
| 9,175,868 B2 | 11/2015 | Fadell et al. |
| 9,175,871 B2 | 11/2015 | Gourlay et al. |
| 9,182,141 B2 | 11/2015 | Sullivan et al. |
| 9,189,751 B2 | 11/2015 | Matsuoka et al. |
| 9,191,277 B2 | 11/2015 | Rezvani et al. |
| 9,191,909 B2 | 11/2015 | Rezvani et al. |
| 9,194,597 B2 | 11/2015 | Steinberg et al. |
| 9,194,598 B2 | 11/2015 | Fadell et al. |
| 9,194,600 B2 | 11/2015 | Kates |
| 9,207,817 B2 | 12/2015 | Tu |
| 9,213,342 B2 | 12/2015 | Drake et al. |
| 9,215,281 B2 | 12/2015 | Iggulden et al. |
| 9,222,693 B2 | 12/2015 | Gourlay et al. |
| 9,223,323 B2 | 12/2015 | Matas et al. |
| 9,234,669 B2 | 1/2016 | Filson et al. |
| 9,244,445 B2 | 1/2016 | Finch et al. |
| 9,244,470 B2 | 1/2016 | Steinberg |
| 9,261,287 B2 | 2/2016 | Warren et al. |
| 9,268,344 B2 | 2/2016 | Warren et al. |
| 9,279,595 B2 | 3/2016 | Mighdoll et al. |
| 9,282,590 B2 | 3/2016 | Donlan |
| 9,285,134 B2 | 3/2016 | Bray et al. |
| 9,285,802 B2 | 3/2016 | Arensmeier |
| 9,286,781 B2 | 3/2016 | Filson et al. |
| 9,291,359 B2 | 3/2016 | Fadell et al. |
| 9,292,022 B2 | 3/2016 | Ramachandran et al. |
| 9,298,196 B2 | 3/2016 | Matsuoka et al. |
| 9,298,197 B2 | 3/2016 | Matsuoka et al. |
| D763,707 S | 8/2016 | Sinha et al. |
| D790,369 S | 6/2017 | Sinha et al. |
| 2001/0015281 A1 | 8/2001 | Schiedegger et al. |
| 2003/0034897 A1 | 2/2003 | Shamoon et al. |
| 2003/0034898 A1 | 2/2003 | Shamoon et al. |
| 2003/0136853 A1 | 7/2003 | Morey |
| 2003/0177012 A1 | 9/2003 | Drennan |
| 2004/0074978 A1 | 4/2004 | Rosen |
| 2004/0125940 A1 | 7/2004 | Turcan et al. |
| 2004/0249479 A1 | 12/2004 | Shorrock |
| 2004/0262410 A1 | 12/2004 | Hull |
| 2005/0040943 A1 | 2/2005 | Winick |
| 2005/0083168 A1 | 4/2005 | Breitenbach |
| 2005/0119794 A1 | 6/2005 | Amundson et al. |
| 2005/0156049 A1 | 7/2005 | Van Ostrand et al. |
| 2005/0194456 A1 | 9/2005 | Tessier et al. |
| 2005/0195757 A1 | 9/2005 | Kidder et al. |
| 2005/0270151 A1 | 12/2005 | Winick |
| 2005/0270735 A1 | 12/2005 | Chen |
| 2006/0038025 A1 | 2/2006 | Lee |
| 2006/0113398 A1 | 6/2006 | Ashworth |
| 2006/0192022 A1 | 8/2006 | Barton et al. |
| 2006/0226970 A1 | 10/2006 | Saga et al. |
| 2006/0260334 A1 | 11/2006 | Carey et al. |
| 2007/0013532 A1 | 1/2007 | Ehlers |
| 2007/0045431 A1 | 3/2007 | Chapman et al. |
| 2007/0050732 A1 | 3/2007 | Chapman et al. |
| 2007/0057079 A1 | 3/2007 | Stark et al. |
| 2007/0114295 A1 | 5/2007 | Jenkins |
| 2007/0198099 A9 | 8/2007 | Shah |
| 2007/0228182 A1 | 10/2007 | Wagner et al. |
| 2007/0228183 A1 | 10/2007 | Kennedy et al. |
| 2007/0241203 A1 | 10/2007 | Wagner et al. |
| 2008/0048046 A1 | 2/2008 | Wagner et al. |
| 2008/0054084 A1 | 3/2008 | Olson |
| 2008/0099568 A1 | 5/2008 | Nicodem et al. |
| 2008/0120446 A1 | 5/2008 | Butler et al. |
| 2008/0161978 A1 | 7/2008 | Shah |
| 2008/0216495 A1 | 9/2008 | Kates |
| 2008/0223051 A1 | 9/2008 | Kates |
| 2008/0227430 A1 | 9/2008 | Polk |
| 2008/0280637 A1 | 11/2008 | Shaffer et al. |
| 2008/0289347 A1 | 11/2008 | Kadle et al. |
| 2008/0290183 A1 | 11/2008 | Laberge et al. |
| 2008/0294274 A1 | 11/2008 | Laberge et al. |
| 2008/0295030 A1 | 11/2008 | Laberge et al. |
| 2009/0140065 A1 | 6/2009 | Juntunen et al. |
| 2009/0143880 A1 | 6/2009 | Amundson et al. |
| 2009/0143918 A1 | 6/2009 | Amundson et al. |
| 2009/0144015 A1 | 6/2009 | Bedard |
| 2009/0251422 A1 | 10/2009 | Wu et al. |
| 2009/0276096 A1 | 11/2009 | Proffitt et al. |
| 2010/0070092 A1 | 3/2010 | Winter et al. |
| 2010/0084482 A1 | 4/2010 | Kennedy et al. |
| 2010/0131884 A1 | 5/2010 | Shah |
| 2010/0163633 A1 | 7/2010 | Barrett et al. |
| 2010/0163635 A1 | 7/2010 | Ye |
| 2010/0171889 A1 | 7/2010 | Pantel et al. |
| 2010/0182743 A1 | 7/2010 | Roher |
| 2010/0190479 A1 | 7/2010 | Scott et al. |
| 2010/0204834 A1 | 8/2010 | Comerford et al. |
| 2010/0212879 A1 | 8/2010 | Schnell et al. |
| 2010/0250707 A1 | 9/2010 | Dalley et al. |
| 2011/0006887 A1 | 1/2011 | Shaull et al. |
| 2011/0067851 A1 | 3/2011 | Terlson et al. |
| 2011/0088416 A1 | 4/2011 | Koethler |
| 2011/0132991 A1 | 6/2011 | Moody et al. |
| 2011/0181412 A1 | 7/2011 | Alexander et al. |
| 2011/0264279 A1 | 10/2011 | Poth |
| 2012/0001873 A1 | 1/2012 | Wu et al. |
| 2012/0007555 A1 | 1/2012 | Bukow |
| 2012/0048955 A1 | 3/2012 | Lin et al. |
| 2012/0061480 A1 | 3/2012 | Deligiannis et al. |
| 2012/0093141 A1 | 4/2012 | Imes et al. |
| 2012/0095601 A1 | 4/2012 | Abraham et al. |
| 2012/0101637 A1 | 4/2012 | Imes et al. |
| 2012/0126020 A1 | 5/2012 | Filson et al. |
| 2012/0126021 A1 | 5/2012 | Warren et al. |
| 2012/0131504 A1 | 5/2012 | Fadell et al. |
| 2012/0165993 A1 | 6/2012 | Whitehouse |
| 2012/0179727 A1 | 7/2012 | Esser |
| 2012/0181010 A1 | 7/2012 | Schultz et al. |
| 2012/0191257 A1 | 7/2012 | Corcoran et al. |
| 2012/0193437 A1 | 8/2012 | Henry et al. |
| 2012/0229521 A1 | 9/2012 | Hales et al. |
| 2012/0230661 A1 | 9/2012 | Alhilo |
| 2012/0239207 A1 | 9/2012 | Fadell et al. |
| 2012/0252430 A1 | 10/2012 | Imes et al. |
| 2012/0259470 A1 | 10/2012 | Nijhawan et al. |
| 2012/0298763 A1 | 11/2012 | Young |
| 2012/0303165 A1 | 11/2012 | Qu et al. |
| 2012/0303828 A1 | 11/2012 | Young et al. |
| 2012/0310418 A1 | 12/2012 | Harrod et al. |
| 2012/0315848 A1 | 12/2012 | Smith et al. |
| 2013/0002447 A1 | 1/2013 | Vogel et al. |
| 2013/0054758 A1 | 2/2013 | Imes et al. |
| 2013/0057381 A1 | 3/2013 | Kandhasamy |
| 2013/0087628 A1 | 4/2013 | Nelson et al. |
| 2013/0090767 A1 | 4/2013 | Bruck et al. |
| 2013/0099008 A1 | 4/2013 | Aljabari et al. |
| 2013/0099009 A1 | 4/2013 | Filson et al. |
| 2013/0123991 A1 | 5/2013 | Richmond |
| 2013/0138250 A1 | 5/2013 | Mowery et al. |
| 2013/0144443 A1 | 6/2013 | Casson et al. |
| 2013/0151016 A1 | 6/2013 | Bias et al. |
| 2013/0151018 A1 | 6/2013 | Bias et al. |
| 2013/0158721 A1 | 6/2013 | Somasundaram et al. |

(56) References Cited

U.S. PATENT DOCUMENTS

| | | |
|---|---|---|
| 2013/0163300 A1 | 6/2013 | Zhao et al. |
| 2013/0180700 A1 | 7/2013 | Aycock |
| 2013/0190932 A1 | 7/2013 | Schuman |
| 2013/0190940 A1 | 7/2013 | Sloop et al. |
| 2013/0204408 A1 | 8/2013 | Thiruvengada et al. |
| 2013/0204441 A1 | 8/2013 | Sloo et al. |
| 2013/0204442 A1 | 8/2013 | Modi et al. |
| 2013/0211600 A1 | 8/2013 | Dean-Hendricks et al. |
| 2013/0215058 A1 | 8/2013 | Brazell et al. |
| 2013/0221117 A1 | 8/2013 | Warren et al. |
| 2013/0228633 A1 | 9/2013 | Toth et al. |
| 2013/0234840 A1 | 9/2013 | Trundle et al. |
| 2013/0238142 A1 | 9/2013 | Nichols et al. |
| 2013/0245838 A1 | 9/2013 | Zywicki et al. |
| 2013/0261803 A1 | 10/2013 | Kolavennu |
| 2013/0261807 A1 | 10/2013 | Zywicki et al. |
| 2013/0268129 A1 | 10/2013 | Fadell et al. |
| 2013/0271670 A1 | 10/2013 | Sakata et al. |
| 2013/0292481 A1 | 11/2013 | Filson et al. |
| 2013/0297078 A1 | 11/2013 | Kolavennu |
| 2013/0318217 A1 | 11/2013 | Imes et al. |
| 2013/0318444 A1 | 11/2013 | Imes et al. |
| 2013/0325190 A1 | 12/2013 | Imes et al. |
| 2013/0338837 A1 | 12/2013 | Hublou et al. |
| 2013/0338839 A1 | 12/2013 | Rogers et al. |
| 2013/0340993 A1 | 12/2013 | Siddaramanna et al. |
| 2013/0345882 A1 | 12/2013 | Dushane et al. |
| 2014/0000861 A1 | 1/2014 | Barrett et al. |
| 2014/0002461 A1 | 1/2014 | Wang |
| 2014/0031989 A1 | 1/2014 | Bergman et al. |
| 2014/0034284 A1 | 2/2014 | Butler et al. |
| 2014/0039692 A1 | 2/2014 | Leen et al. |
| 2014/0041846 A1 | 2/2014 | Leen et al. |
| 2014/0048608 A1 | 2/2014 | Frank |
| 2014/0052300 A1 | 2/2014 | Matsuoka et al. |
| 2014/0058806 A1 | 2/2014 | Guenette et al. |
| 2014/0070919 A1 | 3/2014 | Jackson et al. |
| 2014/0081466 A1 | 3/2014 | Huapeng et al. |
| 2014/0112331 A1 | 4/2014 | Rosen |
| 2014/0114706 A1 | 4/2014 | Blakely |
| 2014/0117103 A1 | 5/2014 | Rossi et al. |
| 2014/0118285 A1 | 5/2014 | Poplawski |
| 2014/0129034 A1 | 5/2014 | Stefanski et al. |
| 2014/0149270 A1 | 5/2014 | Lombard et al. |
| 2014/0151456 A1 | 6/2014 | McCurnin et al. |
| 2014/0152631 A1 | 6/2014 | Moore et al. |
| 2014/0156087 A1 | 6/2014 | Amundson |
| 2014/0158338 A1 | 6/2014 | Kates |
| 2014/0165612 A1 | 6/2014 | Qu et al. |
| 2014/0175181 A1 | 6/2014 | Warren et al. |
| 2014/0188288 A1 | 7/2014 | Fisher et al. |
| 2014/0191848 A1 | 7/2014 | Imes et al. |
| 2014/0207291 A1 | 7/2014 | Golden et al. |
| 2014/0207292 A1 | 7/2014 | Ramagem et al. |
| 2014/0214212 A1 | 7/2014 | Leen et al. |
| 2014/0216078 A1 | 8/2014 | Ladd |
| 2014/0217185 A1 | 8/2014 | Bicknell |
| 2014/0217186 A1 | 8/2014 | Kramer et al. |
| 2014/0228983 A1 | 8/2014 | Groskreutz et al. |
| 2014/0231530 A1 | 8/2014 | Warren et al. |
| 2014/0244047 A1 | 8/2014 | Oh et al. |
| 2014/0250399 A1 | 9/2014 | Gaherwar |
| 2014/0262196 A1 | 9/2014 | Frank et al. |
| 2014/0262484 A1 | 9/2014 | Khoury et al. |
| 2014/0263679 A1 | 9/2014 | Conner et al. |
| 2014/0267008 A1 | 9/2014 | Jain et al. |
| 2014/0277762 A1 | 9/2014 | Drew |
| 2014/0277769 A1 | 9/2014 | Matsuoka et al. |
| 2014/0277770 A1 | 9/2014 | Aljabari et al. |
| 2014/0299670 A1 | 10/2014 | Ramachandran et al. |
| 2014/0309792 A1 | 10/2014 | Drew |
| 2014/0312129 A1 | 10/2014 | Zikes et al. |
| 2014/0312131 A1 | 10/2014 | Tousignant et al. |
| 2014/0312694 A1 | 10/2014 | Tu et al. |
| 2014/0316585 A1 | 10/2014 | Boesveld et al. |
| 2014/0316586 A1 | 10/2014 | Boesveld et al. |
| 2014/0316587 A1 | 10/2014 | Imes et al. |
| 2014/0317029 A1 | 10/2014 | Matsuoka et al. |
| 2014/0319231 A1 | 10/2014 | Matsuoka et al. |
| 2014/0319236 A1 | 10/2014 | Novotny et al. |
| 2014/0320282 A1 | 10/2014 | Zhang |
| 2014/0321011 A1 | 10/2014 | Bisson et al. |
| 2014/0324232 A1 | 10/2014 | Modi et al. |
| 2014/0330435 A1 | 11/2014 | Stoner et al. |
| 2014/0346239 A1 | 11/2014 | Fadell et al. |
| 2014/0358295 A1 | 12/2014 | Warren et al. |
| 2014/0367475 A1 | 12/2014 | Fadell et al. |
| 2014/0376530 A1 | 12/2014 | Erickson et al. |
| 2015/0001361 A1 | 1/2015 | Gagne et al. |
| 2015/0002165 A1 | 1/2015 | Juntunen et al. |
| 2015/0016443 A1 | 1/2015 | Erickson et al. |
| 2015/0025693 A1 | 1/2015 | Wu et al. |
| 2015/0039137 A1 | 2/2015 | Perry et al. |
| 2015/0041551 A1 | 2/2015 | Tessier et al. |
| 2015/0043615 A1 | 2/2015 | Steinberg et al. |
| 2015/0053779 A1 | 2/2015 | Adamek et al. |
| 2015/0053780 A1 | 2/2015 | Nelson et al. |
| 2015/0053781 A1 | 2/2015 | Nelson et al. |
| 2015/0058779 A1 | 2/2015 | Bruck et al. |
| 2015/0061859 A1 | 3/2015 | Matsuoka et al. |
| 2015/0066215 A1 | 3/2015 | Buduri |
| 2015/0066216 A1 | 3/2015 | Ramachandran |
| 2015/0066220 A1 | 3/2015 | Sloo et al. |
| 2015/0081106 A1 | 3/2015 | Buduri |
| 2015/0081109 A1 | 3/2015 | Fadell et al. |
| 2015/0081568 A1 | 3/2015 | Land, III |
| 2015/0088272 A1 | 3/2015 | Drew |
| 2015/0088318 A1 | 3/2015 | Amundson et al. |
| 2015/0100166 A1 | 4/2015 | Baynes et al. |
| 2015/0100167 A1 | 4/2015 | Sloo et al. |
| 2015/0115045 A1 | 4/2015 | Tu et al. |
| 2015/0115046 A1 | 4/2015 | Warren et al. |
| 2015/0124853 A1 | 5/2015 | Huppi et al. |
| 2015/0127176 A1 | 5/2015 | Bergman et al. |
| 2015/0140994 A1 | 5/2015 | Partheesh et al. |
| 2015/0142180 A1 | 5/2015 | Matsuoka et al. |
| 2015/0144706 A1 | 5/2015 | Robideau et al. |
| 2015/0145653 A1 | 5/2015 | Katingari et al. |
| 2015/0148963 A1 | 5/2015 | Klein et al. |
| 2015/0153057 A1 | 6/2015 | Matsuoka et al. |
| 2015/0153060 A1 | 6/2015 | Stefanski et al. |
| 2015/0156631 A1 | 6/2015 | Ramachandran |
| 2015/0159893 A1 | 6/2015 | Daubman et al. |
| 2015/0159899 A1 | 6/2015 | Bergman et al. |
| 2015/0159902 A1 | 6/2015 | Quam et al. |
| 2015/0159903 A1 | 6/2015 | Marak et al. |
| 2015/0159904 A1 | 6/2015 | Barton |
| 2015/0160691 A1 | 6/2015 | Kadah et al. |
| 2015/0163945 A1 | 6/2015 | Barton et al. |
| 2015/0167995 A1 | 6/2015 | Fadell et al. |
| 2015/0168002 A1 | 6/2015 | Plitkins et al. |
| 2015/0168003 A1 | 6/2015 | Stefanski et al. |
| 2015/0168933 A1 | 6/2015 | Klein et al. |
| 2015/0176854 A1 | 6/2015 | Butler et al. |
| 2015/0176855 A1 | 6/2015 | Geadelmann et al. |
| 2015/0198346 A1 | 7/2015 | Vedpathak |
| 2015/0198347 A1 | 7/2015 | Tessier et al. |
| 2015/0204558 A1 | 7/2015 | Sartain et al. |
| 2015/0204561 A1 | 7/2015 | Sadwick et al. |
| 2015/0204563 A1 | 7/2015 | Imes et al. |
| 2015/0204564 A1 | 7/2015 | Shah |
| 2015/0204565 A1 | 7/2015 | Amundson et al. |
| 2015/0204569 A1 | 7/2015 | Lorenz et al. |
| 2015/0204570 A1 | 7/2015 | Adamik et al. |
| 2015/0205310 A1 | 7/2015 | Amundson et al. |
| 2015/0219357 A1 | 8/2015 | Stefanski et al. |
| 2015/0233594 A1 | 8/2015 | Abe et al. |
| 2015/0233595 A1 | 8/2015 | Fadell et al. |
| 2015/0233596 A1 | 8/2015 | Warren et al. |
| 2015/0234369 A1 | 8/2015 | Wen et al. |
| 2015/0241078 A1 | 8/2015 | Matsuoka et al. |
| 2015/0245189 A1 | 8/2015 | Nalluri et al. |
| 2015/0248118 A1 | 9/2015 | Li et al. |
| 2015/0249605 A1 | 9/2015 | Erickson et al. |

(56) References Cited

U.S. PATENT DOCUMENTS

| | | |
|---|---|---|
| 2015/0260424 A1 | 9/2015 | Fadell et al. |
| 2015/0267935 A1 | 9/2015 | Devenish et al. |
| 2015/0268652 A1 | 9/2015 | Lunacek et al. |
| 2015/0276237 A1 | 10/2015 | Daniels et al. |
| 2015/0276238 A1 | 10/2015 | Matsuoka et al. |
| 2015/0276239 A1 | 10/2015 | Fadell et al. |
| 2015/0276254 A1 | 10/2015 | Nemcek et al. |
| 2015/0276266 A1 | 10/2015 | Warren et al. |
| 2015/0277463 A1 | 10/2015 | Hazzard et al. |
| 2015/0277492 A1 | 10/2015 | Chau et al. |
| 2015/0280935 A1 | 10/2015 | Poplawski et al. |
| 2015/0287310 A1 | 10/2015 | Deiiuliis et al. |
| 2015/0292764 A1 | 10/2015 | Land et al. |
| 2015/0292765 A1 | 10/2015 | Matsuoka et al. |
| 2015/0293541 A1 | 10/2015 | Fadell et al. |
| 2015/0300672 A1 | 10/2015 | Fadell et al. |
| 2015/0312696 A1 | 10/2015 | Ribbich et al. |
| 2015/0316285 A1 | 11/2015 | Clifton et al. |
| 2015/0316286 A1 | 11/2015 | Roher |
| 2015/0316902 A1 | 11/2015 | Wenzel et al. |
| 2015/0323212 A1 | 11/2015 | Warren et al. |
| 2015/0327010 A1 | 11/2015 | Gottschalk et al. |
| 2015/0327084 A1 | 11/2015 | Ramachandran et al. |
| 2015/0327375 A1 | 11/2015 | Bick et al. |
| 2015/0330654 A1 | 11/2015 | Matsuoka |
| 2015/0330658 A1 | 11/2015 | Filson et al. |
| 2015/0330660 A1 | 11/2015 | Filson et al. |
| 2015/0332150 A1 | 11/2015 | Thompson |
| 2015/0338117 A1 | 11/2015 | Henneberger et al. |
| 2015/0345818 A1 | 12/2015 | Oh et al. |
| 2015/0348554 A1 | 12/2015 | Orr et al. |
| 2015/0354844 A1 | 12/2015 | Kates |
| 2015/0354846 A1 | 12/2015 | Hales et al. |
| 2015/0355371 A1 | 12/2015 | Ableitner et al. |
| 2015/0362208 A1 | 12/2015 | Novotny et al. |
| 2015/0362926 A1 | 12/2015 | Yarde et al. |
| 2015/0362927 A1 | 12/2015 | Giorgi |
| 2015/0364135 A1 | 12/2015 | Kolavennu et al. |
| 2015/0370270 A1 | 12/2015 | Pan et al. |
| 2015/0370272 A1 | 12/2015 | Reddy et al. |
| 2015/0370615 A1 | 12/2015 | Pi-Sunyer |
| 2015/0370621 A1 | 12/2015 | Karp et al. |
| 2015/0372832 A1 | 12/2015 | Kortz et al. |
| 2015/0372834 A1 | 12/2015 | Karp et al. |
| 2015/0372999 A1 | 12/2015 | Pi-Sunyer |
| 2016/0006274 A1 | 1/2016 | Tu et al. |
| 2016/0006577 A1 | 1/2016 | Logan |
| 2016/0010880 A1 | 1/2016 | Bravard et al. |
| 2016/0018122 A1 | 1/2016 | Frank et al. |
| 2016/0018127 A1 | 1/2016 | Gourlay et al. |
| 2016/0020590 A1 | 1/2016 | Roosli et al. |
| 2016/0026194 A1 | 1/2016 | Mucignat et al. |
| 2016/0036227 A1 | 2/2016 | Schultz et al. |
| 2016/0040903 A1 | 2/2016 | Emmons et al. |
| 2016/0047569 A1 | 2/2016 | Fadell et al. |
| 2016/0054022 A1 | 2/2016 | Matas et al. |
| 2016/0054792 A1 | 2/2016 | Poupyrev |
| 2016/0054988 A1 | 2/2016 | Desire |
| 2016/0061471 A1 | 3/2016 | Eicher et al. |
| 2016/0061474 A1 | 3/2016 | Cheung et al. |
| 2016/0069582 A1 | 3/2016 | Buduri |
| 2016/0069583 A1 | 3/2016 | Fadell et al. |
| 2016/0077532 A1 | 3/2016 | Lagerstedt et al. |
| 2016/0088041 A1 | 3/2016 | Nichols |
| 2016/0107820 A1 | 4/2016 | Macvittie et al. |
| 2016/0287166 A1 | 10/2016 | Tran |
| 2016/0327298 A1 | 11/2016 | Sinha et al. |
| 2016/0327299 A1 | 11/2016 | Ribbich et al. |
| 2016/0327300 A1 | 11/2016 | Ribbich et al. |
| 2016/0327301 A1 | 11/2016 | Ribbich et al. |
| 2016/0327302 A1 | 11/2016 | Ribbich et al. |
| 2016/0327921 A1 | 11/2016 | Ribbich et al. |
| 2016/0377306 A1 | 12/2016 | Drees et al. |
| 2017/0074536 A1 | 3/2017 | Bentz et al. |
| 2017/0074537 A1 | 3/2017 | Bentz et al. |
| 2017/0074539 A1 | 3/2017 | Bentz et al. |
| 2017/0074541 A1 | 3/2017 | Bentz et al. |
| 2017/0075510 A1 | 3/2017 | Bentz et al. |
| 2017/0075568 A1 | 3/2017 | Bentz et al. |
| 2017/0076263 A1 | 3/2017 | Bentz et al. |
| 2017/0102162 A1 | 4/2017 | Drees et al. |
| 2017/0102433 A1 | 4/2017 | Wenzel et al. |
| 2017/0102434 A1 | 4/2017 | Wenzel et al. |
| 2017/0102675 A1 | 4/2017 | Drees |
| 2017/0103483 A1 | 4/2017 | Drees et al. |
| 2017/0104332 A1 | 4/2017 | Wenzel et al. |
| 2017/0104336 A1 | 4/2017 | Elbsat et al. |
| 2017/0104337 A1 | 4/2017 | Drees |
| 2017/0104342 A1 | 4/2017 | Elbsat et al. |
| 2017/0104343 A1 | 4/2017 | Elbsat et al. |
| 2017/0104344 A1 | 4/2017 | Wenzel et al. |
| 2017/0104345 A1 | 4/2017 | Wenzel et al. |
| 2017/0104346 A1 | 4/2017 | Wenzel et al. |
| 2017/0104449 A1 | 4/2017 | Drees |
| 2017/0122613 A1 | 5/2017 | Sinha et al. |
| 2017/0122617 A1 | 5/2017 | Sinha et al. |
| 2017/0123391 A1 | 5/2017 | Sinha et al. |
| 2017/0124838 A1 | 5/2017 | Sinha et al. |
| 2017/0124842 A1 | 5/2017 | Sinha et al. |
| 2017/0131825 A1 | 5/2017 | Moore et al. |
| 2017/0295058 A1 | 10/2017 | Gottschalk et al. |
| 2017/0357607 A1 | 12/2017 | Cayemberg et al. |

FOREIGN PATENT DOCUMENTS

| | | |
|---|---|---|
| CA | 2633121 C | 8/2011 |
| CA | 2818356 | 5/2012 |
| CA | 2818696 A1 | 5/2012 |
| CA | 2853041 | 4/2013 |
| CA | 2853081 A1 | 4/2013 |
| CA | 2812567 | 5/2014 |
| CA | 2886531 A1 | 9/2015 |
| CA | 2894359 A1 | 12/2015 |
| DE | 10 2004 005 962 | 8/2005 |
| EP | 2 283 279 A2 | 2/2011 |
| EP | 2 738 478 A2 | 6/2014 |
| EP | 2 897 018 A1 | 7/2015 |
| EP | 2 988 188 A2 | 2/2016 |
| GB | 2 519 441 A | 4/2015 |
| WO | WO-00/22491 A1 | 4/2000 |
| WO | WO-2006/041599 A9 | 7/2006 |
| WO | WO-2009/006133 A1 | 1/2009 |
| WO | WO-2009/058127 A1 | 5/2009 |
| WO | WO-2009/036764 A3 | 1/2010 |
| WO | WO-2010/059143 A1 | 5/2010 |
| WO | WO-2010/078459 A1 | 7/2010 |
| WO | WO-2010/088663 A1 | 8/2010 |
| WO | WO-2012/042232 | 4/2012 |
| WO | WO-2012/068436 A1 | 5/2012 |
| WO | WO-2012/068495 A1 | 5/2012 |
| WO | WO-2012/068503 A1 | 5/2012 |
| WO | WO-2012/068507 A3 | 5/2012 |
| WO | WO-2012/068517 A1 | 5/2012 |
| WO | WO-2012/068526 A1 | 5/2012 |
| WO | WO-2013/033469 A1 | 3/2013 |
| WO | WO-2013/052389 A1 | 4/2013 |
| WO | WO-2013/052905 A1 | 4/2013 |
| WO | WO-2013/058933 A1 | 4/2013 |
| WO | WO-2013/058934 | 4/2013 |
| WO | WO-2013/058968 A1 | 4/2013 |
| WO | WO-2013/058969 A1 | 4/2013 |
| WO | WO-2013/059684 A1 | 4/2013 |
| WO | WO-2012/142477 A3 | 8/2013 |
| WO | WO-2013/153480 A3 | 12/2013 |
| WO | WO-2014/047501 A1 | 3/2014 |
| WO | WO-2012/068437 A3 | 4/2014 |
| WO | WO-2012/068459 A3 | 4/2014 |
| WO | WO-2013/058932 | 4/2014 |
| WO | WO-2014/051632 A1 | 4/2014 |
| WO | WO-2014/051635 A1 | 4/2014 |
| WO | WO-2014/055059 A1 | 4/2014 |
| WO | WO-2013/052901 A3 | 5/2014 |
| WO | WO-2014/152301 A2 | 9/2014 |
| WO | WO-2014/152301 A3 | 9/2014 |

(56) References Cited

FOREIGN PATENT DOCUMENTS

| WO | WO-2015/012449 A1 | 1/2015 |
|---|---|---|
| WO | WO-2015/039178 A1 | 3/2015 |
| WO | WO-2015/054272 A2 | 4/2015 |
| WO | WO-2015/057698 A1 | 4/2015 |
| WO | WO-2015/099721 A1 | 7/2015 |
| WO | WO-2015/127499 A1 | 9/2015 |
| WO | WO-2015/127566 A1 | 9/2015 |
| WO | WO-2015/134755 A3 | 10/2015 |
| WO | WO-2015/195772 A1 | 12/2015 |
| WO | WO-2016/038374 A1 | 3/2016 |

OTHER PUBLICATIONS

U.S. Appl. No. 15/143,373, filed Apr. 29, 2016, Johnson Controls Technology Company.
U.S. Appl. No. 15/146,134, filed May 4, 2016, Johnson Controls Technology Company.
U.S. Appl. No. 15/146,202, filed May 4, 2016, Johnson Controls Technology Company.
U.S. Appl. No. 15/146,649, filed May 4, 2016, Johnson Controls Technology Company.
U.S. Appl. No. 15/146,749, filed May 4, 2016, Johnson Controls Technology Company.
U.S. Appl. No. 15/146,763, filed May 4, 2016, Johnson Controls Technology Company.
U.S. Appl. No. 15/179,894, filed Jun. 10, 2016, Johnson Controls Technology Company.
U.S. Appl. No. 15/207,431, filed Jul. 11, 2016, Johnson Controls Technology Company.
U.S. Appl. No. 15/247,777, filed Aug. 25, 2016, Johnson Controls Technology Company.
U.S. Appl. No. 15/247,784, filed Aug. 25, 2016, Johnson Controls Technology Company.
U.S. Appl. No. 15/247,788, filed Aug. 25, 2016, Johnson Controls Technology Company.
U.S. Appl. No. 15/247,793, filed Aug. 25, 2016, Johnson Controls Technology Company.
U.S. Appl. No. 15/247,844, filed Aug. 25, 2016, Johnson Controls Technology Company.
U.S. Appl. No. 15/247,869, filed Aug. 25, 2016, Johnson Controls Technology Company.
U.S. Appl. No. 15/247,872, filed Aug. 25, 2016, Johnson Controls Technology Company.
U.S. Appl. No. 15/247,873, filed Aug. 25, 2016, Johnson Controls Technology Company.
U.S. Appl. No. 15/247,875, filed Aug. 25, 2016, Johnson Controls Technology Company.
U.S. Appl. No. 15/247,879, filed Aug. 25, 2016, Johnson Controls Technology Company.
U.S. Appl. No. 15/247,880, filed Aug. 25, 2016, Johnson Controls Technology Company.
U.S. Appl. No. 15/247,881, filed Aug. 25, 2016, Johnson Controls Technology Company.
U.S. Appl. No. 15/247,883, filed Aug. 25, 2016, Johnson Controls Technology Company.
U.S. Appl. No. 15/247,885, filed Aug. 25, 2016, Johnson Controls Technology Company.
U.S. Appl. No. 15/247,886, filed Aug. 25, 2016, Johnson Controls Technology Company.
U.S. Appl. No. 15/260,293, filed Sep. 8, 2016, Johnson Controls Technology Company.
U.S. Appl. No. 15/260,295, filed Sep. 8, 2016, Johnson Controls Technology Company.
U.S. Appl. No. 15/260,297, filed Sep. 8, 2016, Johnson Controls Technology Company.
U.S. Appl. No. 15/260,299, filed Sep. 8, 2016, Johnson Controls Technology Company.
U.S. Appl. No. 15/260,301, filed Sep. 8, 2016, Johnson Controls Technology Company.
U.S. Appl. No. 15/336,789, filed Oct. 28, 2016, Johnson Controls Technology Company.
U.S. Appl. No. 15/336,791, filed Oct. 28, 2016, Johnson Controls Technology Company.
U.S. Appl. No. 15/336,792, filed Oct. 28, 2016, Johnson Controls Technology Company.
U.S. Appl. No. 15/336,793, filed Oct. 28, 2016, Johnson Controls Technology Company.
U.S. Appl. No. 15/338,215, filed Oct. 28, 2016, Johnson Controls Technology Company.
U.S. Appl. No. 15/338,221, filed Oct. 28, 2016, Johnson Controls Technology Company.
U.S. Appl. No. 15/397,722, filed Jan. 3, 2017, Johnson Controls Technology Company.
U.S. Appl. No. 29/525,907, filed May 4, 2015, Johnson Controls Technology Company.
U.S. Appl. No. 29/548,334, filed Dec. 11, 2015, Johnson Controls Technology Company.
U.S. Appl. No. 29/563,447, filed May 4, 2016, Johnson Controls Technology Company.
U.S. Appl. No. 29/576,515, filed Sep. 2, 2016, Johnson Controls Technology Company.
U.S. Appl. No. 62/239,131, filed Oct. 8, 2015, Johnson Controls Technology Company.
U.S. Appl. No. 62/239,231, filed Oct. 8, 2015, Johnson Controls Technology Company.
U.S. Appl. No. 62/239,233, filed Oct. 8, 2015, Johnson Controls Technology Company.
U.S. Appl. No. 62/239,245, filed Oct. 8, 2015, Johnson Controls Technology Company.
U.S. Appl. No. 62/239,246, filed Oct. 8, 2015, Johnson Controls Technology Company.
U.S. Appl. No. 62/239,249, filed Oct. 8, 2015, Johnson Controls Technology Company.
International Search Report and Written Opinion for Application No. PCT/US2016/030291, dated Sep. 7, 2016, 11 pages.
International Search Report and Written Opinion for Application No. PCT/US2016/030827, dated Sep. 7, 2016, 13 pages.
International Search Report and Written Opinion for Application No. PCT/US2016/030829, dated Sep. 7, 2016, 15 pages.
International Search Report and Written Opinion for Application No. PCT/US2016/030835, dated Sep. 7, 2016, 13 pages.
International Search Report and Written Opinion for Application No. PCT/US2016/030836, dated Sep. 7, 2016, 11 pages.
International Search Report and Written Opinion for Application No. PCT/US2016/030837, dated Sep. 7, 2016, 13 pages.
International Search Report and Written Opinion for Application No. PCT/US2016/051176, dated Feb. 16, 2017, 20 pages.
International Search Report and Written Opinion for Application No. PCT/US2017/012217, dated Mar. 31, 2017, 14 pages.
International Search Report and Written Opinion for Application No. PCT/US2017/012218, dated Mar. 31, 2017, 14 pages.
International Search Report and Written Opinion for Application No. PCT/US2017/012221, dated Mar. 31, 2017, 13 pages.
International Search Report and Written Opinion for Application No. PCT/US2017/030890, dated Jun. 21, 2017, 13 pages.
Notice of Allowance for U.S. Appl. No. 15/146,649, dated Feb. 27, 2018, 7 pages.
Notice of Allowance for U.S. Appl. No. 15/146,763, dated Oct. 4, 2017, 9 pages.
Notice of Allowance for U.S. Appl. No. 15/336,789, dated Feb. 19, 2019, 5 pages.
Office Action for U.S. Appl. No. 15/146,649, dated Oct. 6, 2017, 7 pages.
Office Action for U.S. Appl. No. 15/146,749, dated Mar. 19, 2018, 12 pages.
Office Action for U.S. Appl. No. 15/146,749, dated Oct. 4, 2017, 10 pages.
Office Action for U.S. Appl. No. 15/260,294, dated Feb. 16, 2018, 19 pages.
Office Action for U.S. Appl. No. 15/260,297, dated Jan. 30, 2018, 18 pages.

(56) References Cited

OTHER PUBLICATIONS

Office Action for U.S. Appl. No. 15/260,301, dated Feb. 9, 2018, 10 pages.
Office Action for U.S. Appl. No. 15/336,789, dated Aug. 10, 2017, 15 pages.
Office Action for U.S. Appl. No. 15/336,789, dated Aug. 9, 2018, 16 pages.
Office Action for U.S. Appl. No. 15/336,789, dated Feb. 22, 2018, 16 pages.
Office Action for U.S. Appl. No. 15/336,791, dated Mar. 2, 2018, 14 pages.
Office Action for U.S. Appl. No. 15/336,792, dated Mar. 29, 2018, 13 pages.
Office Action for U.S. Appl. No. 15/336,792, dated Oct. 10, 2017, 13 pages.
Unknown, National Semiconductor's Temperature Sensor Handbook, Nov. 1, 1997, retrieved from the Internet at http://shrubbery.net/~heas/willem/PDF/NSC/temphb.pdf on Aug. 11, 2016, pp. 1-40.
Written Opinion for Singapore Application No. 11201708996V, dated Dec. 27, 2017, 6 pages.
Written Opinion for Singapore Application No. 11201708997W, dated Jan. 10, 2018, 9 pages.
Written Opinion for Singapore Application No. 11201709002Y, dated Feb. 7, 2018, 5 pages.

1412

| | Preferred Setpoint | Music | Lighting | Shades/Blinds |
|---|---|---|---|---|
| Occupant A | 78°F | No Music | No Permission | Use Natural Light |
| Occupant B | 75°F | Radio Station AM 1130 | Dim | No Permission |
| Occupant C | No Permission | No Permission | Full Brightness | No Permission |

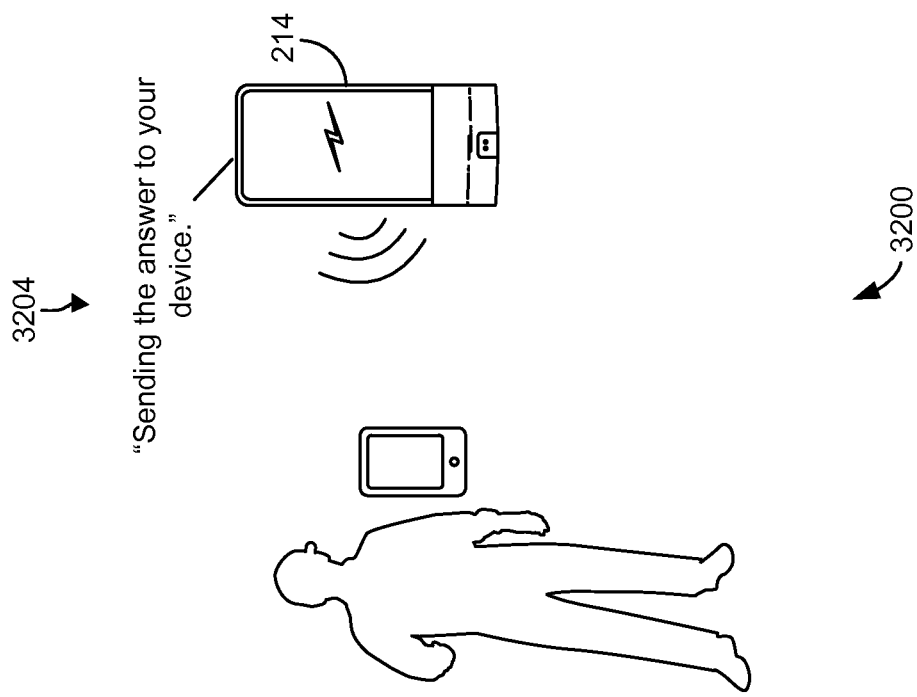
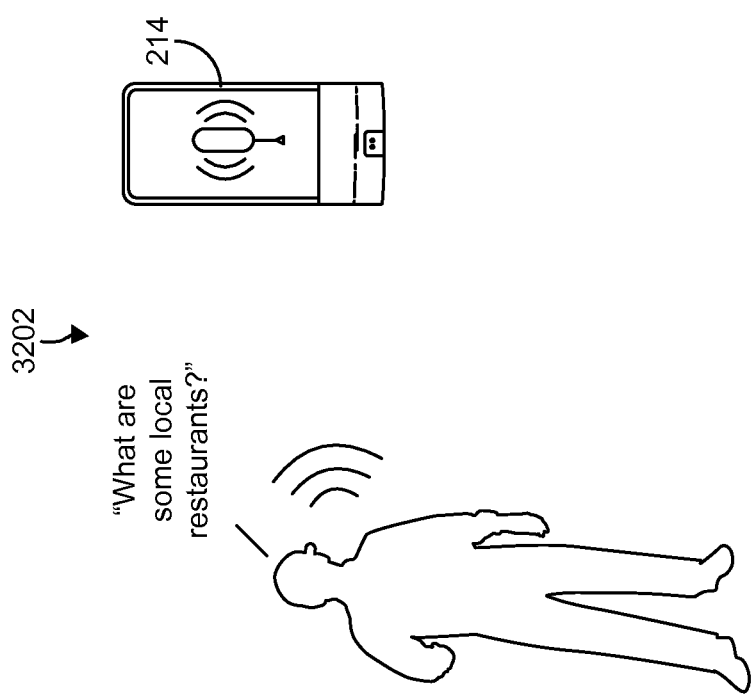
FIG. 32

MULTI-FUNCTION THERMOSTAT WITH HEALTH MONITORING FEATURES

CROSS-REFERENCE TO RELATED PATENT APPLICATIONS

This application is a continuation of U.S. patent application Ser. No. 15/336,789 filed Oct. 28, 2016, which claims the benefit of and priority to U.S. Provisional Patent Application No. 62/247,672 filed Oct. 28, 2015, U.S. Provisional Patent Application No. 62/274,750 filed Jan. 4, 2016, U.S. Provisional Patent Application No. 62/275,202 filed Jan. 5, 2016, U.S. Provisional Patent Application No. 62/275,204 filed Jan. 5, 2016, U.S. Provisional Patent Application No. 62/275,199 filed Jan. 5, 2016, and U.S. Provisional Patent Application No. 62/275,711 filed Jan. 6, 2016. The entire disclosure of each of these patent applications is incorporated by reference herein.

BACKGROUND

The present invention relates generally to thermostats and more particularly to the improved control of a building or space's heating, ventilating, and air conditioning (HVAC) system through the use of a multi-function thermostat.

A thermostat is, in general, a component of an HVAC control system. Traditional thermostats sense the temperature of a system and control components of the HVAC in order to maintain a setpoint. A thermostat may be designed to control a heating or cooling system or an air conditioner. Thermostats are manufactured in many ways, and use a variety of sensors to measure temperature and other desired parameters of a system.

Conventional thermostats are configured for one-way communication to connected components, and to control HVAC systems by turning on or off certain components or by regulating flow. Each thermostat may include a temperature sensor and a user interface. The user interface typically includes a display for presenting information to a user and one or more user interface elements for receiving input from a user. To control the temperature of a building or space, a user adjusts the setpoint via the thermostat's user interface.

SUMMARY

One implementation of the present disclosure is a multi-function thermostat for a building. The thermostat includes a communication interface and a processing circuit. The communications interface is configured to communicate with an emergency server and receive occupant health data from a health sensor configured to monitor an occupant. The processing circuit is configured to determine a health metric associated with the occupant based on the health values and cause the communications interface to send a distress message to the emergency server when the health metric associated with the occupant indicates a medical emergency of the occupant.

In some embodiments, the communications interface is configured to communicate with occupancy sensors. In some embodiments, the processing circuit is configured to identify the occupant based on occupancy data received from the occupancy sensors.

In some embodiments, the health sensor is a smart wrist band and the occupant health value includes at least one of a heart rate or a body temperature.

In some embodiments, the processing circuit is configured to determine the health metric associated with the occupant by comparing the health value indicating the measured biological condition of the occupant to a stored threshold value and calculating the health metric based on a result of the comparing. In some embodiments, the health value includes at least one of a body temperature of the occupant, a heart rate of the occupant, or an insulin level of the occupant.

In some embodiments, the health value includes a measured heart rate of the occupant. In some embodiments, the processing circuit is configured to determine the health metric associated with the occupant by monitoring the occupant health data for heart arrhythmia.

In some embodiments, the emergency server includes at least one of an emergency response operator server, a nurses' station computing system, and a hospital server. In some embodiments, the distress message includes a description of the medical emergency associated with the occupant.

In some embodiments, the processing circuit is configured to push health messages to a user device. The health messages include at least one of the distress message, a reminder to take medication, and a reminder for an appointment.

Another implementation of the present disclosure is a method for operating a multi-function thermostat for a building. The method includes receiving occupant health data from a health sensor via a communications interface of the thermostat. The method includes determining, by a processing circuit of the thermostat, a health metric associated with an occupant based on the health value. The method includes causing the communications interface to send a distress message to an emergency server when the health metric associated with the occupant indicates a medical emergency.

In some embodiments, the method further includes receiving occupancy data from an occupancy sensor via the communications interface and identifying the occupant based on occupancy data received from the occupancy sensor.

In some embodiments, the health sensors include a smart wrist band and the health value includes at least one of a heart rate and a body temperature.

In some embodiments, the health value includes a heart rate and determining the health metric includes monitoring the occupant health data for heart arrhythmia.

In some embodiments, the emergency server includes at least one of an emergency response operator server, a nurses' station computing system, and a hospital server, and the distress message includes a description of the medical emergency associated with the occupant.

Another implementation of the present disclosure is a multi-function thermostat for a building. The thermostat includes a communications interface configured to communicate with an emergency server and receive health data from a health sensor. The thermostat includes a processing circuit configured to cause the communications interface to send a distress message to server second thermostat when the health value associated with the occupant indicates a medical emergency.

In some embodiments, the health sensor includes a smart wrist band and the health value includes at least one of a heart rate and a body temperature.

In some embodiments, the processing circuit is configured to determine a heath metric by monitoring the health data for heart arrhythmia when the health value includes a heart rate and monitoring the heart rate for tachycardia or bradycardia when the health value includes a heart rate.

In some embodiments, the wearable health sensor is an insulin pump and the health value includes an insulin level of the individual. In some embodiments, the processing circuit is configured to compare the measured insulin level to a stored threshold value and calculate a health metric based on a result of the comparing.

BRIEF DESCRIPTION OF THE DRAWINGS

FIG. 14B is a table of occupant permissions and preferences for the control device of FIG. 7, according to an exemplary embodiment.

FIG. 32 is another flow diagram of operations for using a concierge feature of the control device of FIG. 7, according to an exemplary embodiment.

DETAILED DESCRIPTION

Overview

Referring generally to the FIGURES, a user control device is shown, according to various exemplary embodiments. The thermostat described herein may be used in any HVAC system, room, environment, or system within which it is desired to control and/or observe environmental conditions (e.g., temperature, humidity, etc.). In traditional HVAC systems, a thermostat may be adjusted by a user to control the temperature of a system.

The user control device is intended to provide the user with an ability to function as a connected smart hub. The thermostat provides a desirable user interface for other environmental controls because of its known fixed location within a space. The user control device is intended to be more personal, more efficient, and more aware than traditional thermostats.

The user control device collects data about a space and the occupants of the space with various sensors (e.g., temperature sensors, humidity sensors, acoustic sensors, optical sensors, gas and other chemical sensors, biometric sensors, motion sensors, etc.) and user inputs. The user control device may utilize data collected from a single room, multiple rooms, an entire building, or multiple buildings. The data may be analyzed locally by the user control device or may be uploaded to a remote computing system and/or the cloud for further analysis and processing.

Building Management System and HVAC System

Figure 1:
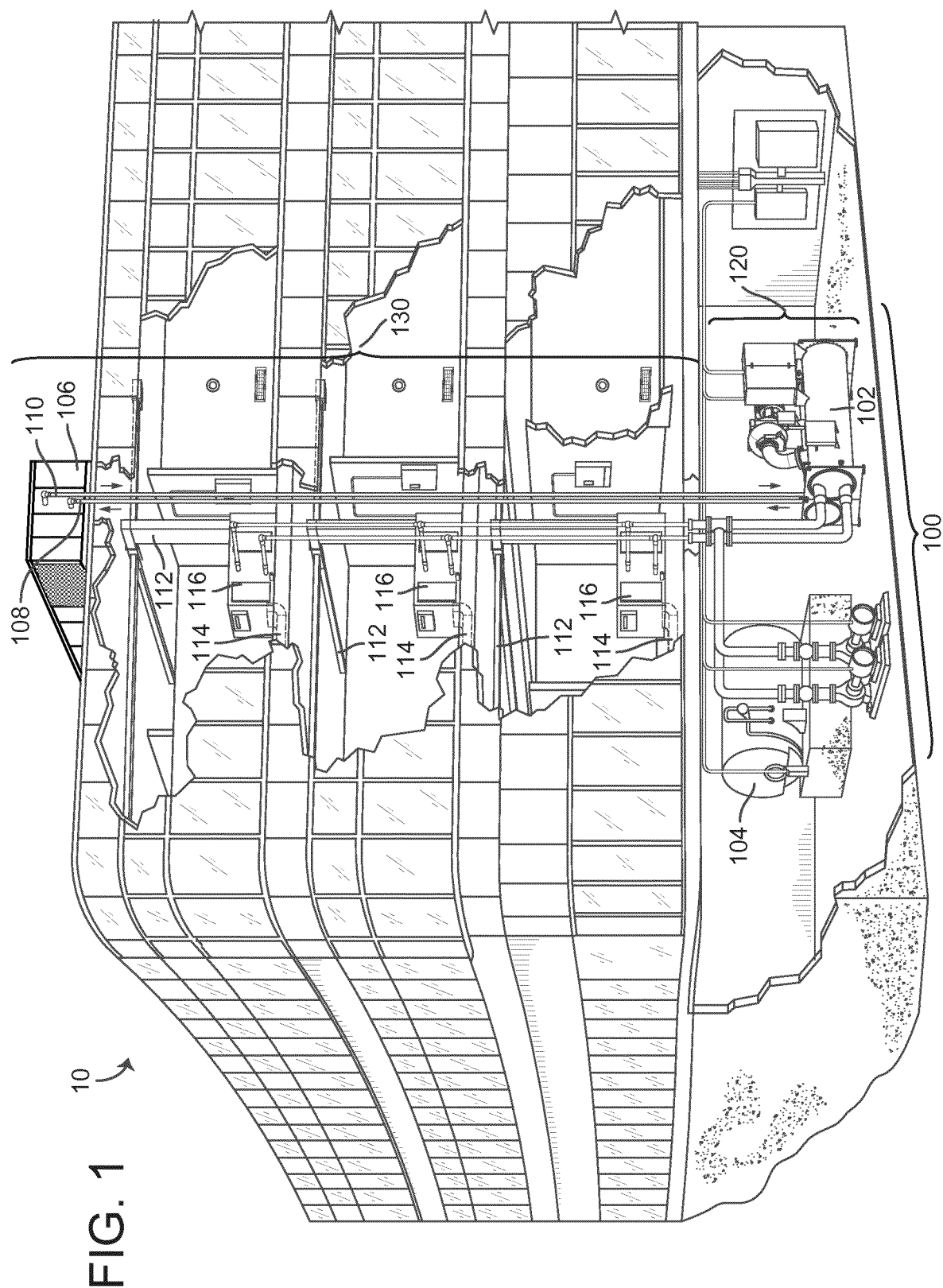
FIG. 1 is a drawing of a building equipped with a HVAC system, according to an exemplary embodiment.

Referring now to FIGS. 1-4, an exemplary building management system (BMS) and HVAC system in which the systems and methods of the present disclosure may be implemented are shown, according to an exemplary embodiment. Referring particularly to FIG. 1, a perspective view of a building 10 is shown. Building 10 is served by a BMS. A BMS is, in general, a system of devices configured to control, monitor, and manage equipment in or around a building or building area. A BMS can include, for example, a HVAC system, a security system, a lighting system, a fire alerting system, any other system that is capable of managing building functions or devices, or any combination thereof.

The BMS that serves building 10 includes an HVAC system 100. HVAC system 100 may include a plurality of HVAC devices (e.g., heaters, chillers, air handling units, pumps, fans, thermal energy storage, etc.) configured to provide heating, cooling, ventilation, or other services for building 10. For example, HVAC system 100 is shown to include a waterside system 120 and an airside system 130. Waterside system 120 may provide a heated or chilled fluid to an air handling unit of airside system 130. Airside system 130 may use the heated or chilled fluid to heat or cool an airflow provided to building 10. An exemplary waterside system and airside system which may be used in HVAC system 100 are described in greater detail with reference to FIGS. 2-3.

HVAC system 100 is shown to include a chiller 102, a boiler 104, and a rooftop air handling unit (AHU) 106. Waterside system 120 may use boiler 104 and chiller 102 to heat or cool a working fluid (e.g., water, glycol, etc.) and may circulate the working fluid to AHU 106. In various embodiments, the HVAC devices of waterside system 120 may be located in or around building 10 (as shown in FIG. 1) or at an offsite location such as a central plant (e.g., a chiller plant, a steam plant, a heat plant, etc.). The working fluid may be heated in boiler 104 or cooled in chiller 102, depending on whether heating or cooling is required in building 10. Boiler 104 may add heat to the circulated fluid, for example, by burning a combustible material (e.g., natural gas) or using an electric heating element. Chiller 102 may place the circulated fluid in a heat exchange relationship with another fluid (e.g., a refrigerant) in a heat exchanger (e.g., an evaporator) to absorb heat from the circulated fluid. The working fluid from chiller 102 and/or boiler 104 may be transported to AHU 106 via piping 108.

AHU 106 may place the working fluid in a heat exchange relationship with an airflow passing through AHU 106 (e.g., via one or more stages of cooling coils and/or heating coils). The airflow may be, for example, outside air, return air from within building 10, or a combination of both. AHU 106 may transfer heat between the airflow and the working fluid to provide heating or cooling for the airflow. For example, AHU 106 may include one or more fans or blowers configured to pass the airflow over or through a heat exchanger containing the working fluid. The working fluid may then return to chiller 102 or boiler 104 via piping 110.

Airside system 130 may deliver the airflow supplied by AHU 106 (i.e., the supply airflow) to building 10 via air supply ducts 112 and may provide return air from building 10 to AHU 106 via air return ducts 114. In some embodiments, airside system 130 includes multiple variable air volume (VAV) units 116. For example, airside system 130 is shown to include a separate VAV unit 116 on each floor or zone of building 10. VAV units 116 may include dampers or other flow control elements that can be operated to control an amount of the supply airflow provided to individual zones of building 10. In other embodiments, airside system 130 delivers the supply airflow into one or more zones of building 10 (e.g., via supply ducts 112) without using intermediate VAV units 116 or other flow control elements. AHU 106 may include various sensors (e.g., temperature sensors, pressure sensors, etc.) configured to measure attributes of the supply airflow. AHU 106 may receive input from sensors located within AHU 106 and/or within the building zone and may adjust the flow rate, temperature, or other attributes of the supply airflow through AHU 106 to achieve setpoint conditions for the building zone.

Figure 2:
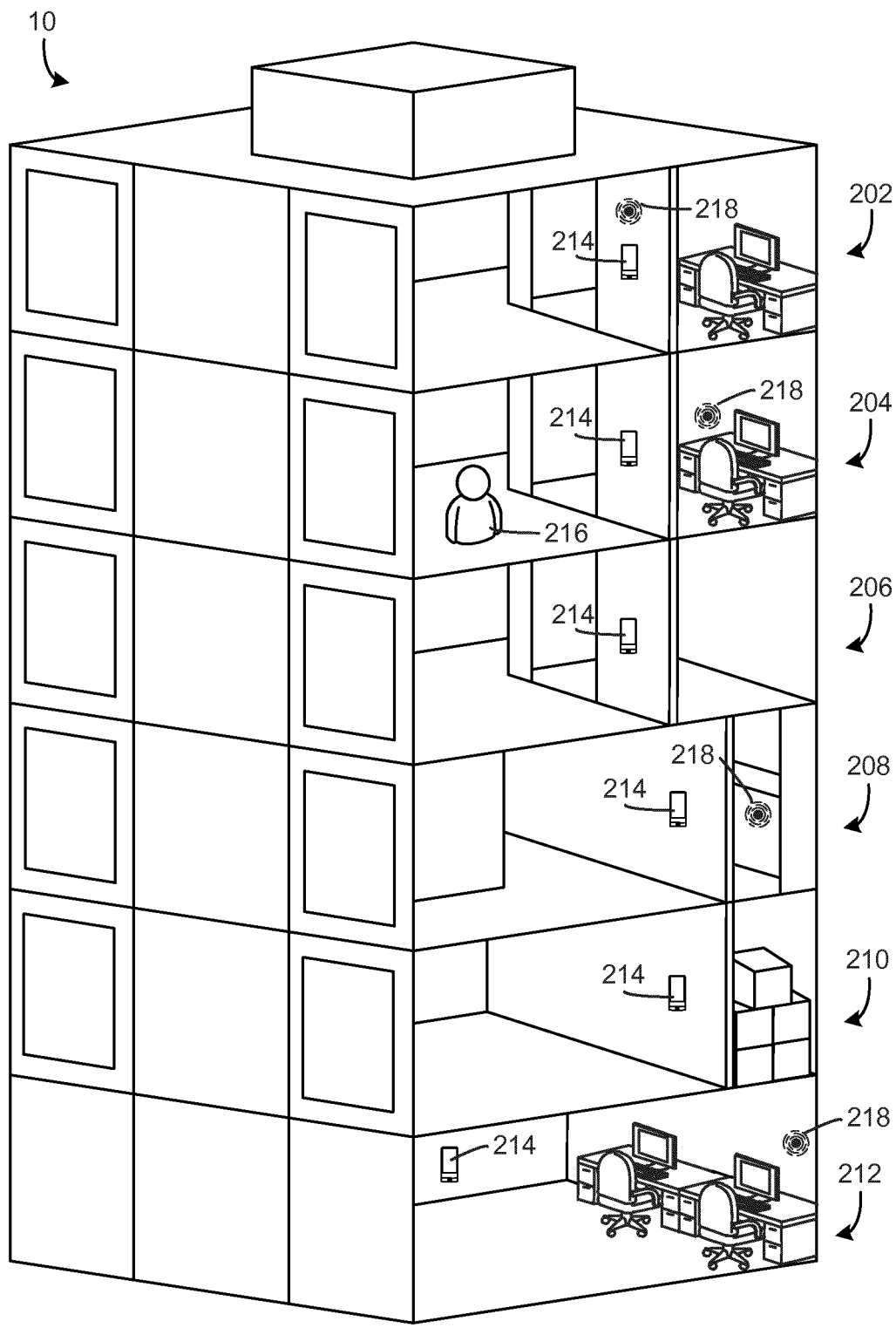
FIG. 2 is a drawing of multiple zones and floors of the building of FIG. 1 equipped with control devices, according to an exemplary embodiment.

Referring now to FIG. 2, building 10 is shown in greater detail, according to an exemplary embodiment. Building 10 may have multiple zones. In FIG. 2, building 10 has zones, 202, 204, 206, 208, 210, and 212. In building 10, the zones each correspond to a separate floor. In various embodiments, the zones of building 10 may be rooms, sections of a floor, multiple floors, etc. Each zone may have a corresponding control device 214. In some embodiments, control device 214 is at least one of a thermostat, a sensor, a controller, a display device, a concierge device, a medical monitor device, etc. Control device 214 may take input from users. The input may be an environmental setpoint, a concierge question, a payment, etc. In some embodiments, control device 214 can cause music and/or building announcements to be played in one or more of zones 202-212, cause the temperature and/or humidity to be regulated in one or more of zones 202-212, and/or any other control action.

In some embodiments, control device 214 can monitor the health of an occupant 216 of building 10. In some embodiments, control device 214 monitors heat signatures, heart-rates, and any other information that can be collected from cameras, medical devices, and/or any other health related sensor. In some embodiments, building 10 has wireless transmitters 218 in each or some of zones 202-212. The wireless transmitters 218 may be routers, coordinators, and/or any other device broadcasting radio waves. In some embodiments, wireless transmitters 218 form a Wi-Fi network, a Zigbee network, a Bluetooth network, and/or any other kind of network.

In some embodiments, occupant 216 has a mobile device that can communicate with wireless transmitters 218. Control device 214 may use the signal strengths between the mobile device of occupant 216 and the wireless transmitters 218 to determine what zone the occupant is in. In some embodiments, control device 214 causes temperature setpoints, music and/or other control actions to follow occupant 216 as the occupant 216 moves from one zone to another zone (i.e., from one floor to another floor).

In some embodiments, display devices 214 are connected to a building management system, a weather server, and/or a building emergency sensor(s). In some embodiments, display devices 214 may receive emergency notifications from the building management system, the weather server, and/or the building emergency sensor(s). Based on the nature of the emergency, display devices 214 may give directions to an occupant of the building. In some embodiments, the direction may be to respond to an emergency (e.g., call the police, hide and turn the lights off, etc.), In various embodiments, the directions given to the occupant (e.g., occupant 216) may be navigation directions. For example, zone 212 may be a safe zone with no windows an individual (e.g., occupant 216). If display devices 214 determines that there are high winds around building 10, the control device 214 may direct occupants of zones 202-210 to zone 212 if zone 212 has no windows.

Figure 3:
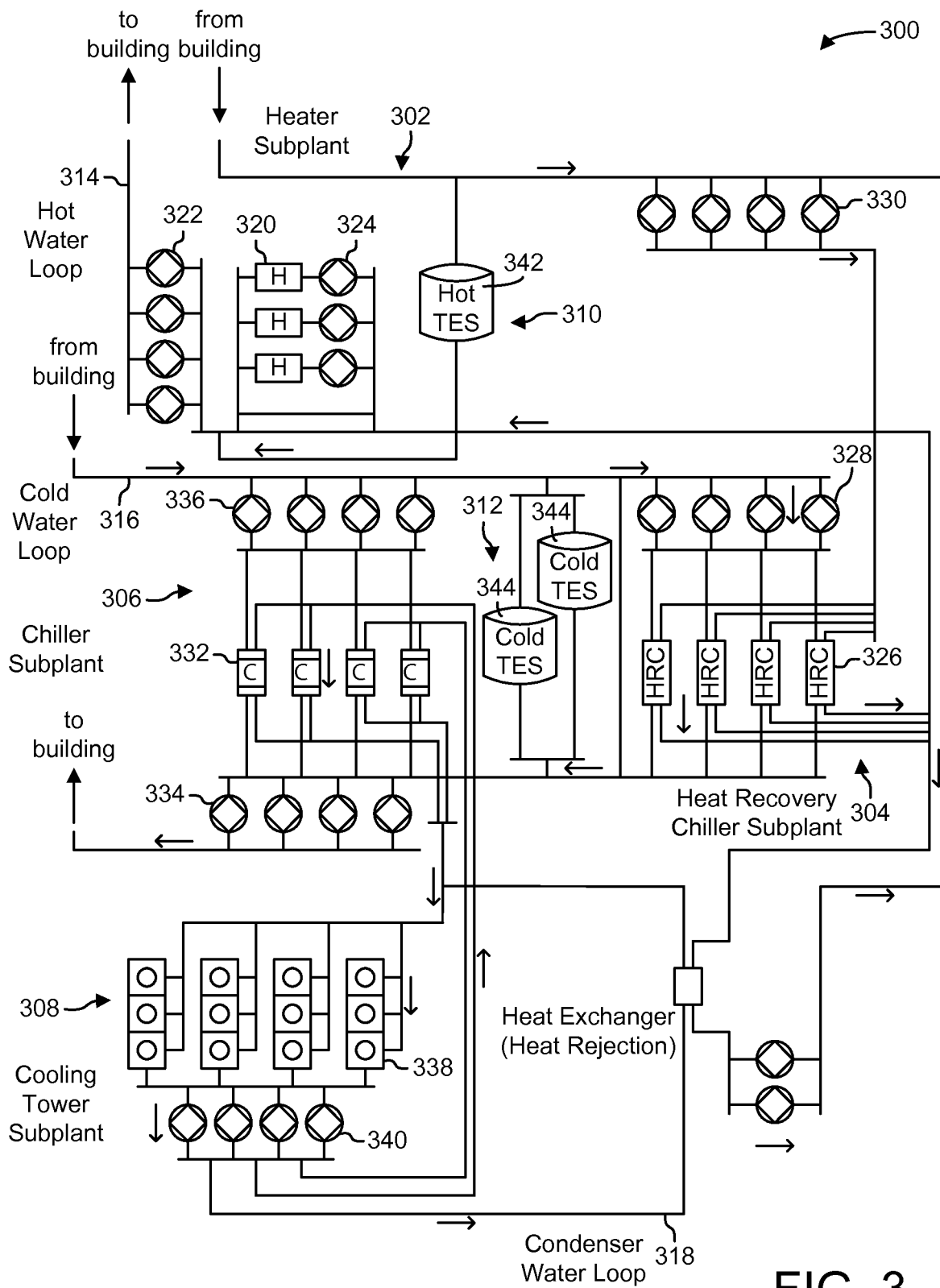
FIG. 3 is a block diagram of a waterside system that may be used in conjunction with the building of FIGS. 1-2, according to an exemplary embodiment.

Referring now to FIG. 3, a block diagram of a waterside system 300 is shown, according to an exemplary embodiment. In various embodiments, waterside system 300 may supplement or replace waterside system 120 in HVAC system 100 or may be implemented separate from HVAC system 100. When implemented in HVAC system 100, waterside system 300 may include a subset of the HVAC devices in HVAC system 100 (e.g., boiler 104, chiller 102, pumps, valves, etc.) and may operate to supply a heated or chilled fluid to AHU 106. The HVAC devices of waterside system 300 may be located within building 10 (e.g., as components of waterside system 120) or at an offsite location such as a central plant.

In FIG. 3, waterside system 300 is shown as a central plant having a plurality of subplants 302-312. Subplants 302-312 are shown to include a heater subplant 302, a heat recovery chiller subplant 304, a chiller subplant 306, a cooling tower subplant 308, a hot thermal energy storage (TES) subplant 310, and a cold thermal energy storage (TES) subplant 312. Subplants 302-312 consume resources (e.g., water, natural gas, electricity, etc.) from utilities to serve the thermal energy loads (e.g., hot water, cold water, heating, cooling, etc.) of a building or campus. For example, heater subplant 302 may be configured to heat water in a hot water loop 314 that circulates the hot water between heater subplant 302 and building 10. Chiller subplant 306 may be configured to chill water in a cold water loop 316 that circulates the cold water between chiller subplant 306 building 10. Heat recovery chiller subplant 304 may be configured to transfer heat from cold water loop 316 to hot water loop 314 to provide additional heating for the hot water and additional cooling for the cold water. Condenser water loop 318 may absorb heat from the cold water in chiller subplant 306 and reject the absorbed heat in cooling tower subplant 308 or transfer the absorbed heat to hot water loop 314. Hot TES subplant 310 and cold TES subplant 312 may store hot and cold thermal energy, respectively, for subsequent use.

Hot water loop 314 and cold water loop 316 may deliver the heated and/or chilled water to air handlers located on the rooftop of building 10 (e.g., AHU 106) or to individual floors or zones of building 10 (e.g., VAV units 116). The air handlers push air past heat exchangers (e.g., heating coils or cooling coils) through which the water flows to provide heating or cooling for the air. The heated or cooled air may be delivered to individual zones of building 10 to serve the thermal energy loads of building 10. The water then returns to subplants 302-312 to receive further heating or cooling.

Although subplants 302-312 are shown and described as heating and cooling water for circulation to a building, it is understood that any other type of working fluid (e.g., glycol, $CO_2$, etc.) may be used in place of or in addition to water to serve the thermal energy loads. In other embodiments, subplants 302-312 may provide heating and/or cooling directly to the building or campus without requiring an intermediate heat transfer fluid. These and other variations to waterside system 300 are within the teachings of the present disclosure.

Each of subplants 302-312 may include a variety of equipment configured to facilitate the functions of the subplant. For example, heater subplant 302 is shown to include a plurality of heating elements 320 (e.g., boilers, electric heaters, etc.) configured to add heat to the hot water in hot water loop 314. Heater subplant 302 is also shown to include several pumps 322 and 324 configured to circulate the hot water in hot water loop 314 and to control the flow rate of the hot water through individual heating elements 320. Chiller subplant 306 is shown to include a plurality of chillers 332 configured to remove heat from the cold water in cold water loop 316. Chiller subplant 306 is also shown to include several pumps 334 and 336 configured to circulate the cold water in cold water loop 316 and to control the flow rate of the cold water through individual chillers 332.

Heat recovery chiller subplant 304 is shown to include a plurality of heat recovery heat exchangers 326 (e.g., refrigeration circuits) configured to transfer heat from cold water loop 316 to hot water loop 314. Heat recovery chiller subplant 304 is also shown to include several pumps 328 and 330 configured to circulate the hot water and/or cold water through heat recovery heat exchangers 326 and to control the flow rate of the water through individual heat recovery heat exchangers 226. Cooling tower subplant 308 is shown to include a plurality of cooling towers 338 configured to remove heat from the condenser water in condenser water loop 318. Cooling tower subplant 308 is also shown to include several pumps 340 configured to circulate the condenser water in condenser water loop 318 and to control the flow rate of the condenser water through individual cooling towers 338.

Hot TES subplant 310 is shown to include a hot TES tank 342 configured to store the hot water for later use. Hot TES subplant 310 may also include one or more pumps or valves configured to control the flow rate of the hot water into or out of hot TES tank 342. Cold TES subplant 312 is shown to include cold TES tanks 344 configured to store the cold water for later use. Cold TES subplant 312 may also include one or more pumps or valves configured to control the flow rate of the cold water into or out of cold TES tanks 344.

In some embodiments, one or more of the pumps in waterside system 300 (e.g., pumps 322, 324, 328, 330, 334, 336, and/or 340) or pipelines in waterside system 300 include an isolation valve associated therewith. Isolation valves may be integrated with the pumps or positioned upstream or downstream of the pumps to control the fluid flows in waterside system 300. In various embodiments, waterside system 300 may include more, fewer, or different types of devices and/or subplants based on the particular configuration of waterside system 300 and the types of loads served by waterside system 300.

Figure 4:
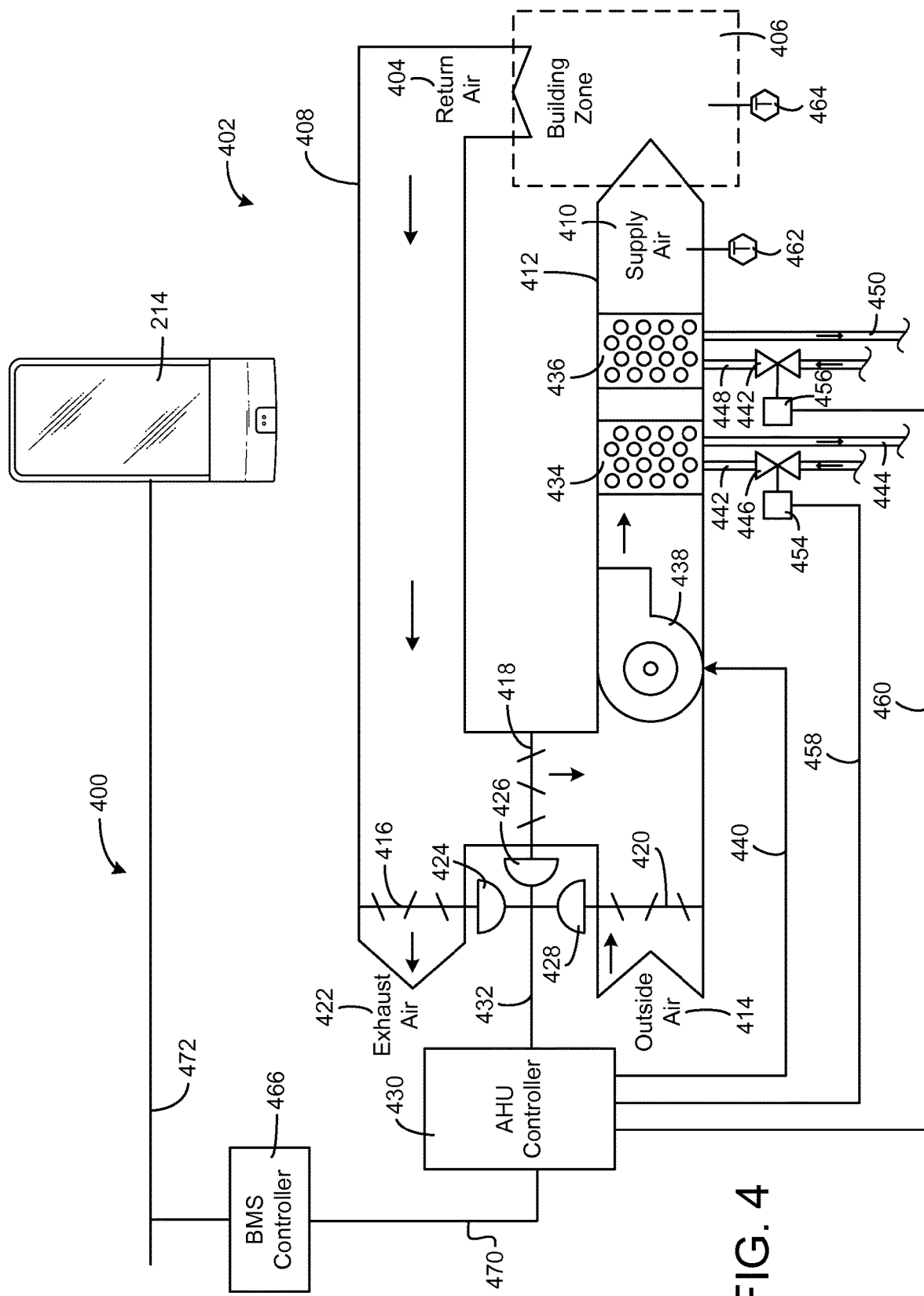
FIG. 4 is a block diagram of an airside system that may be used in conjunction with the building of FIGS. 1-2, according to an exemplary embodiment.

Referring now to FIG. 4, airside system 400 is shown to include an economizer-type air handling unit (AHU) 402. Economizer-type AHUs vary the amount of outside air and return air used by the air handling unit for heating or cooling. For example, AHU 402 may receive return air 404 from building zone 406 via return air duct 408 and may deliver supply air 410 to building zone 406 via supply air duct 412. In some embodiments, AHU 402 is a rooftop unit located on the roof of building 10 (e.g., AHU 4506 as shown in FIG. 1) or otherwise positioned to receive both return air 404 and outside air 414. AHU 402 may be configured to operate exhaust air damper 416, mixing damper 418, and outside air damper 420 to control an amount of outside air 414 and return air 404 that combine to form supply air 410. Any return air 404 that does not pass through mixing damper 418 may be exhausted from AHU 402 through exhaust damper 416 as exhaust air 422.

Each of dampers 416-420 may be operated by an actuator. For example, exhaust air damper 416 may be operated by actuator 424, mixing damper 418 may be operated by actuator 426, and outside air damper 420 may be operated by actuator 428. Actuators 424-428 may communicate with an AHU controller 430 via a communications link 432. Actuators 424-428 may receive control signals from AHU controller 430 and may provide feedback signals to AHU controller 430. Feedback signals may include, for example, an indication of a current actuator or damper position, an amount of torque or force exerted by the actuator, diagnostic information (e.g., results of diagnostic tests performed by actuators 424-428), status information, commissioning information, configuration settings, calibration data, and/or other types of information or data that may be collected, stored, or used by actuators 424-428. AHU controller 430 may be an economizer controller configured to use one or more control algorithms (e.g., state-based algorithms, extremum seeking control (ESC) algorithms, proportional-integral (PI) control algorithms, proportional-integral-derivative (PID) control algorithms, model predictive control (MPC) algorithms, feedback control algorithms, etc.) to control actuators 424-428.

Still referring to FIG. 4, AHU 402 is shown to include a cooling coil 434, a heating coil 436, and a fan 438 positioned within supply air duct 412. Fan 438 may be configured to force supply air 410 through cooling coil 434 and/or heating coil 436 and provide supply air 410 to building zone 406. AHU controller 430 may communicate with fan 438 via communications link 440 to control a flow rate of supply air 410. In some embodiments, AHU controller 430 controls an amount of heating or cooling applied to supply air 410 by modulating a speed of fan 438.

Cooling coil 434 may receive a chilled fluid from waterside system 200 (e.g., from cold water loop 316) via piping 442 and may return the chilled fluid to waterside system 200 via piping 444. Valve 446 may be positioned along piping 442 or piping 444 to control a flow rate of the chilled fluid through cooling coil 474. In some embodiments, cooling coil 434 includes multiple stages of cooling coils that can be independently activated and deactivated (e.g., by AHU controller 430, by BMS controller 466, etc.) to modulate an amount of cooling applied to supply air 410.

Heating coil 436 may receive a heated fluid from waterside system 200 (e.g., from hot water loop 314) via piping 448 and may return the heated fluid to waterside system 200 via piping 450. Valve 452 may be positioned along piping 448 or piping 450 to control a flow rate of the heated fluid through heating coil 436. In some embodiments, heating coil 436 includes multiple stages of heating coils that can be independently activated and deactivated (e.g., by AHU controller 430, by BMS controller 466, etc.) to modulate an amount of heating applied to supply air 410.

Each of valves 446 and 452 may be controlled by an actuator. For example, valve 446 may be controlled by actuator 454 and valve 452 may be controlled by actuator 456. Actuators 454-456 may communicate with AHU controller 430 via communications links 458-460. Actuators 454-456 may receive control signals from AHU controller 430 and may provide feedback signals to controller 430. In some embodiments, AHU controller 430 receives a measurement of the supply air temperature from a temperature sensor 462 positioned in supply air duct 412 (e.g., downstream of cooling coil 434 and/or heating coil 436). AHU controller 430 may also receive a measurement of the temperature of building zone 406 from a temperature sensor 464 located in building zone 406.

In some embodiments, AHU controller 430 operates valves 446 and 452 via actuators 454-456 to modulate an amount of heating or cooling provided to supply air 410 (e.g., to achieve a set point temperature for supply air 410 or to maintain the temperature of supply air 410 within a set point temperature range). The positions of valves 446 and 452 affect the amount of heating or cooling provided to supply air 410 by cooling coil 434 or heating coil 436 and may correlate with the amount of energy consumed to achieve a desired supply air temperature. AHU 430 may control the temperature of supply air 410 and/or building zone 406 by activating or deactivating coils 434-436, adjusting a speed of fan 438, or a combination of both.

Still referring to FIG. 4, airside system 400 is shown to include a building management system (BMS) controller 466 and a control device 214. BMS controller 466 may include one or more computer systems (e.g., servers, supervisory controllers, subsystem controllers, etc.) that serve as system level controllers, application or data servers, head nodes, or master controllers for airside system 400, waterside system 200, HVAC system 100, and/or other controllable systems that serve building 10. BMS controller 466 may communicate with multiple downstream building systems or subsystems (e.g., HVAC system 100, a security system, a lighting system, waterside system 200, etc.) via a communications link 470 according to like or disparate protocols (e.g., LON, BACnet, etc.). In various embodiments, AHU controller 430 and BMS controller 466 may be separate (as shown in FIG. 4) or integrated. In an integrated implementation, AHU controller 430 may be a software module configured for execution by a processor of BMS controller 466.

In some embodiments, AHU controller 430 receives information from BMS controller 466 (e.g., commands, set points, operating boundaries, etc.) and provides information to BMS controller 466 (e.g., temperature measurements, valve or actuator positions, operating statuses, diagnostics, etc.). For example, AHU controller 430 may provide BMS controller 466 with temperature measurements from temperature sensors 462-464, equipment on/off states, equipment operating capacities, and/or any other information that can be used by BMS controller 466 to monitor or control a variable state or condition within building zone 406.

Control device 214 may include one or more of the user control devices. Control device 214 may include one or more human-machine interfaces or client interfaces (e.g., graphical user interfaces, reporting interfaces, text-based computer interfaces, client-facing web services, web servers that provide pages to web clients, etc.) for controlling, viewing, or otherwise interacting with HVAC system 100, its subsystems, and/or devices. Control device 214 may be a computer workstation, a client terminal, a remote or local interface, or any other type of user interface device. Control device 214 may be a stationary terminal or a mobile device. For example, control device 214 may be a desktop computer, a computer server with a user interface, a laptop computer, a tablet, a smartphone, a PDA, or any other type of mobile or non-mobile device. Control device 214 may communicate with BMS controller 466 and/or AHU controller 430 via communications link 472.

Figure 5:
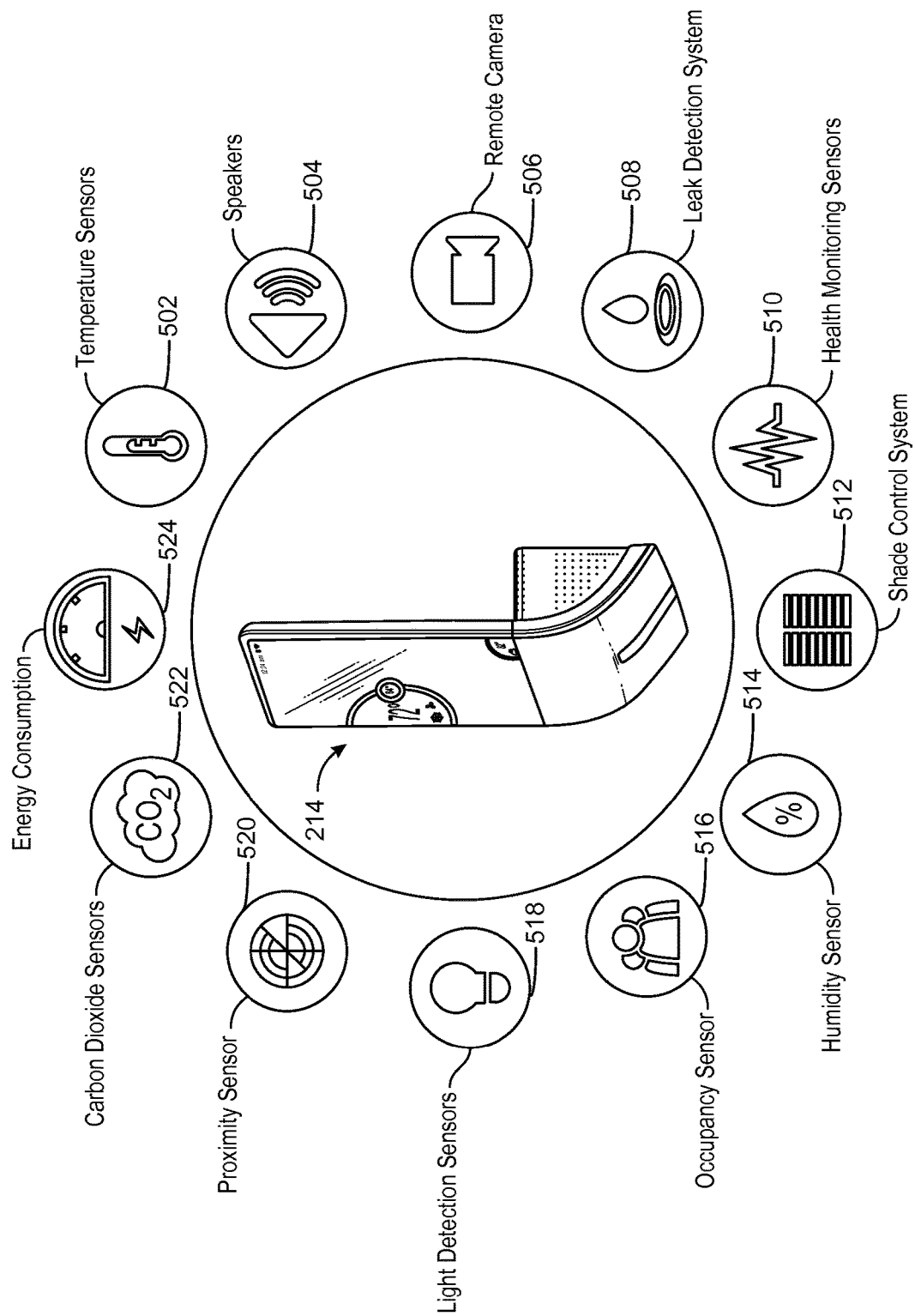
FIG. 5 is a drawing of the connections of the control device of FIG. 2 and FIG. 4, according to an exemplary embodiment.

Referring now to FIG. 5, control device 214 is shown as a connected smart hub or private area network (PAN), according to some embodiments. Control device 214 may include a variety of sensors and may be configured to communicate with a variety of external systems or devices. For example, control device 214 may include temperature sensors 502, speakers 504, leak detection system 508, health monitoring sensors 510, humidity sensors 514, occupancy sensors 516, light detection sensors 518, proximity sensor 520, carbon dioxide sensors 522, or any of a variety of other sensors. Alternatively, control device 214 may receive input from external sensors configured to measure such variables. The external sensors may not communicate over a PAN network but may communicate with control device 214 via an IP based network and/or the Internet.

In some embodiments, speakers 504 are located locally as a component of control device 214. Speakers 504 may be low power speakers used for playing audio to the immediate occupant of control device 214 and/or occupants of the zone in which control device 214 is located. In some embodiments, speakers 504 may be remote speakers connected to control device 214 via a network. In some embodiments, speakers 504 are a building audio system, an emergency alert system, and/or alarm system configured to broadcast building wide and/or zone messages or alarms.

Control device 214 may communicate with a remote camera 506, a shade control system 512, a leak detection system 508, a HVAC system, or any of a variety of other external systems or devices which may be used in a home automation system or a building automation system. Control device 214 may provide a variety of monitoring and control interfaces to allow a user to control all of the systems and devices connected to control device 214. Exemplary user interfaces and features of control device 214 are described in greater detail below.

Figure 6:
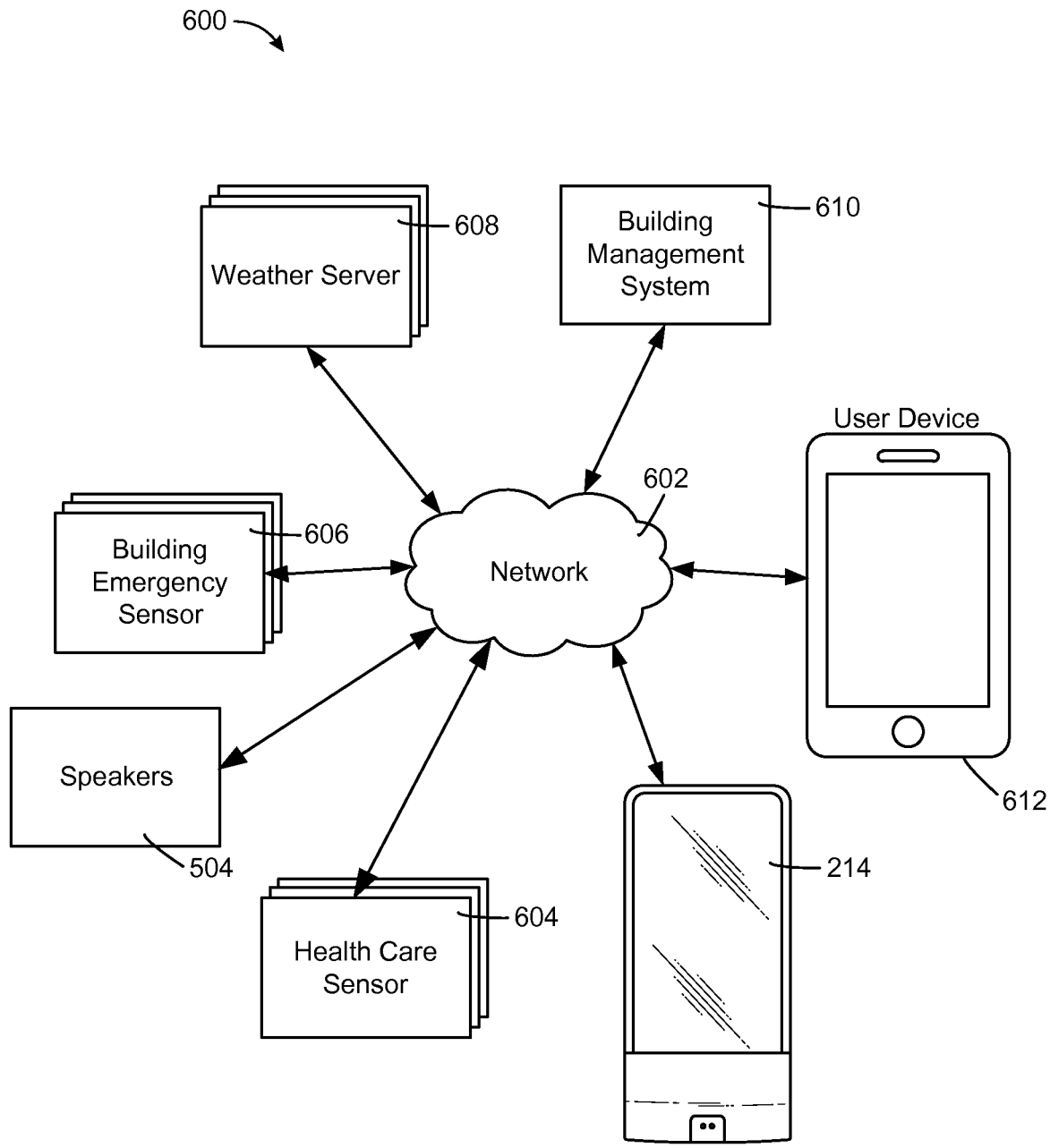
FIG. 6 is a diagram of a communications system located in the building of FIGS. 1 and 2, according to an exemplary embodiment.

Referring now to FIG. 6, a block diagram of communications system 600 is shown, according to an exemplary embodiment. System 600 can be implemented in a building (e.g. building 10) and is shown to include control device 214, network 602, healthcare sensor(s) 604, building emergency sensor(s) 606, weather server(s) 608, building management system 610, and user device 612. System 600 connects devices, systems, and servers via network 602 so that building information, HVAC controls, emergency information, navigation directions, and other information can be passed between devices (e.g., control device 214, user device 612, and/or building emergency sensor(s) 606) and servers and systems (e.g., weather server(s) 608 and/or building management system 610). In some embodiments, control device 214 is connected to speakers 504 as described with reference to FIG. 5.

In some embodiments, network 602 communicatively couples the devices, systems, and servers of system 600. In some embodiments, network 602 is at least one of and/or a combination of a Wi-Fi network, a wired Ethernet network, a Zigbee network, and a Bluetooth network. Network 602 may be a local area network or a wide area network (e.g., the Internet, a building WAN, etc.) and may use a variety of communications protocols (e.g., BACnet, IP, LON, etc.) Network 602 may include routers, modems, and/or network switches.

In some embodiments, control device 214 is configured to receive emergency information, navigation directions, occupant information, concierge information, and any other information via network 602. In some embodiments, the information is received from building management system 610 via network 602. In various embodiments, the information is received from the Internet via network 602. In some embodiments, control device 214 is at least one of or a combination of a thermostat, a humidistat, a light controller, and any other wall mounted and/or hand held device. In some embodiments, control device 214 is connected to building emergency sensor(s) 606. In some embodiments, building emergency sensor(s) 406 are sensors which detect building emergencies. Building emergency sensor(s) 406 may be smoke detectors, carbon monoxide detectors, carbon dioxide detectors (e.g., carbon dioxide sensors 522), an emergency button (e.g., emergency pull handles, panic buttons, a manual fire alarm button and/or handle, etc.) and/or any other emergency sensor. In some embodiments, the emergency sensor(s) include actuators. The actuators may be building emergency sirens and/or building audio speaker systems (e.g., speakers 504), automatic door and/or window control (e.g., shade control system 512), and any other actuator used in a building.

In some embodiments, control device 214 may be communicatively coupled to weather server(s) 608 via network 602. In some embodiments, the control device 214 may be configured to receive weather alerts (e.g., high and low daily temperature, five day forecast, thirty day forecast, etc.) from weather server(s) 608. Control device 214 may be configured to receive emergency weather alerts (e.g., flood warnings, fire warnings, thunder storm warnings, winter storm warnings, etc.). In some embodiments, control device 214 may be configured to display emergency warnings via a user interface of control device 214 when control device 214 receives an emergency weather alert from weather server(s) 608. The control device 214 may be configured to display emergency warnings based on the data received from building emergency sensor(s) 606. In some embodiments, the control device 214 may cause a siren (e.g., speakers 504 and/or building emergency sensor(s) 606) to alert occupants of the building of an emergency, cause all doors to become locked and/or unlocked, cause an advisory message be broadcast through the building, and control any other actuator or system necessary for responding to a building emergency.

In some embodiments, control device 214 is configured to communicate with building management system 610 via network 602. Control device 214 may be configured to transmit environmental setpoints (e.g., temperature setpoint, humidity setpoint, etc.) to building management system 610. In some embodiments, building management system 610 may be configured to cause zones of a building (e.g., building 10) to be controlled to the setpoint received from control device 214. In some embodiments, building management system 610 may be configured to control the lighting of a building. In some embodiments, building management system 610 may be configured to transmit emergency information to control device 214. In some embodiments, the emergency information is a notification of a shooter lockdown, a tornado warning, a flood warning, a thunderstorm warning, and/or any other warning. In some embodiments, building management system 610 is connected to various weather servers or other web servers from which building management system 610 receives emergency warning information. In various embodiments, building management system is a computing system of a hotel. Building management system 610 may keep track of hotel occupancy, may relay requests to hotel staff, and/or perform any other functions of a hotel computing system.

Control device 214 is configured to communicate with user device 612 via network 602. In some embodiments, user device 612 is a smartphone, a tablet, a laptop computer, and/or any other mobile and/or stationary computing device. In some embodiments, user device 612 communicates calendar information to control device 214. In some embodiments, the calendar information is stored and/or entered by a user into calendar application 614. In some embodiments, calendar application 614 is at least one of Outlook, Google Calendar, Fantastical, Shifts, CloudCal, DigiCal, and/or any other calendar application. In some embodiments, control device 214 receives calendar information from the calendar application such as times and locations of appointments, times and locations of meetings, and/or any other information. Control device 214 may be configured to display building map direction to a user associated with user device 612 and/or any other information.

In some embodiments, a user may press a button on a user interface of control device 214 indicating a building emergency. The user may be able to indicate the type of emergency (e.g., fire, flood, active shooter, etc.) Control device 214 may communicate an alert to building management system 610, user device 612, and any other device, system, and/or server.

In some embodiments, control device 214 is communicably coupled to healthcare sensor(s) 604 via network 602. In some embodiments, control device is configured to monitor healthcare sensor(s) 604 collecting data for occupants of a building (e.g., building 10) and determine health metrics for the occupants based on the data received from the healthcare sensor(s) 604. In some embodiments, healthcare sensor(s) 604 are one or more smart wrist bands, pacemakers, insulin pumps, and/or any other medical device. The health metrics may be determined based on heart rates, insulin levels, and/or any other biological and/or medical data.

Figure 7:
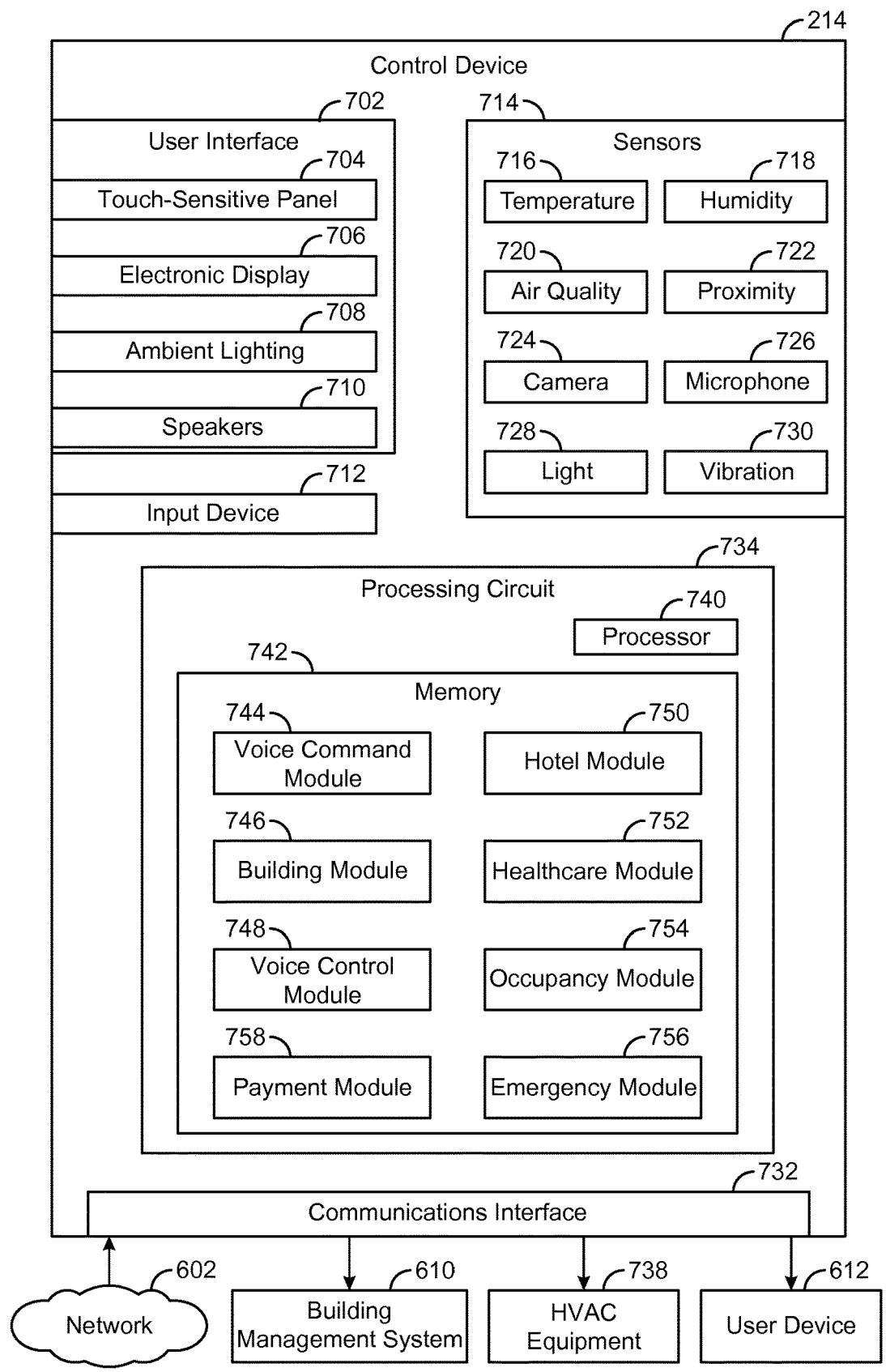
FIG. 7 is a block diagram illustrating the control device of FIGS. 2, 3, and 5 in greater detail, according to an exemplary embodiment.

Referring now to FIG. 7, a block diagram illustrating control device 214 in greater detail is shown, according to some embodiments. Control device 214 is shown to include a variety of user interface devices 702 and sensors 714. User interface devices 702 may be configured to receive input from a user and provide output to a user in various forms. For example, user interface devices 702 are shown to include electronic display 706, an electronic display 706, ambient lighting 708, speakers 710 (e.g., speakers 504), and input device 712. In some embodiments, user interface devices 702 include a microphone configured to receive voice commands from a user, a keyboard or buttons, switches, dials, or any other user-operable input devices. It is contemplated that user interface devices 702 may include any type of device configured to receive input from a user and/or provide an output to a user in any of a variety of forms (e.g., touch, text, video, graphics, audio, vibration, etc.).

Sensors 714 may be configured to measure a variable state or condition of the environment in which control device 214 is installed. For example, sensors 714 are shown to include a temperature sensor 716, a humidity sensor 718, an air quality sensor 720, a proximity sensor 722, a camera 724, a microphone 726, a light sensor 728, and a vibration sensor 730. Air quality sensor 720 may be configured to measure any of a variety of air quality variables such as oxygen level, carbon dioxide level, carbon monoxide level, allergens, pollutants, smoke, etc. Proximity sensor 722 may include one or more sensors configured to detect the presence of people or devices proximate to control device 214. For example, proximity sensor 722 may include a near-field communications (NFC) sensor, a radio frequency identification (RFID) sensor, a Bluetooth sensor, a capacitive proximity sensor, a biometric sensor, or any other sensor configured to detect the presence of a person or device. Camera 724 may include a visible light camera, a motion detector camera, an infrared camera, an ultraviolet camera, an optical sensor, or any other type of camera. Light sensor 728 may be configured to measure ambient light levels. Vibration sensor 730 may be configured to measure vibrations from earthquakes or other seismic activity at the location of control device 214.

Still referring to FIG. 7, control device 214 is shown to include a communications interface 732 and a processing circuit 734. Communications interface 732 may include wired or wireless interfaces (e.g., jacks, antennas, transmitters, receivers, transceivers, wire terminals, etc.) for conducting data communications with various systems, devices, or networks. For example, communications interface 732 may include an Ethernet card and port for sending and receiving data via an Ethernet-based communications network and/or a Wi-Fi transceiver for communicating via a wireless communications network. Communications interface 732 may be configured to communicate via local area networks or wide area networks (e.g., the Internet, a building WAN, etc.) and may use a variety of communications protocols (e.g., BACnet, IP, LON, etc.).

Communications interface 732 may include a network interface configured to facilitate electronic data communications between control device 214 and various external systems or devices (e.g., network 602, building management system 610, HVAC equipment 738, user device 612, etc.) For example, control device 214 may receive information from building management system 610 or HVAC equipment 738 indicating one or more measured states of the controlled building (e.g., temperature, humidity, electric loads, etc.) and one or more states of the HVAC equipment 738 (e.g., equipment status, power consumption, equipment availability, etc.). In some embodiments, HVAC equipment 738 may be lighting systems, building systems, actuators, chillers, heaters, and/or any other building equipment and/or system. Communications interface 732 may receive inputs from building management system 610 or HVAC equipment 738 and may provide operating parameters (e.g., on/off decisions, set points, etc.) to building management system 610 or HVAC equipment 738. The operating parameters may cause building management system 610 to activate, deactivate, or adjust a set point for various types of home equipment or building equipment in communication with control device 214.

Processing circuit 734 is shown to include a processor 740 and memory 742. Processor 740 may be a general purpose or specific purpose processor, an application specific integrated circuit (ASIC), one or more field programmable gate arrays (FPGAs), a group of processing components, or other suitable processing components. Processor 740 may be configured to execute computer code or instructions stored in memory 742 or received from other computer readable media (e.g., CDROM, network storage, a remote server, etc.).

Memory 742 may include one or more devices (e.g., memory units, memory devices, storage devices, etc.) for storing data and/or computer code for completing and/or facilitating the various processes described in the present disclosure. Memory 742 may include random access memory (RAM), read-only memory (ROM), hard drive storage, temporary storage, non-volatile memory, flash memory, optical memory, or any other suitable memory for storing software objects and/or computer instructions. Memory 742 may include database components, object code components, script components, or any other type of information structure for supporting the various activities and information structures described in the present disclosure. Memory 742 may be communicably connected to processor 740 via processing circuit 734 and may include computer code for executing (e.g., by processor 740) one or more processes described herein. For example, memory 742 is shown to include a voice command module 744, a building module 746, a voice control module 748, a payment module 758, a hotel module 750, a healthcare module 752, an occupancy module 754, and an emergency module 756. The functions of some of these modules are described in greater detail below.

In some embodiments, voice command module 744 is configured to receive audio data from microphone 726. Voice command module 744 may be configured to translate audio data into spoken words. In some embodiments, voice command module 744 may be configured to perform Internet searches based on the spoken words via network 602. In various embodiments, voice command module 744 may send requests to building management system 610 based on the spoken words.

Occupancy Tracking Features

Figure 8:
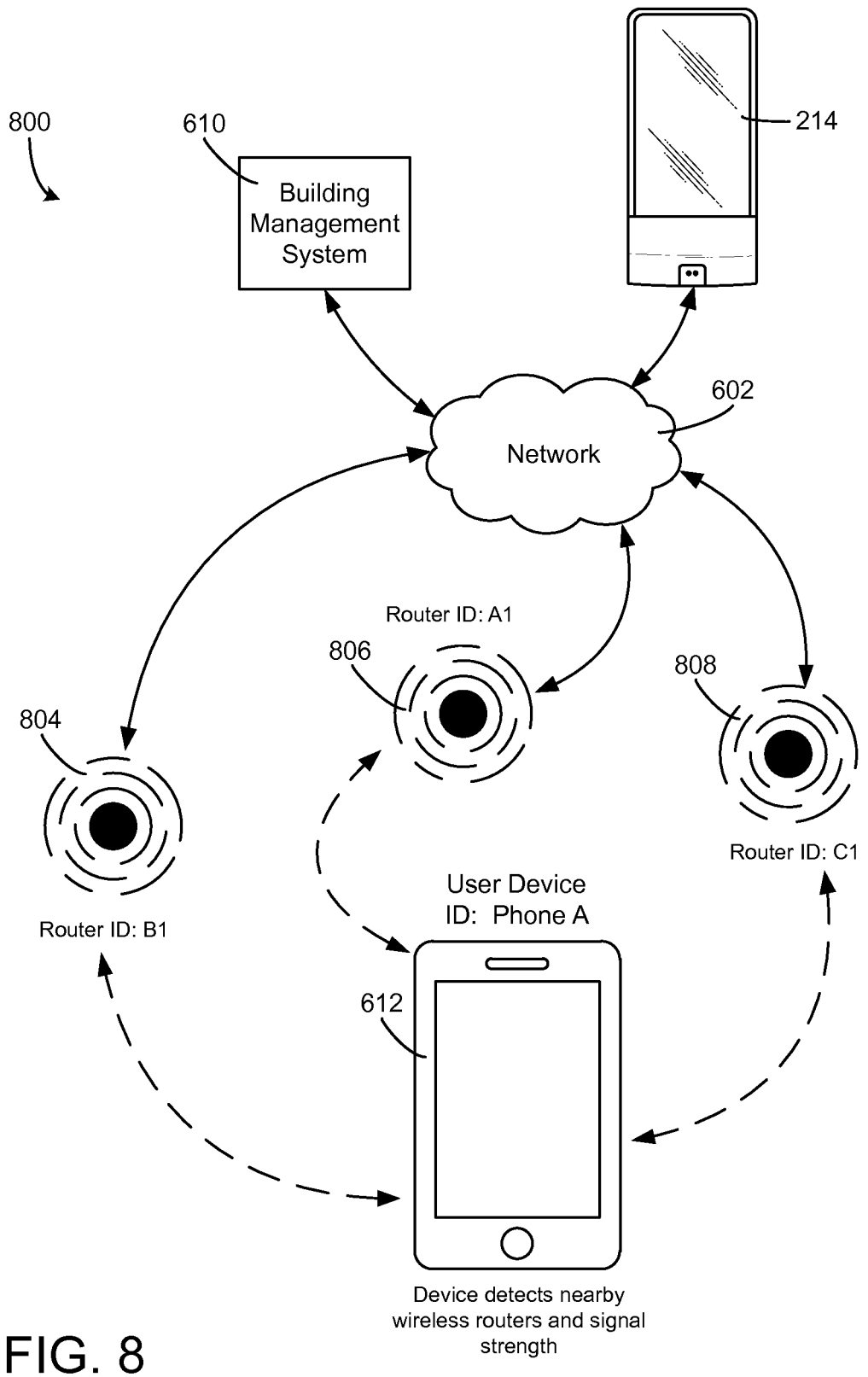
FIG. 8 is a block diagram illustrating the control device of FIG. 7 connected to three routers located in the building of FIGS. 1 and 2, according to an exemplary embodiment.

Referring now to FIG. 8, a block diagram of an occupancy tracking system 800 is shown according to an exemplary embodiment. System 800 can be implemented in a building space (e.g., building 10) to determine the occupancy of the building space based on Wi-Fi router connections and signal strengths. System 800 is shown to include building management system 610, control device 214, network 602, routers 804-808, and user device 612. In some embodiments, building management system 610 operates the building space as described in FIGS. 1-4. In various embodiments, control device 214 operates the building space as described in FIGS. 1-4. Building management system 610 is shown to be connected to control device 214 and routers 804-808. In some embodiments, network 602 is at least one of and/or a combination of a Wi-Fi network, a wired Ethernet network, a Zigbee network, and a Bluetooth network. Network 602 may be a local area network or a wide area network (e.g., the Internet, a building WAN, etc.) and may use a variety of communications protocols (e.g., BACnet, IP, LON, etc.).

Building management system 610 may include an application server. The application server may be a remote server and may be hosted at a remote location. The application server may be configured to provide a web-based presence for users and/or building administrators to access information regarding occupancy of the building. In some embodiments, the application server allows users and/or building administrators to view data pertaining to the number of users in the building space and their respective locations. The application server may communicate with user device 612 through routers 804-808 or may communicate to user device 612 via mobile data (e.g. 1G, 2G, 3G, LTE, etc.).

In some embodiments, the application server integrates a building facility web application with the determined number and location of occupants. In some embodiments, the building facility application may control room, zone, building, and campus lighting, booking, public service announcements and other features of a building facility. In some embodiments, the building facility web application may identify a user when a device associated with the user (e.g., user device 612) is detected in a room, zone, building and/or campus based on wireless signal strengths. The building facility web application may automatically login the identified user with the building web facility application. A user that has been logged in may be able to change lighting, environmental setpoints and any other adjustable building facility web application feature via user device 612. In some embodiments, the building facility web application may automatically adjust lighting and environmental setpoints to preferred settings of the identified and logged in user.

Routers 804-808 may be installed for the specific purpose of determining user occupancy or may be existing routers in a wireless building network. In some embodiments, each router may have a unique ID. In FIG. 8, router 804 has the ID B1, router 806 has the ID A1, and router 808 has the ID C1. Routers 804-808 may connect user device 612 to the Internet and/or control device 214 through network 602. Although only three routers 804-808 are shown in FIG. 8, it is contemplated that system 800 can include any number of routers located in the building space.

Routers 804-808 can be configured to emit, receive, sense, relay, or otherwise engage in unidirectional or bidirectional wireless communications. Routers 804-808 can use any type of wireless technology or communications protocol. For example, in various embodiments, the wireless emitters/receivers can be Bluetooth low energy (BLE) emitters, near field communications (NFC) devices, Wi-Fi transceivers, RFID devices, ultrawide band (UWB) devices, infrared emitters/sensors, visible light communications (VLC) devices, ultrasound devices, cellular transceivers, iBeacons, or any other type of hardware configured to facilitate wireless data communications. In some embodiments, routers 804-808 are integrated with various devices within the building (e.g., thermostats, lighting sensors, zone controllers).

Routers 804-808 can broadcast a wireless signal. The wireless signal broadcast by routers 804-808 can include the identifier associated with routers 804-808. For example, routers 804-808 can broadcast a SSID, MAC address, or other identifier which can be used to identify a particular router. In some embodiments, the wireless signal broadcast by routers 804-808 includes multiple emitter identifiers (e.g., a UUID value, a major value, a minor value, etc.). User device 612 can detect the wireless signals emitted by the routers 804-808. User device 612 can be configured to identify the router associated with the wireless signal. In some embodiments, user device 612 detects the signal strength of the wireless signals for each of routers 804-808.

In FIG. 8, user device 612 communicates with routers 804-808. User device 612 may communicate to the routers via Wi-Fi, Zigbee, Bluetooth, and/or any other wireless communication protocol. User device 612 may communicate to routers 804-808 and determine a signal strength of each router. In some embodiments, received signal strength indicator (RSSI) is determined by user device 612 for connections to each of routers 804-808. In some embodiments, user device 612 detects the RSSI of the wireless signals received from each of routers 804-808 without engaging in bidirectional communications with any of routers 804-808. For example, user device 612 can passively detect or measure RSSI without actively sending any return data to routers 804-808. In various embodiments, user device 612 determines RSSI as a percentage, in mW, in dBm, and/or in any other unit or power ratio.

User device 612 may store the location of each router 804-808 in a memory device and may determine (e.g., triangulate, estimate, etc.) the location of user device 612 based on the stored locations of routers 804-808 and the determined RSSI value for each router. In some embodiments, user device 612 is only connected to a single router or only receives a wireless signal from a single router. User device 612 may determine an approximate circular field around the single router in which user device 612 may be located based on the determined RSSI. In some embodiments, the circular field is an approximate radius such as a distance that user device 612 may be located away from the router. For example, a strong RSSI may indicate that user device 612 is close to a particular router, whereas a weaker RSSI may indicate that user device 612 is further from the router. User device 612 can use a mapping table or function to translate RSSI into distance. In some embodiments, the translation between RSSI and distance is a function of the router's broadcast power or other router settings, which user device 612 can receive from each router within broadcast range. In some embodiments, the field is a range of radii. Each radii may be different and user device 612 may be located between the two radii in a disc shaped field. In various embodiments, user device 612 triangulates the location of user device 612 based on one or more signal strengths between known locations of routers.

In various embodiments, routers 804-808 send signal strengths between routers 804-808 and user device 612 to control device 214. Control device 214 may store the location of each router 804-808 in a memory device and may determine (e.g., triangulate, estimate, etc.) the location of user device 612 based on the stored locations of routers 804-808 and the determined RSSI value for each router. In some embodiments, user device 612 is only connected to a single router or only receives a wireless signal from a single router. Control device 214 may determine an approximate circular field around the single router in which user device 612 may be located based on the determined RSSI. In some embodiments, the circular field is an approximate radius such as a distance that user device 612 may be located away from the router. For example, a strong RSSI may indicate that user device 612 is close to a particular router, whereas a weaker RSSI may indicate that user device 612 is further from the router. Control device 214 can use a mapping table or function to translate RSSI into distance. In some embodiments, the translation between RSSI and distance is a function of the router's broadcast power or other router settings, which control device 214 can receive from each router within broadcast range. In some embodiments, the field is a range of radii. Each radii may be different and user device 612 may be located between the two radii in a disc shaped field. In various embodiments, control device 214 triangulates the location of user device 612 based on one or more signal strengths between known locations of routers.

Still referring to FIG. 8, user device 612 may communicate with building management system 610, an application server, and/or control device 214 via the routers 804-808. In some embodiments, user device 612 sends its location within the building space to building management system 610, an application server, and/or control device 214. In some embodiments, user device 612 sends a unique ID to building management system 610 and/or an application server. In FIG. 8, the unique ID of user device 612 is Phone A. In some embodiments, building management system 610 is configured to run a unique heating or cooling schedule based on the ID of the user device 612. For example, an environmental setpoint may be tied to the ID of user device 612. Building management system 610 may be configured to adjust the setpoint of the zone in which user device 612 is located to the environmental setpoint tied to the ID of user device 612.

Figure 9:
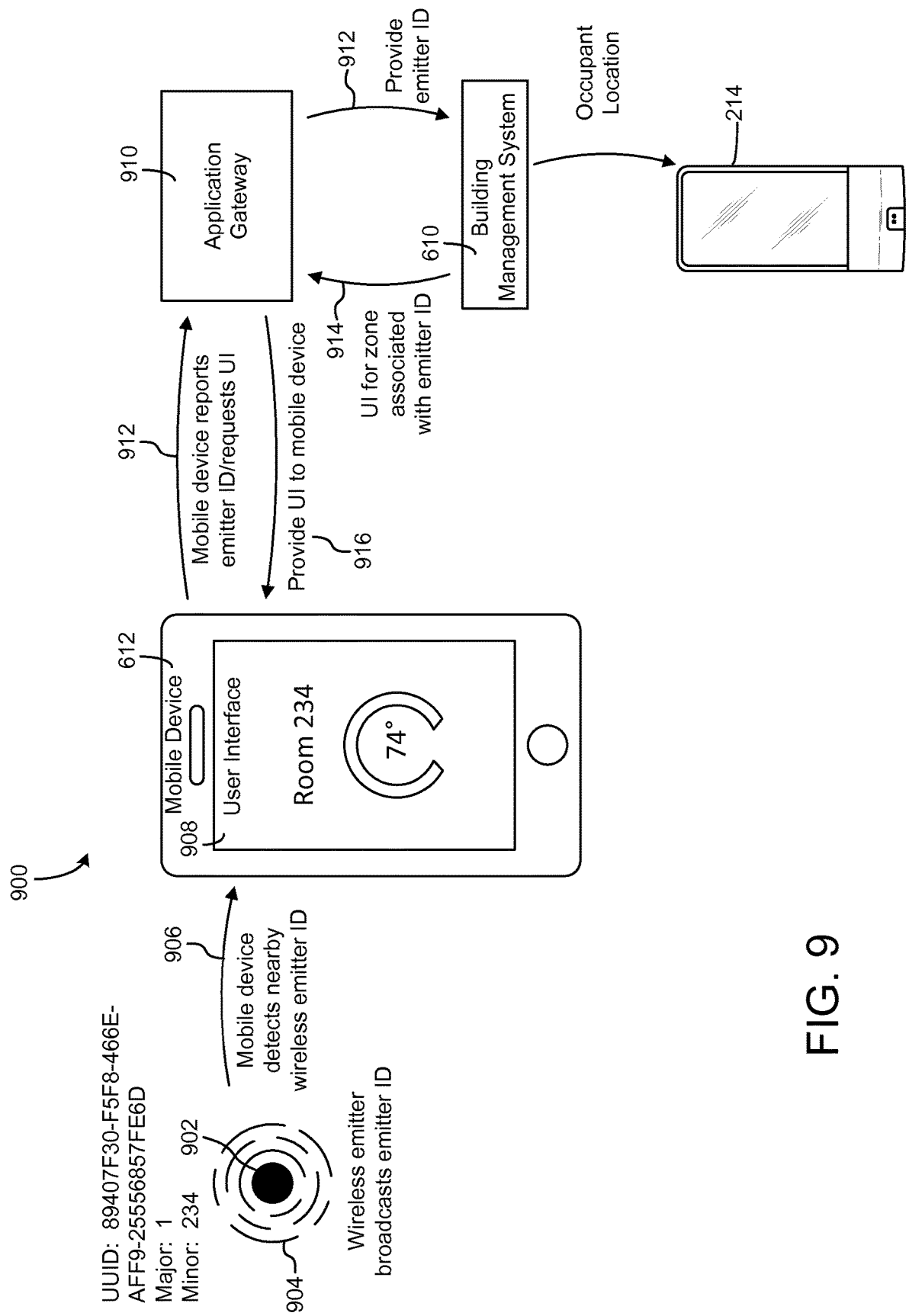
FIG. 9 is a flow diagram illustrating a process for determining the location of a mobile device in the building of FIG. 1 using the plurality of wireless emitters, according to an exemplary embodiment.

Referring now to FIG. 9, a flow diagram illustrating a process 900 for using occupant location in a building is shown, according to an exemplary embodiment. A building (e.g., building 10) is equipped with a plurality of wireless emitters 902. Each of wireless emitters 902 may be located at a different position in the building and may be associated with a different emitter identifier. Although only one wireless emitter 902 is shown in FIG. 9, many wireless emitters 902 may be placed at various locations in or around the building. Each of wireless emitters 902 broadcasts a wireless signal (step 904). The wireless signal broadcast by emitter 902 includes an indication of an emitter identifier associated with wireless emitter 902. In some embodiments, the wireless signal broadcast by emitter 902 include multiple emitter identifiers (e.g., a UUID value, a major value, a minor value, etc.).

Still referring to FIG. 9, a user device 612 detects the wireless signal emitted by wireless emitter 902 (step 906). User device 612 may be, for example, a laptop computer, a tablet, a smart phone, a RFID sensor, a Bluetooth device, a Wi-Fi device, a NFC device, a portable communications device, or any combination thereof. User device 612 may be configured to run remote applications 908 and may function as a UI client. User device 612 may be configured (e.g., by an application running on user device 612) to identify the emitter identifier associated with the wireless signal detected in step 906.

In FIG. 9, user device 612 is shown connecting to an application gateway 910 (e.g., at a predefined IP address, via a wireless data connection) and reporting the emitter identifier associated with the detected wireless signal (step 912). In some embodiments, user device 612 requests a user interface for presentation on user device 612. The request may include the emitter identifier detected by user device 612 and/or a device identifier associated with user device 612. Application gateway 910 may provide the emitter identifier and/or the device identifier to building management system 610. In various embodiments, application gateway 910 and building management system 610 may be combined into a single component or user device 612 may report the emitter identifier directly to building management system 610.

Building management system 610 uses the emitter identifier and/or the device identifier to select a user interface for presentation on user device 612. Building management system 610 may select the user interface for a building zone associated with the emitter identifier reported by user device 612. For example, building management system 610 may select a user interface which includes information and/or control options relating to the building zone associated with the reported emitter identifier. In some embodiments, building management system 610 selects a user interface based on the identity of a user associated with user device 612 (e.g., based on a user identifier or device identifier reported by user device 612). In some embodiments, building management system 610 uses emitter identifier reported by user device 612 to determine the position of user device 612 within the building. Building management system 610 may send the position of user device 612 to control device 214. Building management system 610 may select a user interface for monitoring and/or controlling the building zone in which user device 612 is currently located or a building zone in which user device 612 has been located previously.

Still referring to FIG. 9, building management system 610 is shown providing the selected user interface to application gateway 910 (step 914), which provides the selected user interface to user device 612 (step 916). In other embodiments, BMS controller 12 may provide the selected user interface directly to user device 612. User device 612 may present the selected user interface on a user interface of user device 612. The user interface may be, for example, an electronic display or other user interface element of user device 612. Advantageously, building management system 610 may automatically detect the location of user device 612 and deliver a location-specific user interface to user device 612 without requiring a user to input location information.

Figure 10:
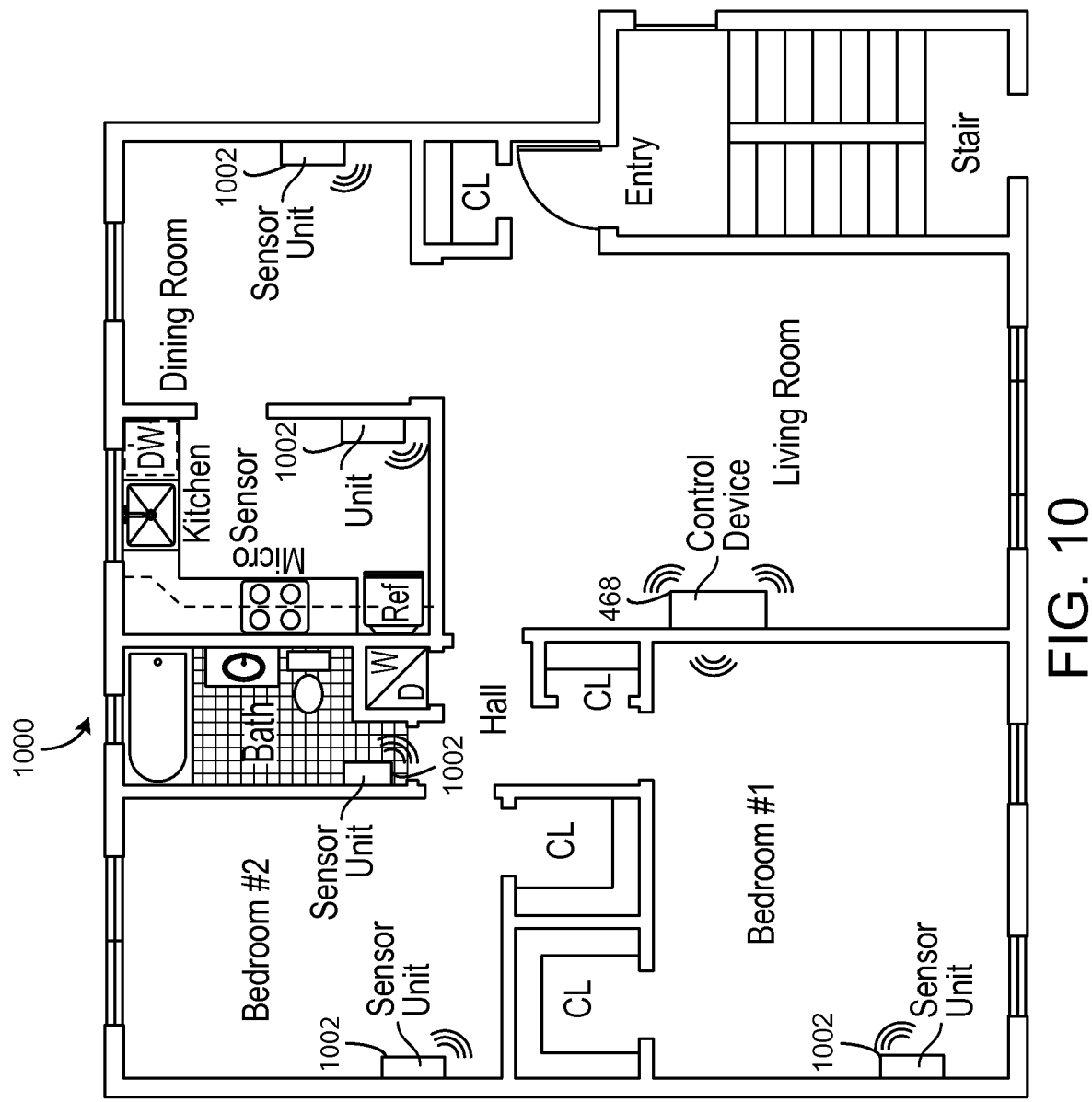
FIG. 10 is a drawing of a floorplan of a building with a main control unit in one room and sensor units in other rooms, according to an exemplary embodiment.

Referring now to FIG. 10, a floorplan 1000 of a home and/or building is shown. The home is shown to include several different zones (e.g., rooms or areas) including a living room, a first bedroom, a second bedroom, a bathroom, a kitchen, and a dining room. A control device 214 may be installed in one of the rooms or zones. For example, FIG. 10 shows a main control unit (e.g., control device 214) installed in the living room. The main control unit may serve as a central hub for monitoring environmental conditions, controlling various devices throughout the home, and/or tracking occupancy through multiple rooms and/or zones of the home.

Sensor units 1002 (e.g., proximity sensor 520, remote camera 506, occupancy sensor 516, routers 804-808, emitter 902, etc.) may be installed in various rooms or zones in the home. For example, FIG. 10 shows a sensor unit installed in each of the bedrooms, the bathroom, the kitchen, and the dining room. In some embodiments, the sensors 1002 measure signals strengths between user devices (e.g., user device 612). In various embodiments, sensors 1002 are configured to relay image data and/or audio data to control device 214. Control device 214 may identify occupants based on the image and/or audio data. The measured signal strengths may be used to determine the occupancy of the owner of the user device.

In some embodiments, a building management system and/or control device 214 determines the location of the user device. The sensor units 1002 may be configured to measure environmental conditions within each room or zone and to receive user input (e.g., voice commands via a microphone). For example, each sensor unit 1002 may include a plurality of sensors (e.g., a temperature sensor, a humidity sensor, a smoke detector, a light sensor, a camera, a motion sensor etc.) configured to measure variables such as temperature, humidity, light, etc. in the room or zone in which the sensor unit is installed. The sensor units 1002 may communicate (e.g., wirelessly or via a wired communications link) with the control device 214 and/or with each other. In some embodiments, sensors, such as low power door sensors, can communicate with repeaters disposed in the gang boxes or other locations using a low power overhead protocol. The repeaters can provide wired or wireless communication to the main control unit.

Figure 11:
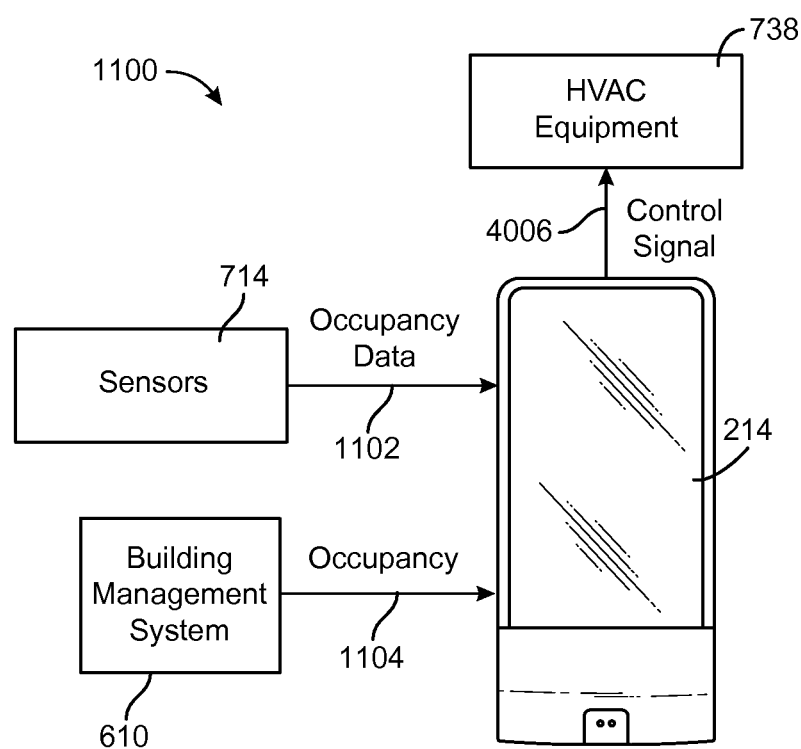
FIG. 11 is a diagram illustrating the control device of FIG. 7 receiving occupancy data, according to an exemplary embodiment.

Referring now to FIG. 11, a diagram of control device 214 receiving occupancy information is shown, according to an exemplary embodiment. In some embodiments, control device 214 is configured to receive occupancy data 1102 from sensors 714. In some embodiments, sensors 714 are at least one or a combination of camera 724, microphone 726, a motion sensor (e.g., proximity 722), and/or any other occupancy sensor. In some embodiments, occupancy module 754 may be configured to process the occupancy data to determine the identity of any detected occupants.

In some embodiments, occupancy module 754 may be configured to determine the identity of an occupant based on occupancy data 1102 received from sensors 714. In some embodiments, the occupancy module 754 receives sensor input from sensors 714 where the sensors may include camera 724. Occupancy module 754 can perform digital image processing to identify the one or more users based on the digital images received from camera 724. In some embodiments, digital image processing is used to identify the faces of the one or more users, the height of the one or more users, or any other physical characteristic of the one or more users. In some embodiments, the digital image processing is performed by image analysis tools such as edge detectors and neural networks. In some embodiments, the digital image processing compares the physical characteristics of the one or more users with physical characteristics of previously identified users.

In some embodiments, the occupancy module 754 receives sensor input from microphone 726. Microphone 726 can be any of a plurality of microphone types. The microphone types include, for example, a dynamic microphone, a ribbon microphone, a carbon microphone, a piezoelectric microphone, a fiber optic microphone, a laser microphone, a liquid microphone, and an audio speaker used as a microphone. In some embodiments, the occupancy controller analyzes the audio data received from the microphone. In some embodiments, the occupancy controller 636 identifies one or more users based on voice biometrics of the audio received from microphone 726. Voice biometrics are the unique characteristics of a speaker's voice. Voice biometrics include voice pitch or speaking style that result from the anatomy of the speaker's throat and/or mouth. In some embodiments, the occupancy module 754 uses a text dependent voice recognition technique. In some embodiments, the occupancy module 754 uses a text independent voice recognition technique to identify the one or more users. Occupancy module 754 may be configured to store voice biometrics linked to individuals. Occupancy module 754 may be configured to match the stored voice biometrics to voice biometrics determined for occupants.

In some embodiments, the occupancy module 754 uses the text dependent voice recognition technique to identify the one or more users based on a password or particular phrase spoken by one of the users. For example, the user may speak a phrase such as "This is Felix, I am home." The occupancy module 754 can perform speech recognition to determine the spoken phrase "This is Felix, I am home" from the audio data received from the microphone. In some embodiments, occupancy module 754 uses one or a combination of a hidden Markov models, dynamic time warping, and a neural networks to determine the spoken phrase. Occupancy module 754 compares the determined spoken phrase to phrases linked to users. If the phrase, "This is Felix, I am home" matches a phrase linked to a user Felix, the occupancy controller identifies the user as Felix.

In some embodiments, occupancy module 754 uses the text independent voice recognition technique to identify one or more users based on particular voice biometrics of the user. The text independent voice recognition technique performs a pattern recognition technique to identify the particular voice biometrics of the speaker from the audio data received from the microphone. The voice biometrics include voice pitch and speaking style. In some embodiments, a plurality of techniques are used to identify the voice biometrics of the user. The techniques include frequency estimation, hidden Markov models, Gaussian mixture models, pattern matching algorithms, neural networks, matrix representation, Vector Quantization, and decision trees.

In some embodiments, the occupancy module 754 is configured to capture audio data from one or more users and perform pre-processing. In some embodiments pre-processing may be compressing the audio data, converting the audio data into an appropriate format, and any other pre-processing action necessary. The occupancy module 754 may be configured to transmit the captured spoken audio data to a voice recognition server via communications interface 732 and network 602 as described with reference to FIGS. 6-7. The voice recognition server (e.g., building management system 610) may be configured to determine the identity of the occupant and transmit the identity of the occupant to occupancy module 754.

Still referring to FIG. 11, control device 214 is configured to receive occupancy information 1104 from building management system 610. In some embodiments, building management system 610 may be configured to determine the location of a user based on trilateration methods as described with reference to FIG. 8. In various embodiments, building management system 610 may be configured to determine the location of a user based on signal strength to an emitter as described with reference to FIG. 9.

The building management system 610 may send the identity of the occupant and the location of the occupant in a building (e.g., building 10). In some embodiments, control device 214 is configured to cause zones and/or buildings to be controlled to environmental conditions (e.g., temperature setpoint, humidity setpoint, etc.) based on environmental condition preferences and location of the occupant. The control device 214 may be configured to generate control signals for HVAC equipment 738 to achieve the preferred environmental conditions. In various embodiments, the control device 214 may be configured to play music in different zones and/or cause a music platform (e.g., Pandora, Spotify, etc.) to play music preferences of the identified user in the zone and/or building which the user is located.

Figure 12:
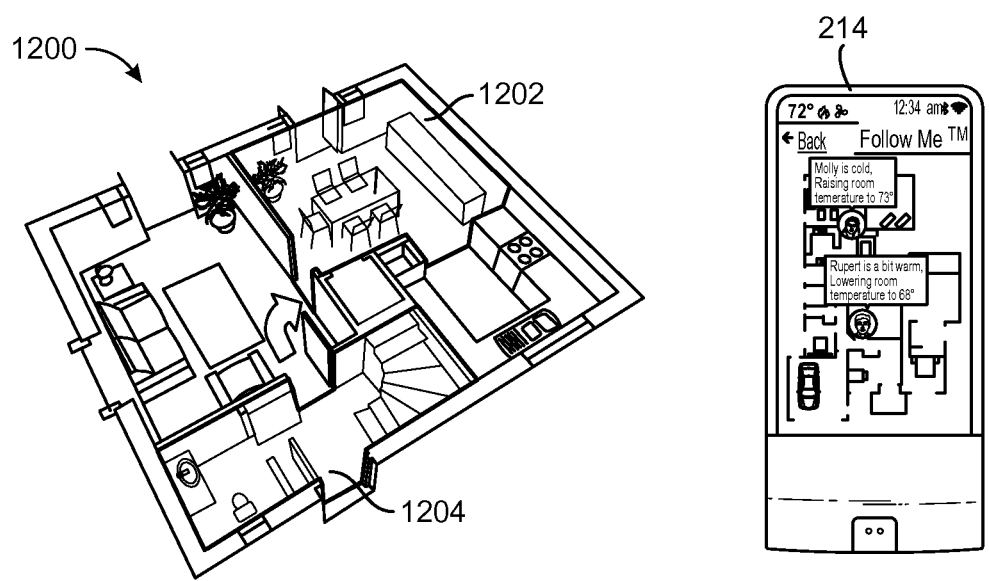
FIG. 12 is a drawing of a building space and an occupant tracking application on the control device of FIG. 7, according to an exemplary embodiment.
Figure 13:
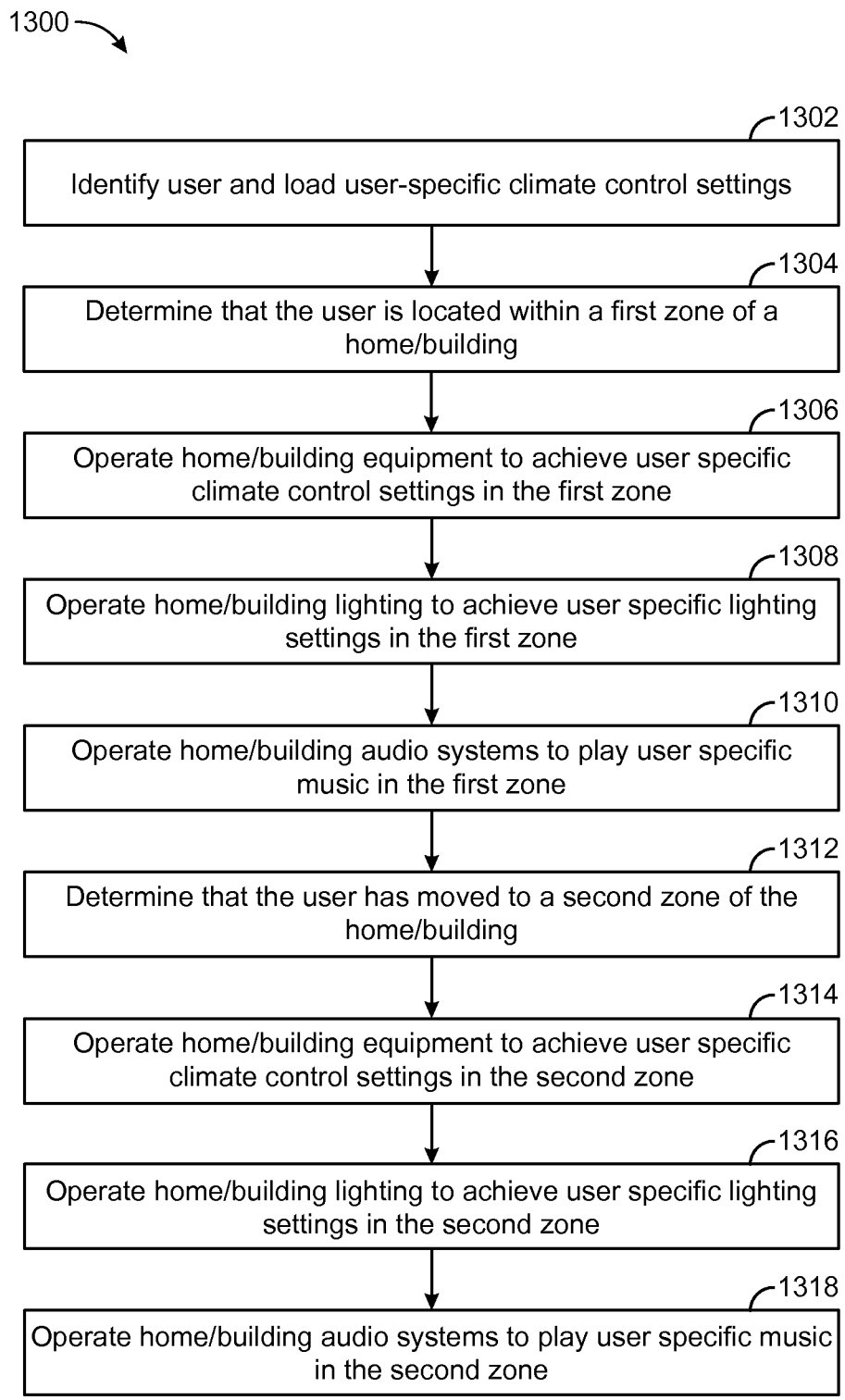
FIG. 13 is a flowchart of operations for controlling zones of a building with the control device of FIG. 11, according to an exemplary embodiment.

Referring now to FIGS. 12-13, a diagram 1200 and flowchart 1300 illustrating a process for controlling a building zone based on detected occupancy is shown, according to an exemplary embodiment. In some embodiments, the process is performed by occupancy module 754, as described with reference to FIG. 7. Control device 214 may identify a user and load user-specific climate control settings for the identified user (step 1302). In some embodiments, control device 214 identifies the user by communicating with a portable device carried by the user (e.g., a phone, a RFID card, a NFC tag, etc.). In other embodiments, the user is identified by voice (FIG. 11), by appearance (FIG. 11), trilateration of wireless signals from a user device (FIG. 8), communicating with wireless emitters via a user device (FIG. 9) or any other data collected by sensors in zones 1202 and 1204. Control device 214 may determine that the user is located within a first zone 1202 of a home or building (step 1304) and may operate home/building equipment to achieve the user-specific climate control settings in the first zone 1202 (step 1306). Control device 214 may turn the lights on in zone 1202 (step 1308). In some embodiments, the lights are dimmed to user specified levels. Control device 214 may be configured to operating music played in zones 1202 when the user is identified (step 1310). In some embodiments, the user is linked to specific songs, playlists, and/or volumes. Control device 214 may be configured to cause audio systems to play certain playlists and/or radios in zone 1202 when the user is identified in zone 1202.

Control device 214 may determine that the user has moved to a second zone 1204 of the home/building (step 1308) and may operate the home/building equipment to achieve the user-specific climate control settings in the second zone 1204 (step 1310). In some embodiments, control device 214 is configured to operate the lighting of zones 1202 and 1204 based upon the location of the user (step 1312). For example, control device 214 may turn off lights in zone 1202 and on in zone 1204 when the user moves from zone 1202 to zone 1204 (step 1316). Control device 214 may be configured to operating music played in zones 1202 and 1204 when the user moves from zone 1202 to 1204 (step 1316). For example, when the user moves to zone 1204, the music may stop playing in zone 1202 and being playing in 1204 (step 1318).

Figure 14A:
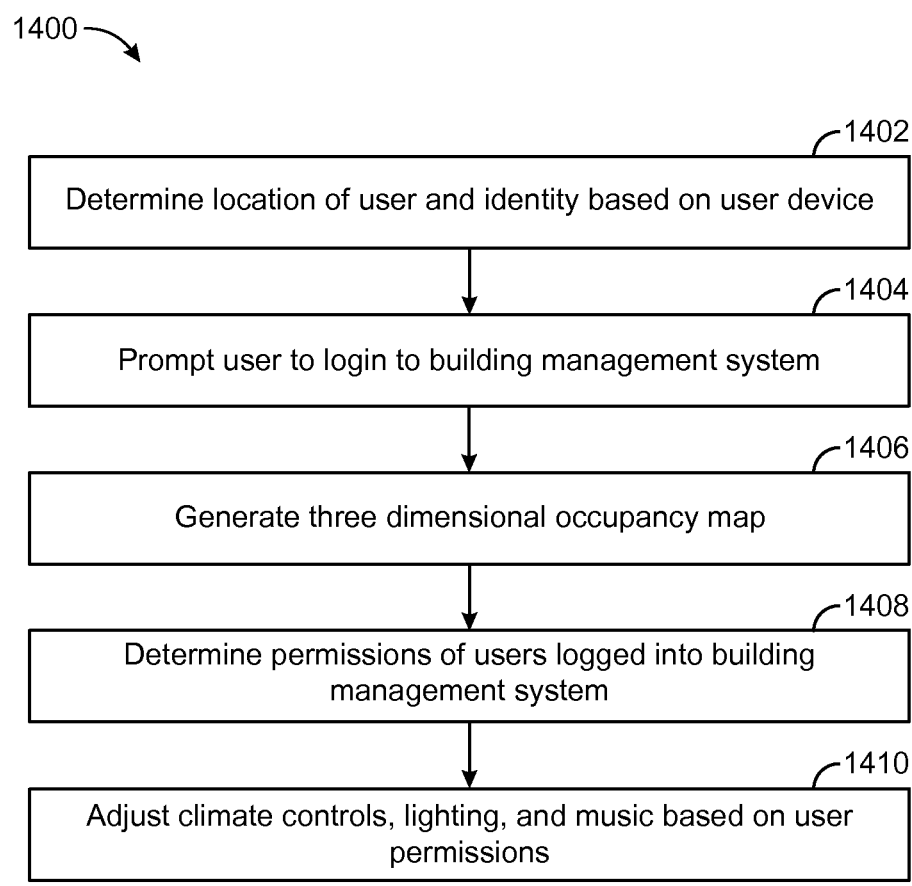
FIG. 14A is a flowchart of operations for controlling zones of a building with the control device of FIG. 11, according to an exemplary embodiment.

Referring now to FIG. 14A, a flowchart 1400 illustrating a building control process which may be performed by occupancy module 754 of control device 214 as described with reference to FIG. 7, according to an exemplary embodiment. In some embodiments, control device 214 is configured to determine the location and identity of a user based on wireless communication (step 1402) with user device 612 when user device 612 is associated with the user. In some embodiments, wireless triangulation is used to determine the location of the user based on signal strengths between user device 612 and routers and/or emitters as described with reference to FIGS. 8-9.

In some embodiments, a unique device identifier (e.g., a serial number, a hardware ID, a MAC address, etc.) may link user device 612 to a particular user profile. When user device 612 is determined to be in the building (e.g., building 10) the user may receive a command to authenticate (i.e., log in) with building management system 610 via user device 612 (step 1404). In some embodiments, user device 612 automatically authenticated with the building management system 610 based on a unique device identifier. In some embodiments, the authentication is performed directly between the user device and the building management system 610. In various embodiments, control device 214 receives the unique device identifier from the user device and facilitates the authentication with building management system 610. In various embodiments, the user may be prompted to enter a user name and password via user device 612 and/or user interface 702 of display device 214 to authenticate with the building management system 610.

In some embodiments, the building management system 610 may be configured to generate a three dimensional building map with the location and identity of multiple building occupants located on the map (step 1406). The building map may contain multiple floors, zones, buildings, and/or campuses. In some embodiments, the three dimensional building map may be accessible via a user device (e.g., user device 612) if the user device has the proper permissions to view the building map. In some embodiments, the user device must be associated with a technician, and/or any other building employee for the user to have access to the three dimensional building map.

In some embodiments, building management system 610 keeps a record of various occupants of the building and associated permissions with each occupant. In some embodiments, the permissions are music permission (i.e., if the user can change music, radio stations, volume, etc. of the music played in various zones of the building). In some embodiments, the permissions allow a user to change music, radio stations, music volume, environmental setpoints, lighting and/or any other adjustable setting of control device 214 via user interface 702, microphone 726, and/or user device 612 associated with the user. In some embodiments, the permissions to change and/or adjust environmental conditions (e.g., temperature setpoint, humidity setpoint, etc.) (step 1408). Based on the permissions and user preferences, the building management system 610 may be configured to send commands to the devices (e.g., control device 214) to adjust environmental zone conditions, lighting, and music of zones (step 1410).

Referring now to FIG. 14B, table 1412 of occupant permissions and preferences is shown, according to an exemplary embodiment. In some embodiments, the table may be permissions and preferences which control device 214 receives from building management system 610 as described with reference to FIG. 11 and/or FIG. 14A. In some embodiments, table 1412 contains permissions and preferences for occupant A 1414, occupant B 1416, and occupant C 1418. Permissions and preferences for any number of occupants may be received from building management system 610 and/or stored on control device 214. Occupant A 1414, occupant B 1416, and occupant C 1418 may have preferred preferences such as preferred setpoint 1420, music 1422, lighting 1424, and shades/blinds 1426. Occupant A 1414, occupant B 1416, and occupant C 1418 may have permissions to change and/or operate certain features of control device 214 (i.e., setpoints, music, lighting, etc.) Any number of permissions and/or preferences may be received from building management system 610 for occupant A 1414, occupant B 1416, and occupant C 1418.

Occupant A 1414 has a preferred setpoint of 78 degrees F., occupant B 1416 has a preferred setpoint of 75 degrees F. and occupant C 1418 has no permission to change the setpoint. In some embodiments, when an occupant with a preferred setpoint moves from a first zone to a second zone, the preferred setpoint may follow the occupant and the second zone may be heated and/or cooled to the preferred setpoint. An occupant with no permission to change a setpoint (e.g., occupant C 1418) may not be able to make any changes to the setpoint.

In some embodiments, control device 214 may disable changes to the setpoint whenever occupant C 1418 is determined to be a set distances from control device 214. In some embodiments, control device 214 may disable changes to the lighting whenever occupant C 1418 is identified in the zone that control device 214 is located. In some embodiments, when occupant C 1418 is authenticated and/or logged in with the building management system and/or control device 214 as described with reference to FIG. 14A, occupant C 1418 may be notified via a user device (e.g., user device 612) that occupant C 1418 is unable to change the setpoint. In some embodiments, occupant C 1418 is notified via the user interface 702 (e.g., through images on electronic display 706, audio from speakers 710, etc.) that occupant C 1418 does not have permission to adjust the setpoint.

Occupant A 1414, occupant B 1416, and occupant C 1418 may have permissions and preferences for music 1422 such as the music played in zones of a building (e.g., building 10). In table 1412, occupant A 1414 has a preference for no music, occupant B 1416 has a preferred radio station, and occupant C 1418 does not have permission to play music. In some embodiments, whenever occupant B 1416 is in a zone, the building equipment in that zone may automatically play radio station AM 1130. In some embodiments, when occupant A 1414 enters a zone, the building equipment in that zone will automatically turn off any music that is playing. In some embodiments, any attempt by occupant C 1418 to play music and/or audio will be met by a notification that occupant C 1418 does not have the appropriate permissions to change the music and/or audio.

In some embodiments, control device 214 may disable changes to music preferences whenever occupant C 1418 is determined to be a set distances from control device 214. In some embodiments, control device 214 may disable changes to the lighting whenever occupant C 1418 is identified in the zone that control device 214 is located. In some embodiments, when occupant C 1418 is authenticated and/or logged in with building management system 610 and/or control device 214 via a user device (e.g., user device 612) as described with reference to FIG. 14B, occupant C 1418 may be notified via a user device (e.g., user device 612) that occupant C 1418 is unable to change the music preferences. In some embodiments, occupant C 1418 is notified via the user interface 702 (e.g., through images on electronic display 706, audio from speakers 710, etc.) that occupant C 1418 does not have permission to adjust the music preferences.

Occupant A 1414, occupant B 1416, and occupant C 1418 may have permissions and preferences for lighting 1424. In some embodiments, the lighting in zones and/or a building (e.g., building 10) may be adjusted based on permissions and preferences of occupant A 1414, occupant B 1416, and occupant C 1418. Occupant A 1414 may have no permission to change lighting. Occupant B 1416 may have a preference for lighting in the zone which occupant B occupies to be dim. Occupant C 1418 may have the preference that the lighting associated with the zone which occupant C 1418 occupies be at full brightness.

In some embodiments, control device 214 may disable changes to the lighting whenever occupant A 1414 is determined to be a set distances from control device 214. In some embodiments, control device 214 may disable changes to the lighting whenever occupant A 1414 is identified in the zone that control device 214 is located. In some embodiments, when occupant A 1414 is authenticated and/or logged in with building management system 610 and/or control device 214 via a user device (e.g., user device 612) as described with reference to FIG. 14A, occupant A 1414 may not have the ability to change the lighting settings of control device 214 and may be notified via a user device (e.g., user device 612) that occupant A 1414 is unable to change the lighting settings. In some embodiments, occupant A 1414 is notified via the user interface 702 (e.g., through images on electronic display 706, audio from speakers 710, etc.) that occupant A 1414 does not have permission to adjust the lighting settings.

Occupant A 1414, occupant B 1416, and occupant C 1418 may have permissions and preferences for shades/blinds 1426. In some embodiments, occupant A 1414 has the preference that natural light be used to illuminate the zone which occupant A 1414 occupies whenever possible. Using natural light may include opening shades, opening blinds, and/or opening shutters. Occupant B 1416 and occupant C 1418 may have no permission to open and/or close shades, blinds, and/or shutters. Any attempt by occupants B 1416 and occupant C 1418 to open and/or close shades, blinds, and/or shutters controlled by control device 214 may be met with a notification that occupants A 1416 and/or occupant C 1418 may not have the proper permission to open and/or close the shades, blinds, and/or shutters.

In some embodiments, control device 214 may disable changes to the shades and/or blinds whenever occupants B 1416 and/or occupant C 1418 are determined to be a set distance from control device 214. In some embodiments, control device 214 may disable changes to the shades and/or blinds whenever occupants B 1416 and/or occupant C 1418 are identified in the zone which control device 214 is located. In some embodiments, when occupants B 1416 and/or occupant C 1418 are authenticated with building management system 610 and/or control device 214 via a user device (e.g., user device 612) as described with reference to FIG. 14A, occupants B 1416 and/or occupant C 1418 may be notified via a user device (e.g., user device 612) that occupants B 1416 and/or occupant C 1418 are unable to change the shades and/or blinds. In some embodiments, occupants B 1416 and/or occupant C 1418 are notified via the user interface 702 (e.g., through images on electronic display 706, audio from speakers 710, etc.) that occupants B 1416 and/or occupant C 1418 do not have permission to adjust the shades and/or blinds.

Display and Emergency Features

Figure 15:
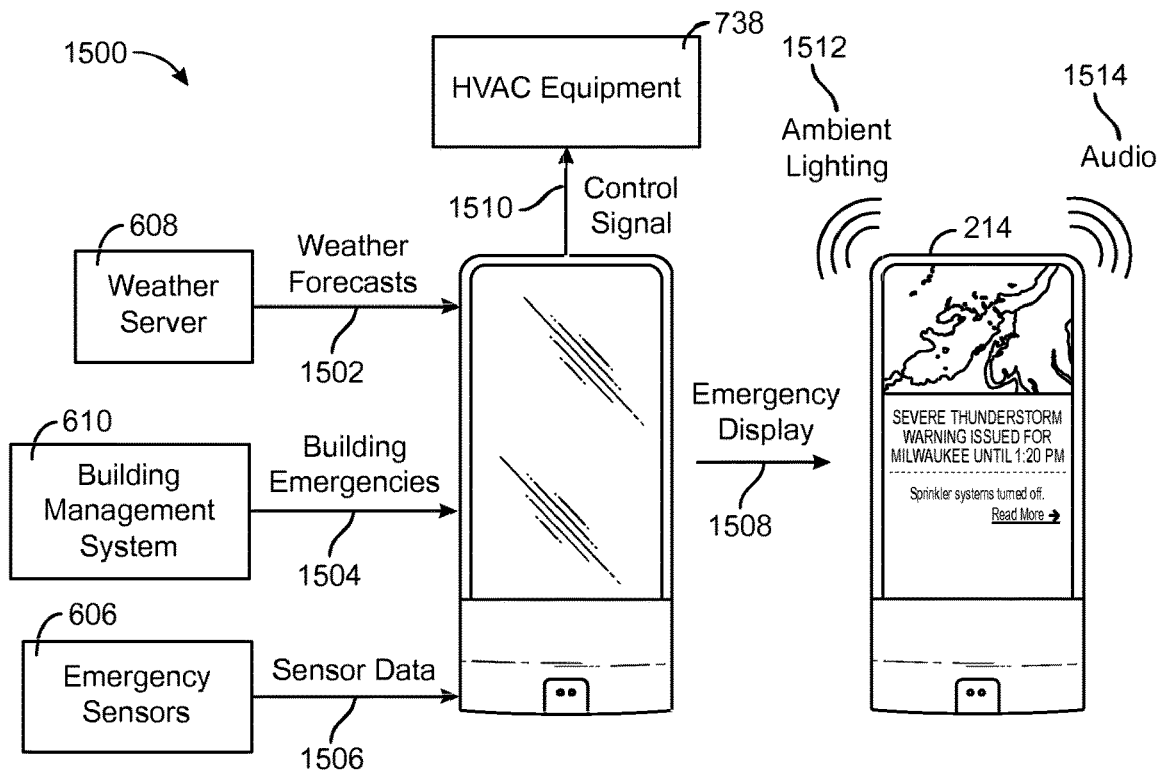
FIG. 15 is a diagram of the control device of FIG. 7 receiving emergency weather notifications, according to an exemplary embodiment.
Figure 16A:
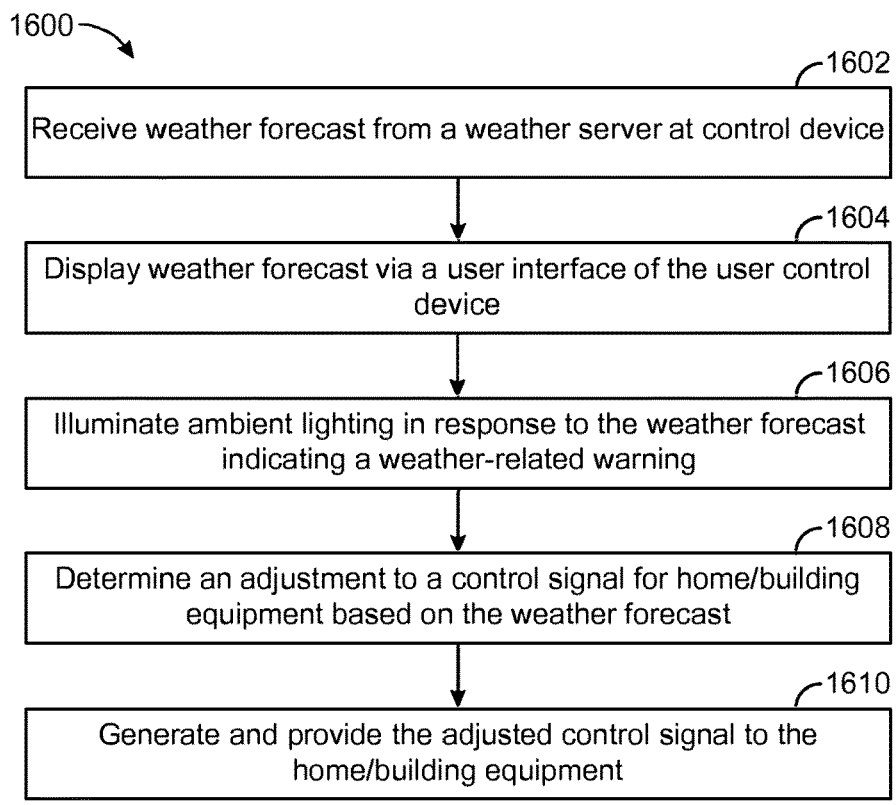
FIG. 16A is a flowchart of operations for receiving emergency information with the control device of FIG. 7, according to an exemplary embodiment.

Referring now to FIGS. 15 and 16A, a diagram 1500 and flowchart 1600 illustrating a control process which may be performed by emergency module 756 and/or building module 746, according to some embodiments. Control device 214 may receive a weather forecast 1502 from a weather server 608 (step 1602) and display the weather forecast 1502 via user interface 702 of control device 214 (step 1604). Control device 214 may illuminate ambient lighting 1512 of control device 214 in response to the weather forecast 1502 indicating a weather-related warning (step 1606). In some embodiments, audio 1514 may be generated when the weather forecast 1502 indicates a weather-related warning. The audio can be a siren, a warning message, and/or any other emergency related audio. Control device 214 may determine an adjustment to a control signal 1510 for HVAC equipment 738 based on the weather forecast (step 1608). Control device 214 may generate and provide an adjusted control signal 1510 to HVAC equipment 738. In some embodiments, the control signal 1510 may cause shutters and/or doors to automatically close. The control signal 1510 may cause building sirens (e.g., speakers 504) to play emergency related audio (e.g., "Please evacuate the building", "Take shelter away from windows", etc.)

Figure 16B:
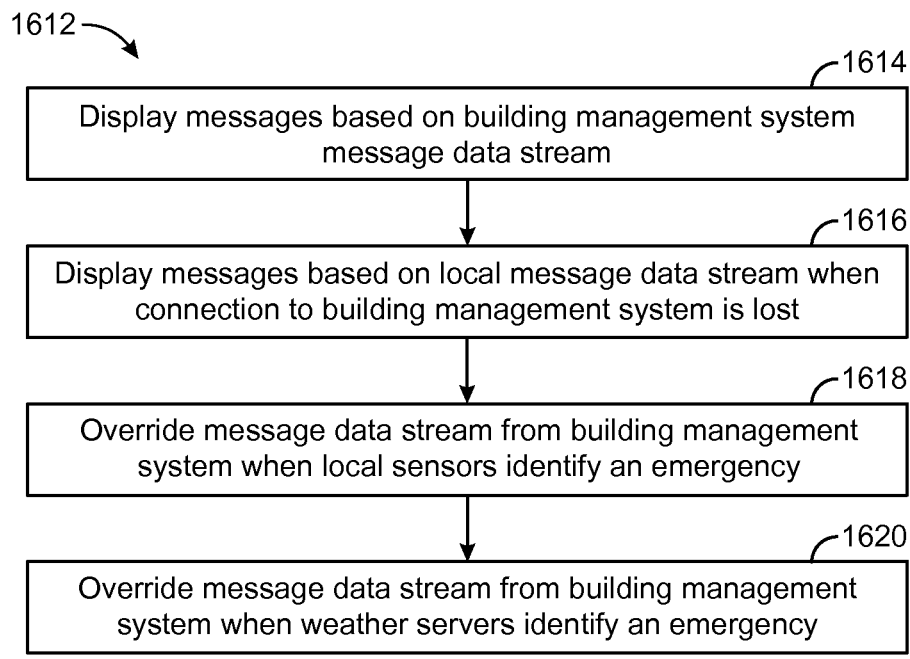
FIG. 16B is a flowchart of operations for prioritizing messages and data streams with the control device of FIG. 7, according to an exemplary embodiment.

Referring now to FIG. 16B, a flowchart of process 1612 illustrating the propriety of message data streams is shown, according to an exemplary embodiment. In some embodiments, process 1612 may be operated by control device 214 as described with reference to FIG. 7. In step 1614, control device 214 receives messages (e.g., general messages, emergency messages, etc.) based on a data stream from the building management system (e.g., building management system 610). Control device 214 may be configured to display general messaging (e.g., zone temperatures, building events, etc.) and/or emergency information on user interface 702 based on a data stream received from building management system 610.

In some embodiments, if a connection is lost between control device 214 and building management system 610, control device 214 may display messages stored and/or generated locally on control device 214 (step 1616) on user interface 702. In some embodiments, the display messages stored and/or generated locally on control device 214 include zone temperatures, zone humidity, building events, etc. In the event that an emergency is detected by emergency sensors (e.g., building emergency sensor(s) 606) connected to control device 214, the general messages received from building management system 610 may be overridden and emergency messages may be displayed on user interface 702 based on data received from the emergency sensors (step 1618). In some embodiments, when the data received from the emergency sensors is above a predefined threshold and/or below another predefined threshold, an emergency may be identified. In the event that an emergency is detected by emergency sensors (e.g., building emergency sensor(s) 606) connected to control device 214, the general messages stored locally and/or determined by control device 214 may be overridden and emergency messages may be displayed on user interface 702 based on data received from the emergency sensors.

In some embodiments, control device 214 may receive a message from a weather server (e.g., weather server 608). Control device 214 may be configured to override general messages received from building management system 610 when a notification for weather related emergency and/or any other type of emergency is received from weather server 608 (step 1620). Control device 214 may be configured to display weather related emergency notifications and directions via user interface 702 over the general messages received from building management system 610.

Figure 17:
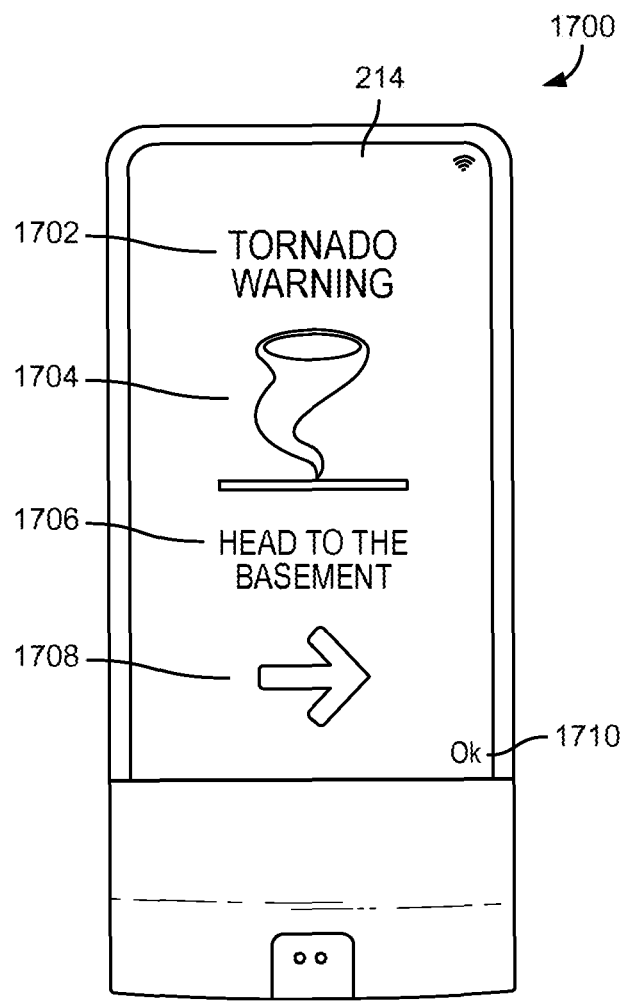
FIG. 17 is a drawing of the control device of FIG. 15 displaying an emergency warning, according to an exemplary embodiment.

Referring now to FIG. 17, a drawing of a device displaying an emergency screen 1700 during an emergency situation is shown, according to an exemplary embodiment. In some embodiments, emergency screen 1700 may be displayed by control device 214. Emergency screen 1700 is shown to include an alert title 1702, an alert icon 1704, instructions 1706, directions 1708, and menu option 1710.

Emergency screen 1700 is shown to have an alert title 1702 describing the contents of the page. In this exemplary embodiment, the title is "TORNADO WARNING." In some embodiments, alert title 1702 is customizable to provide more information. In other embodiments, alert title 1702 is customizable to provide less information. Alert title 1702 may be a button which takes the user to a page related to the title. For example, clicking alert title 1702 may take a user to a menu of pages related to "TORNADO WARNING." In some embodiments, clicking and/or pressing alert title 1702 navigates to a website and/or other entity. The website may be a weather server and may provide more information into the nature of the emergency.

Emergency screen 1700 is also shown to have an alert icon 1704. In this exemplary embodiment, alert icon 1704 is an image of a tornado. Alert icon 1704 may be any symbol, text, etc., and indicates the nature of the alert. For example, alert icon 1704 may be an image of a snowflake, text reading "FLOOD," text reading "FIRE," text reading "ACTIVE SHOOTER," etc. Alert icon 1704 provides information to a user about the alert, and may be any indicator relating to any type of emergency.

Emergency screen 1700 is shown to have instructions 1706. Instructions 1706 can provide information to a user about how to proceed in the current situation. In some embodiments, instructions 1706 may inform a user of how to exit a building. For example, instructions 1706 may inform a user of which room to head to. In other embodiments, instructions 1706 inform a user of which authorities to inform, etc. For example, instructions 1706 may instruct a user to call an ambulance, then the police, then building and/or campus security. Instructions 1706 may be downloaded from a network (e.g., network 602). In some embodiments, instructions are requested from network 602. In various embodiments, instructions are pushed to control device 214. Instructions 1706 may be stored for access by control device 214 in specific situations. In some embodiments, instructions 1706 may be stored locally on control device 214. In other embodiments, instructions 1706 may be stored remotely from control device 214. Instructions 1706 may be stored anywhere and retrieved by control device 214.

Emergency screen 1700 is also shown to have directions 1708. In some embodiments, directions 1708 may be an embodiment of instructions 1706. In other embodiments, directions 1708 provide different information from instructions 1706. Directions 1708 may provide a user information regarding where to go. For example, directions 1708 may be an arrow pointing in the correct direction to go. In some embodiments, control device 214 is portable, and may detect movement to alter directions 1708. For example, directions 1708 may change depending on the direction a user is facing. Directions 1708 may be any indicator providing directional information, and is not limited to those specifically enumerated.

Emergency screen 1700 is also shown to have a menu option 1710. In this exemplary embodiment, option 1710 is an "Ok" button. For example, option 1710 may accept the prompt. In some embodiments, option 1710 may simply dismiss the prompt. In other embodiments, option 1710 may proceed to the next action. In some embodiments, option 1710 is a forward button, a menu, etc. Option 1710 may perform any function, and is not limited to those specifically enumerated.

Figure 18:
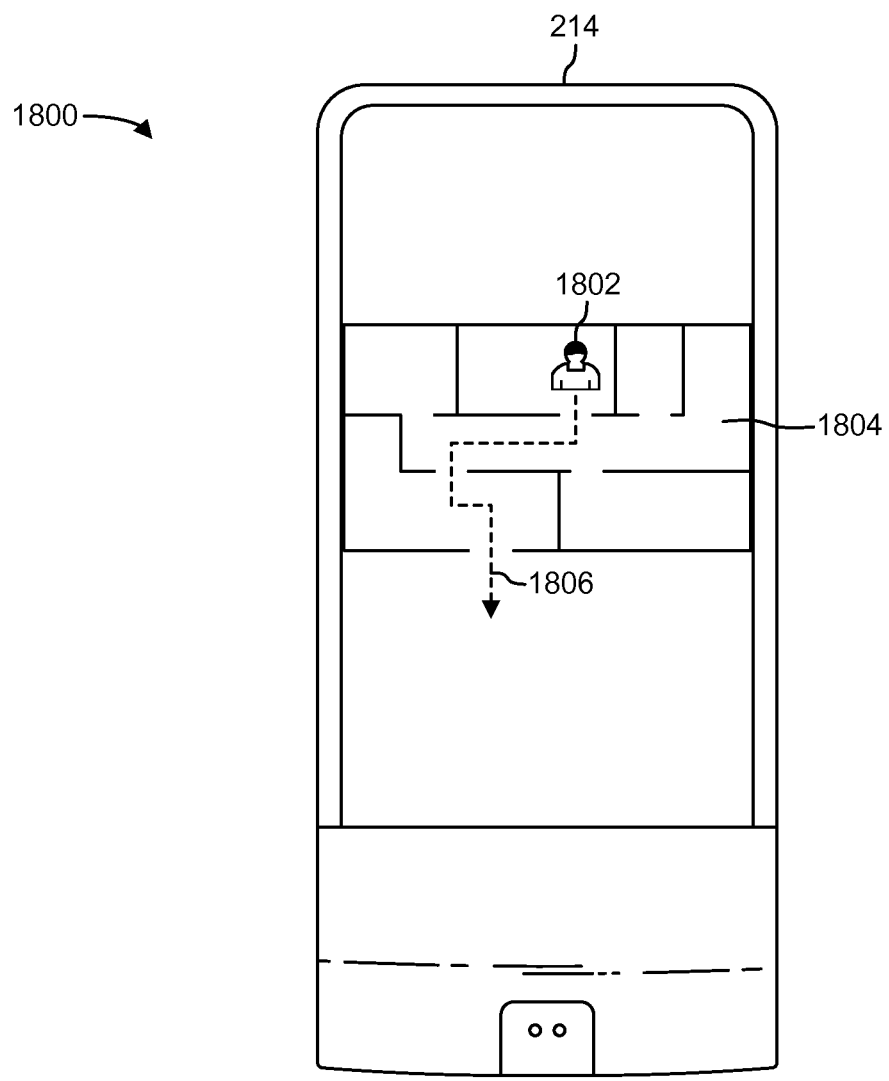
FIG. 18 is a drawing of the control device of FIG. 15 displaying an evacuation route, according to an exemplary embodiment.

Referring now to FIG. 18, an emergency screen 1800 of an evacuation route is shown, according to an exemplary embodiment. In some embodiments, emergency screen 1800 is displayed by control device 214. Screen 1800 is shown to include position indicator 1802, floorplan 1804, and directions 1806. Screen 1800 may include other elements and components, and is not limited to those specifically enumerated.

Screen 1800 is shown to include position indicator 1802. Position indicator 1802 may provide information on the whereabouts of a user, or another person, item, component, etc. For example, in this exemplary embodiment, position indicator 1802 is shown as an image of a person, and indicates the position of the person. In some embodiments, position indicator 1802 may indicate the position of multiple users, items, etc. Position indicator 1802 may further include a differentiating label, which may indicate which user, item, etc. is shown by each of the multiple indicators. In other embodiments, position indicator 1802 may indicate the position of a single user, item, etc. Position indicator 1802 may be any symbol, text, etc., and is not limited to those specifically enumerated.

Screen 1800 is shown to include floorplan 1804. Floorplan 1804 may be a diagram of a floorplan of an area serviced by control device 214. In some embodiments, the area is the area in which control device 214 is installed. In other embodiments, the area is another area, and may be selected by a user. In some embodiments, floorplan 1804 may show multiple locations. For example, floorplan 1804 may show both floors of a two-story building. A user may be able to select multiple locations to display (e.g., the top floor and the fourth floor of a 35 story building). In other embodiments, floorplan 1804 may show a single location. Floorplan 1804 may display any number of any locations, and is not limited to those specifically enumerated.

Screen 1800 is also shown to include directions 1806. Directions 1803 may provide information to a user regarding how to navigate to a certain location (i.e., evacuate). In some embodiments, directions 1806 provide the fastest route out of a building. For example, directions 1806 may direct a user to the exit of a building in case of an emergency. In other embodiments, directions 1806 provide a user with a route to a specified location. For example, directions 1806 may direct a user to a shelter (e.g., a basement fallout shelter, a safe location with no windows, etc.). In yet other embodiments, directions 1806 may allow a user to select options for the route. For example, a user may be able to indicate that she wishes to stay on the same floor, avoid stairs, etc. In yet other embodiments, directions 1806 may enable a user to select multiple destinations. For example, a user may indicate that he wishes to stop by a supply room before continuing to a conference room. The user may be able to make edits to any selections made. Directions 1806 are not limited to those forms and features specifically enumerated.

Figure 19:
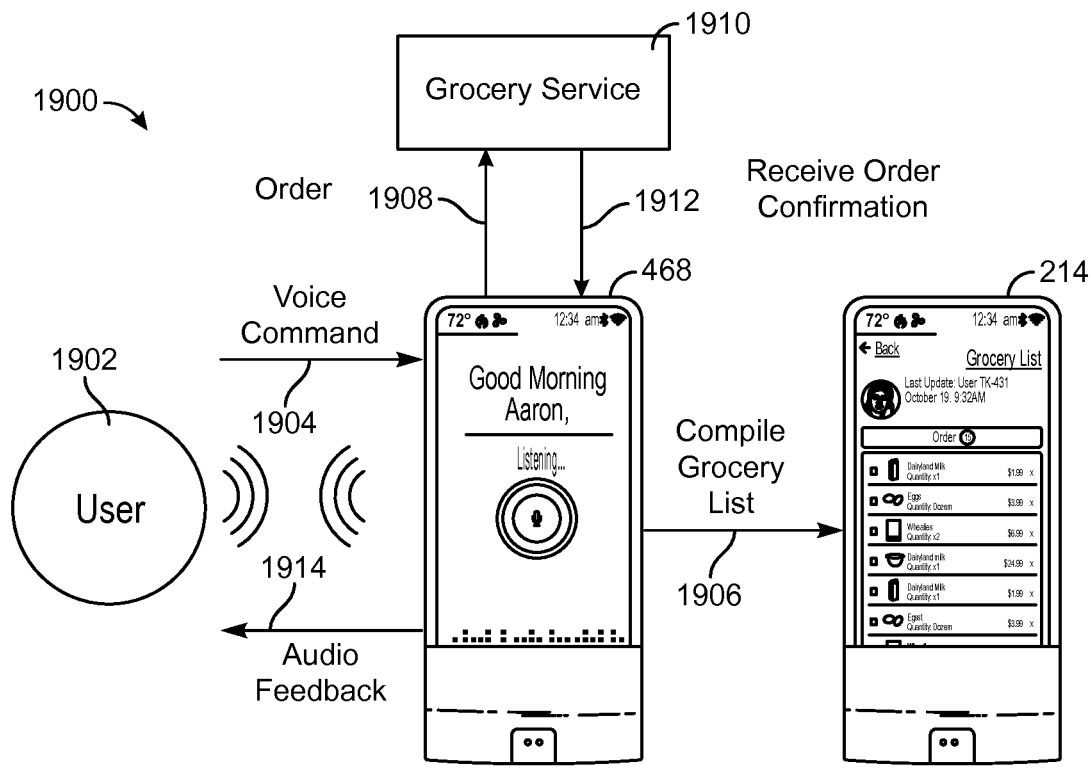
FIG. 19 is a drawing illustrating the control device of FIG. 7 compiling a grocery list, according to an exemplary embodiment.
Figure 20:
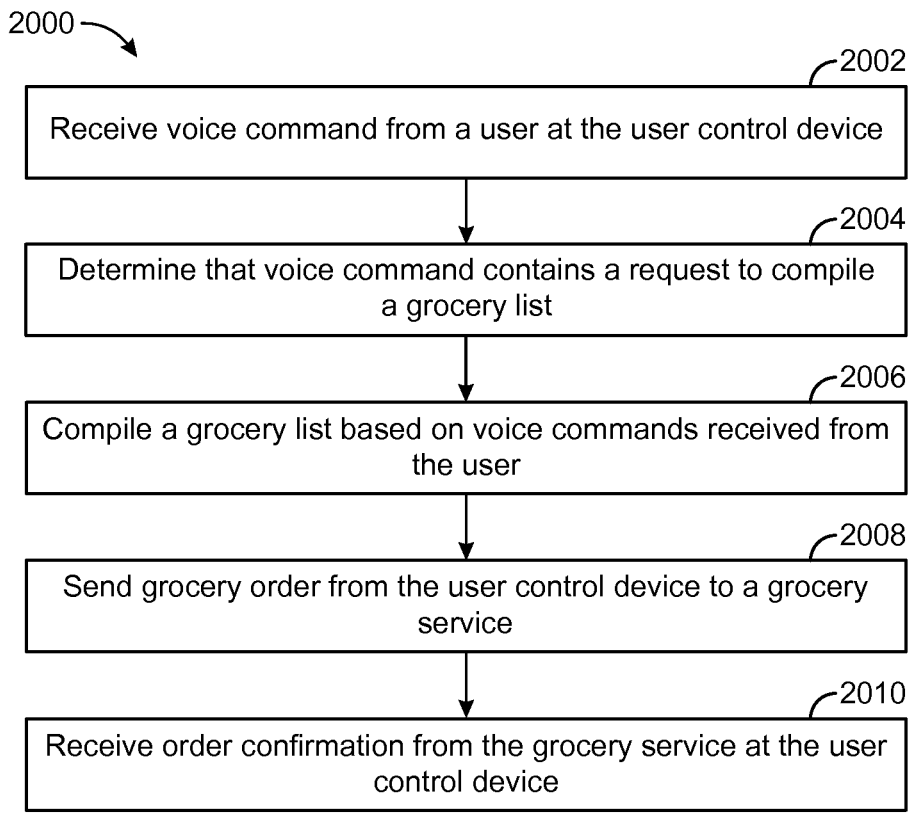
FIG. 20 is a flowchart of operations for compiling a grocery list with the control device of FIG. 19, according to an exemplary embodiment.

Referring now to FIGS. 19-20, a diagram 1900 and flowchart 2000 illustrating a control process which may be performed by voice control module 748 is shown, according to an exemplary embodiment. In some embodiments, flowchart 2000 is performed by voice command module 744. Control device 214 may receive a voice command 1904 from a user 1902 (step 2002) via a microphone (e.g., microphone 726) and may determine that the voice command 1904 contains a request to compile a grocery list (step 2004). In some embodiments, the voice command 1904 may be a concierge question as described with reference to FIGS. 30-32. Control device 214 may compile a grocery list 1906 based on the voice command 1904 received from the user 1902 (step 2006). In some embodiments, control device 214 replies to a concierge questions via a speaker (e.g., speaker 710). In some embodiments, control device 214 is configured to send a grocery order 1908 to a grocery service 1910 (step 2008) and receive an order confirmation 1912 from the grocery service 1910 (step 2010). Control device 214 may provide an audio feedback 1914 indicating that the grocery list has been updated and/or that the grocery order has been placed. In various embodiments, the grocery list can be updated and/or an order can be placed through touch based input. In some embodiments, the steps of flowchart 2000 can be performed by touching buttons on a touch screen associated with control device 214.

Health Care and Hospital Features

Figure 21:
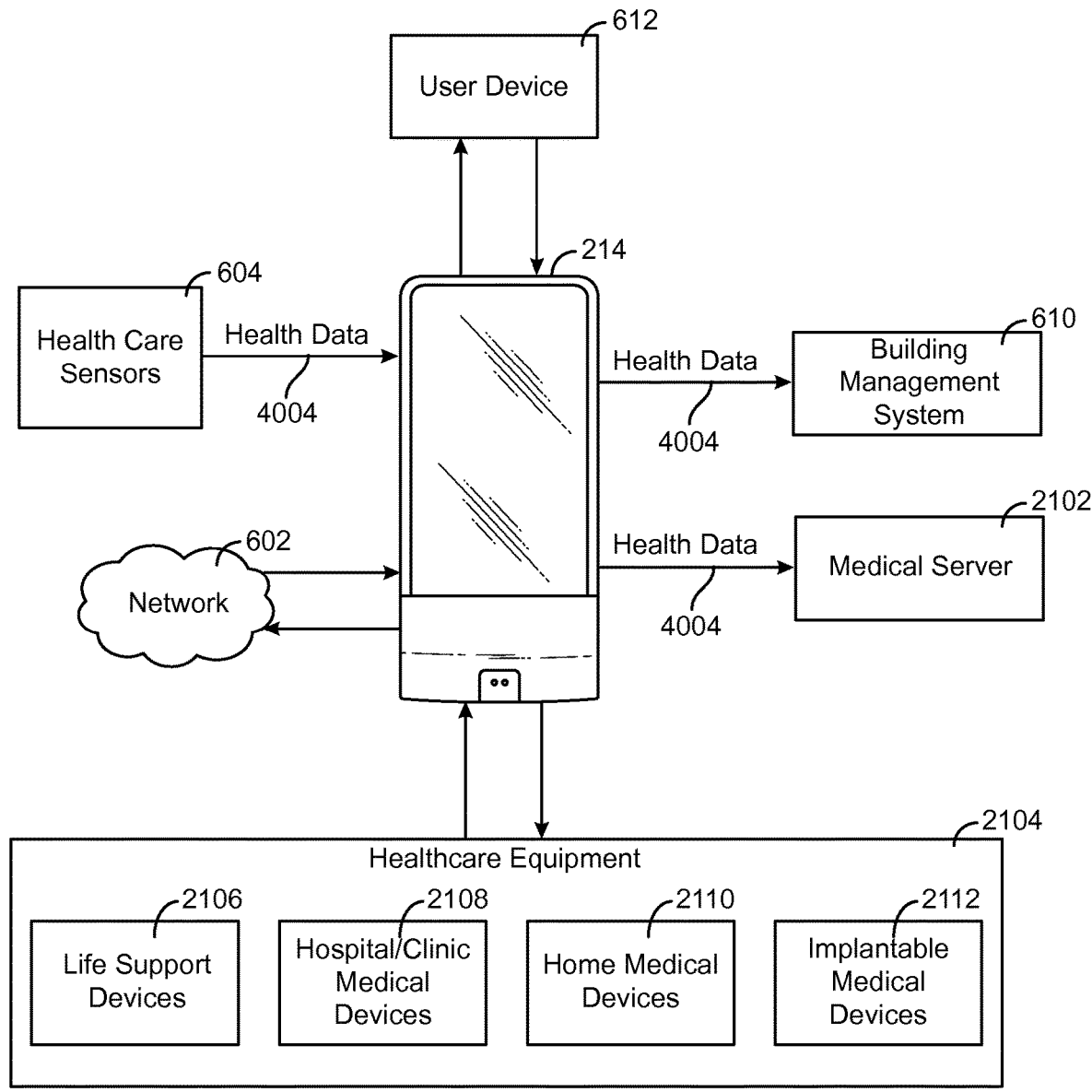
FIG. 21 is a diagram of the control device of FIG. 7 communicating with health related devices and systems, according to an exemplary embodiment.

Referring now to FIG. 21, control device 214 is shown to communicate to various health care devices and systems, according to an exemplary embodiment. In some embodiments, healthcare module 752 facilitates healthcare functions of control device 214. Control device 214 shown to interact with healthcare sensors 604, user device 612, building management system 610, medical server 2102 and network 602. In some embodiments, control device 214 communicates with healthcare equipment 2104. In various embodiments, the healthcare module 752 communicates with healthcare equipment 2104 directly and/or via network 602. In some embodiments, healthcare equipment 2104 is shown to include life support devices 2106, hospital/clinic devices 2108, home medical devices 2110, or implantable medical devices 2112 (e.g., pacemakers, cardioverter defibrillators, etc.).

Healthcare module 752 facilitates healthcare functionality of control device 214. Functions performed by healthcare module 752 may include monitoring the health of occupants of the area in which controller 468 is installed. In some embodiments, healthcare module 752 may monitor an occupant's health through data collected by healthcare sensors 604 and/or may determine a health metric for the occupant based on the data collected by healthcare sensors 604. For example, healthcare module 752 may monitor an individual's health by tracking his temperature through healthcare sensor 604. In some embodiments, healthcare sensor 604 is one or more or a combination of a smartwatch, a smart wrist band, a heart rate monitor, a pacemaker, a portable insulin device, and/or any other wearable medical device. In some embodiments, healthcare sensor 604 is a camera, an infrared camera, and/or any other occupancy detection device. Healthcare module 752 may use healthcare sensors 604 to monitor a user's waking/rest times, heart rate, insulin levels, body temperature, etc. Healthcare module 752 is not limited to monitoring the health attributes specifically enumerated, and may monitor any aspect of a user's bio-status. In some embodiments, control device 214 is configured to forward any data collected by healthcare sensors 604 and/or healthcare equipment 2104 to medical server 2102. In some embodiments, medical server 2102 is a hospital server, a nurse's station computing system, and/or an emergency response operator server.

Healthcare module 752 may communicate with user interface 702 or user device 612 belonging to a user to sense and collect health data. For example, healthcare module 752 may communicate with an individual's smartwatch which contains a heart rate monitor to track the individual's heart rate. In some embodiments, control device 214 does not communicate with healthcare sensors 604 which monitor a user's health, and instead collects data solely from healthcare equipment 2104. In other embodiments, control device 214 contains sensors and collects data from other devices, combining the data collected to produce a general metric of a user's health.

Healthcare module 752 may detect a change of a predetermined amount or a sensor value over or under a predetermined threshold value (e.g., abnormally high and/or low heart rate (i.e., bradycardia and tachycardia), abnormally high and/or low insulin level, abnormally high and/or low temperature, etc.). In some embodiments, healthcare module 752 may monitor the heart rate of an occupant and determine if the heart rate is abnormal (i.e., arrhythmia). In some embodiments, healthcare module 752 may alert a user, the monitored occupant, a nurse's station computing system, a hospital server, a hospital computing system, call 911 (i.e., send a message to an emergency response server and/or an emergency response computing system) etc. For example, healthcare module 752 may communicate with user device 612 of a user to display an alert describing the situation triggering the healthcare alert. Healthcare module 752 may communicate with network 602 to update a healthcare system (e.g., medical server 2102) with new data collected, set a flag on a user's condition, etc. For example, healthcare module 752 may send data to a patient database and update a value for a body temperature, blood pressure, etc.

In some embodiments, a heart rate and/or body temperature is measured by a smart wrist band and/or smart watch (e.g., healthcare sensors 604). The heart rate and/or body temperature (e.g., health data 4004) may be sent to control device 214. In some embodiments, healthcare sensors 604 are cameras. The cameras may be heat sensitive. The heat images (e.g., health data 4004) may be sent to control device 214. Control device 214 may determine the body temperature of various occupants of a building (e.g., building 10) based on the heat images (e.g., health data 4004) received from healthcare sensors 604.

Healthcare module 752 may send push alerts to user device 612 from network 602. For example, network 602 may receive a notification that it is time for a middle school individual to take her medication. Control device 214 may communicate with user device 612 of the individual, a teacher, a nurse, etc. to alert the user of user device 612 that it is time for the individual to take her medication. In some embodiments, control device 214 may communicate with a user through user interface 702 to convey healthcare information. For example, network 602 may receive a notification that it is time for an individual's appointment with the nurse. Network 602 may communicate with control device 214 to convey the information to the nurse, the individual, the individual's current teacher, etc. For example, control device 214 may have access to a user's schedule and/or calendar, and adjust actions accordingly. In some embodiments, control device 214 may determine that an individual is currently in math class, and may send an alert to user device 612 of the individual. In other embodiments, control device 214 may determine that an individual is currently in a free period with a specific teacher in a specific room, and may send an alert to a control device 214 installed in the room, or to a user device 612 of the teacher. Control device 214 may convey healthcare information through any media, and is not limited to those specifically discussed.

Healthcare module 752 may contain some or all of the features of occupancy module 754. The occupancy detectors (e.g., healthcare sensors 604, sensors 714, etc.) may be installed in a patient room in a health care facility and may be used to monitor the presence of the patient in the room. Healthcare module 752 may communicate with the network 602, medical server 2102, and/or building management system 610 to alert medical personnel if a patient leaves their room without permission. Healthcare module 752 may communicate with a user interface to determine the identities of persons in a patient's room. For example, the occupancy detector may use a camera and facial recognition software to determine the identities of medical personnel that are present. Healthcare module 752 may use camera and facial recognition to determine the presence of visitors and other unauthorized personnel in a patient's room.

In some embodiments, the healthcare module 752 communicates with users or relevant persons when an emergency situation arises (e.g., building management system 610, medical server 2102, user device 612, etc.) Healthcare module 752 may receive the patient's health information from the network, healthcare sensors 604, and/or healthcare equipment 2104, and display it to medical personnel if a medical alert is detected (e.g., abnormal blood pressure, abnormal oxygen saturation, abnormal heart rate, abnormal heart rhythm, etc.). In another embodiment, healthcare module 752 may communicate to the patient or to medical personnel when a regular medical procedure is scheduled. For example, healthcare module 752 may communicate to the patient or to medical personnel when a pill is to be taken, when an IV is to be replaced, when a wound dressing is to be changed, etc. In another embodiment, healthcare module 752 may communicate with alert module to communicate with user device 612 of a patient. For example, if a patient is undergoing treatment requiring regular pill taking may receive alerts from an alert module on a mobile device (e.g., a smartphone, smart watch, wearable, laptop, etc.).

Healthcare module 752 may communicate with any systems, devices, etc. connected to control device 214. For example, healthcare module 752 may issue an alert to medical personnel which is pushed to control device 214 (e.g., a nurse's station) and mobile devices (e.g., user device 612 of medical personnel assigned to the patient, etc.) Healthcare module 752 may issue an alert which is pushed to mobile devices 612 through network 602. Healthcare module 752 may be in communication with all modules of control device 214.

In some embodiments, healthcare module 752 may require the credentials of healthcare personnel to make changes related to treatment of the patient. The healthcare module 752 may record the unique identity of any user making changes to a patient's treatment.

Figure 22:
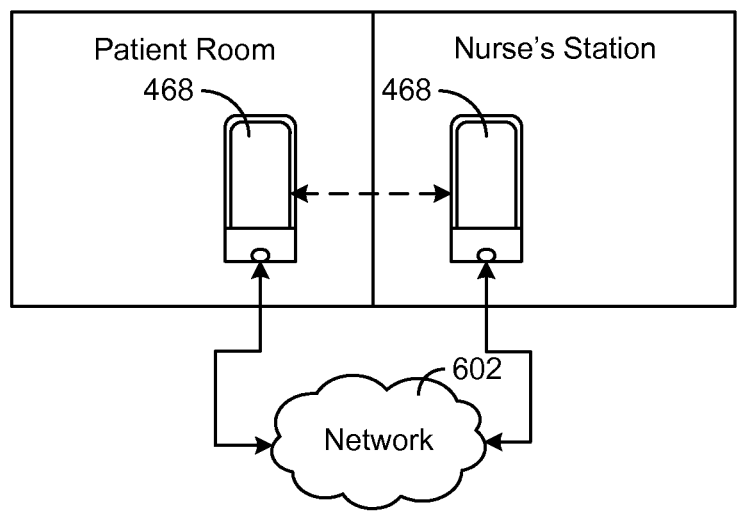
FIG. 22 is a drawing of a medical application for the control device of FIG. 21, according to an exemplary embodiment.
Figure 23:
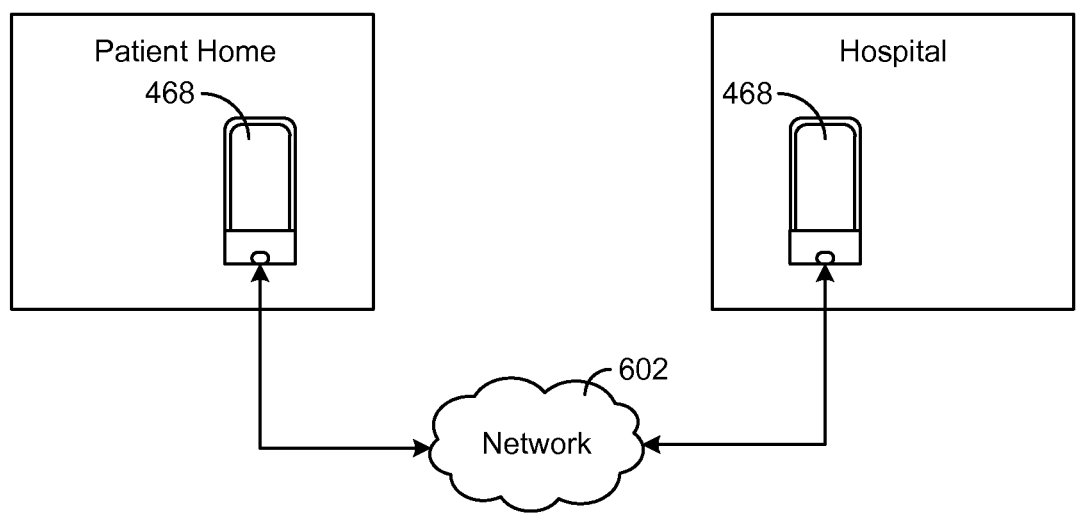
FIG. 23 is a drawing of another medical application for the control device of FIG. 21, according to an exemplary embodiment.

Referring now to FIGS. 22 and 23, drawings of control device 214 communicating with other control devices 468 are shown, according to exemplary embodiments. In some embodiments, other control device 214 may be located locally, such as in another room of the same building. For example, referring to FIG. 22, control device 214 is located in a patient's room in a hospital. Control device 214 may communicate with another control device 214 at a nurse's station in the same hospital. The control device 214 may be directly connected and may communicate directly with each other. In another embodiment, the control device 214 may be connected via a network.

In various embodiments, other control devices 468 are located remotely, such as in other buildings, states, countries, etc. For example, referring to FIG. 23, control device 214 in a patient's home or an assisted living facility may communicate with control device 214 at a hospital to facilitate out-patient care of the patient. Other control devices 468 may be located anywhere relative to control device 214, and are not limited to locations specifically discussed or described.

In an exemplary scenario, a patient may be discharged from a medical care facility, such as a hospital to their home or to an assisted living facility. The patient may, for example, have received a routine checkup or may have been treated for a chronic or acute medical situation. The patient may be automatically monitored by healthcare equipment 2104 as described with reference to FIG. 21 after being discharged using one or more control device 214 provided in the patient's home or assisted living facility. The patient's health may be monitored using implantable medical devices 2112 or home medical devices 2110 to allow remote medical personnel to monitor the post care recovery of the patient. Control device 214 may be utilized to facilitate continuing medical care (e.g., physical therapy, medication schedule, follow-up visits to a medical facility, etc.).

Control device 214 may continue to monitor the health of the patient after receiving medical care. If control device 214 detects a medical alert, it may take an action, depending on the severity of the medical alert. For example, control device 214 may prompt the patient to return to the hospital, alert a local medical personnel (e.g., an in-home nurse or caretaker), or may have an ambulance sent to the patient's location.

In some embodiments, control device 214 can transmit patient data to a central computer system (over a local network or via the internet) in compliance with HIPAA standards and regulations.

In some embodiments, control device 214 may not collect personal health data without consent of the person whose data is being collected. In other embodiments, control device 214 may offer an opt-out system, where control device 214 is prevented from collecting personal health data when a user specifically opts out. In yet other embodiments, control device 214 may collect data from all users, and anonymize all data before storing, analyzing, etc. For example, control device 214 may collect data from all patients undergoing a particular procedure and anonymize all data before sending to a research facility, hospital, etc.

Control device 214 may collect data from each person, and each person is given a window of time to opt-out out retroactively or delete data. In some embodiments, control device 214 may communicate with the users through the user interface, a mobile devices, and/or the network to inform users that their data has been collected. For example, control device 214 may push a notification out to all applicable users over the network that his or her information has been collected, and will be stored or sold to a hospital within 24 hours. In some embodiments users may be given the full 24 hours to opt-out or delete data. In other embodiments, users may be given any predetermined period of time in which to respond or take action.

Control device 214 may communicate with users to ask for permission to share his or her information. For example, control device 214 may display a prompt on a mobile device of each person whose data was collected. In some embodiments, control device 214 may share a user's data when permission has been granted. In other embodiments, control device 214 may share non-sensitive user data that has been anonymized.

Figure 24:
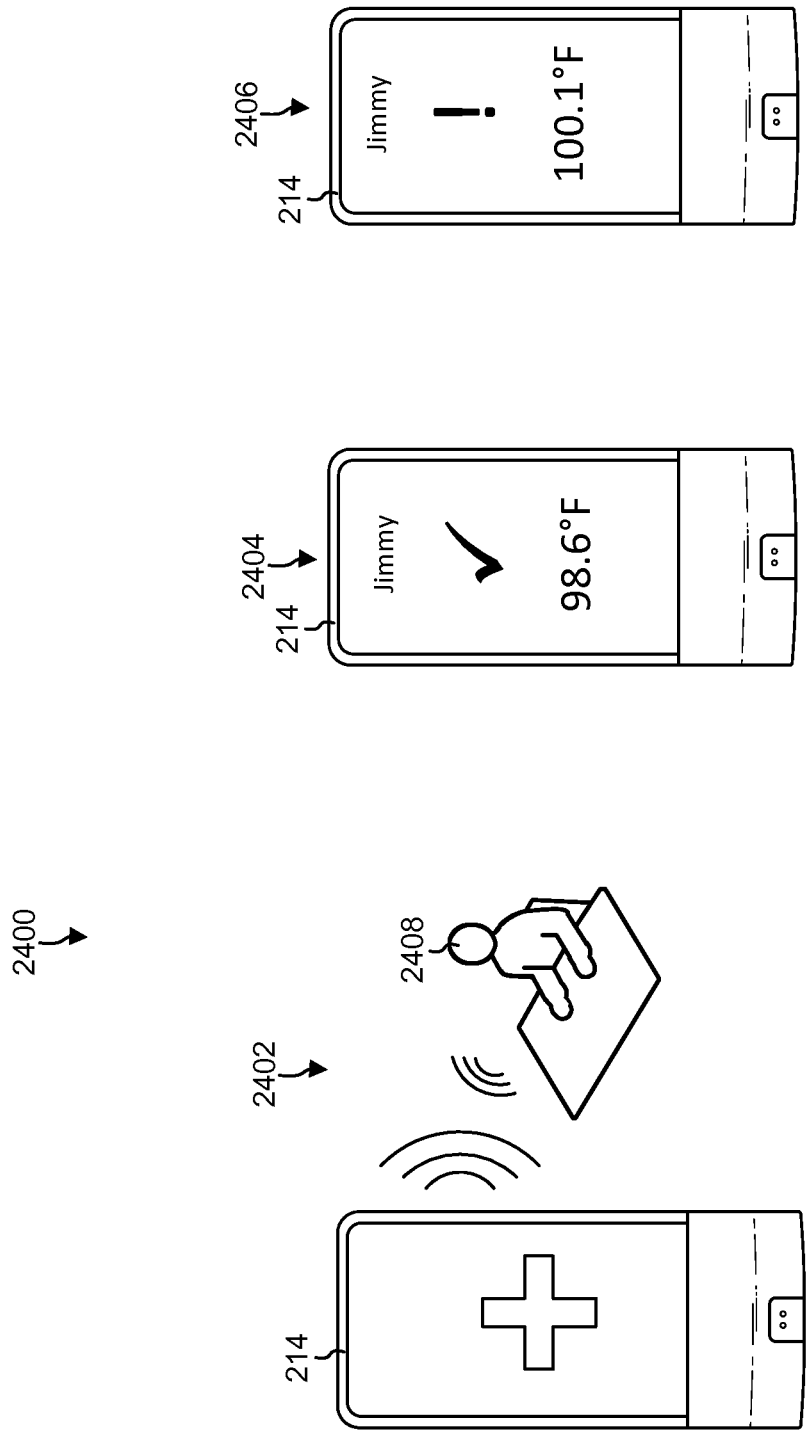
FIG. 24 is a diagram of the control device of FIG. 21 monitoring the health of an individual, according to an exemplary embodiment.

Referring now to FIG. 24, a diagram of scenario 2400 in which control device 214 monitors an individual's 2408 health is shown, according to some embodiments. In part 2402, control device 648 is shown to communicate with an individual 2408 via audio, visual items on a screen, a device, etc. The device may be a smartphone, smart watch, fitness tracker, etc. In other embodiments, the device may be a medical device, such as a pace maker, insulin pump, etc. The device may be any device, and is not limited to those specifically enumerated.

The individual 2408 may communicate directly with control device 214 through a user interface, voice commands, etc. For example, individual 2408 may tell control device 214 that he does not feel well. In some embodiments, control device 214 may trigger an alert or take some other action depending on the information received. In other embodiments, control device 214 may wait for specific instructions to take action before executing any commands.

In part 2404, a screen of control device 214 during normal health monitoring operation is shown. Control device 214 has confirmed that individual's 2408 body temperature, displays the temperature, the individual's name, an indication that all is well, and takes no further action. In some embodiments, control device 214 stores the information. In other embodiments, control device 214 sends the information to healthcare institutions, facilities, professionals (e.g., medical server 2102, building management system 610, etc.) Control device 214 may handle all information in accordance with HIPAA rules and regulations.

Control device 214 may monitor and collect any health data, such as blood pressure, heart rate, etc. For example, control device 214 may communicate with a heart rate monitor, and raise an alarm if an individual's heart rate becomes irregular, over a threshold rate, etc. For example, control device 214 may detect that an individual is experiencing a high amount of stress using a combination of body temperature and heart rate. Control device 214 is not limited to the health statistics specifically enumerated.

In part 2406, control device 214 has automatically detected that a health condition has arisen. In this exemplary depiction, the health condition is a fever, detected by the high body temperature. In other embodiments, the health condition may be high stress, arrhythmia, low blood sugar, etc. Control device 214 may produce a sound, vibrate, flash the screen, etc. to present an alert to a user. In some embodiments, control device 214 may send a signal to a user device (e.g., user device 612, network 602, building management system 610, medical server 2102, etc.) or some other system or device to display the alert, as described above.

Figure 25:
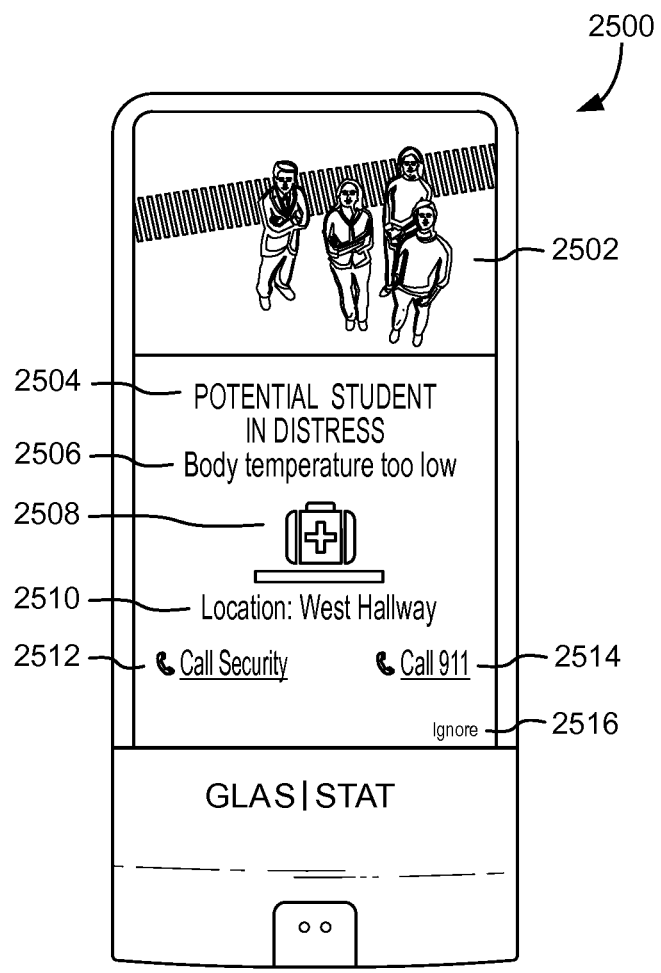
FIG. 25 is a drawing of a medical emergency screen displayed by the control device of FIG. 21, according to an exemplary embodiment.

Referring now to FIG. 25, a drawing of a screen 2500 displayed when an individual is in distress is shown, according to an exemplary embodiment. Screen 2500 is shown to include a live feed 2502 of the particular individual. In some embodiments, live feed 2502 may be a map or floorplan indicating where the individual is located. In other embodiments, live feed 2502 may be a still photo of the individual to help healthcare professionals locate the individual.

Screen 2500 further includes an alert message 2504 and a cause 2506. Alert message 2504 may display any message, such as "STUDENT COLLAPSE," "STUDENT EMERGENCY," etc. In some embodiments, alert message 2504 may be customized to provide more information, such as the individual's name, emergency contact information, etc. In other embodiments, alert message 2504 may be customized to display anything that may be more helpful or appropriate for the environment in which user control device is installed. Alert message 2504 is not limited to those messages specifically enumerated.

Cause 2506 may be any reason, such as "Cardiac distress," "Low blood sugar," etc. In some embodiments, cause 2506 may be customized to provide more information, such as the individual's name, emergency contact information, etc. In other embodiments, cause 2506 may be customized to display anything that may be more helpful or appropriate for the environment in which user control device is installed. Cause 2506 is not limited to those messages specifically enumerated.

Screen 2500 is further shown to include an icon 2508. Icon 2508 may give a user a quick impression of what the alert is related to. Control device 214 is capable of providing alerts for many different categories, such as inclement weather, security, health, etc. Control device 214 is not limited to those categories specifically enumerated. Icon 2508 may be a symbol, a word, etc., and may be any indication of what the alert is related to.

Screen 2500 is further shown to include a location 2510. Location 2510 may give a user the location of the particular individual to which the alert is related. In some embodiments, location 2510 is provided as text. In other embodiments, location 2510 is provided as a map. For example, location 2510 may be displayed as live feed 2502. Location 2510 may be displayed or presented to the user in any form, and is not limited to those specifically enumerated.

Screen 2500 is finally shown to include options 2512, 2514, and 2516. Options 2512, 2514, and 2516 may provide a user with options of actions to take. In some embodiments, screen 2500 may include more options. In other embodiments, screen 2500 may include fewer options. The options presented may be customized to be more appropriate for each situation. For example, if an individual's insulin pump needs to be restarted, control device 214 may present the option of restarting the pump. In some embodiments, option 2516 to ignore the alert may not be available. For example, if an individual is in critical condition, such as cardiac arrest, user control device may automatically execute options 2512 and 2514 by calling security and 911.

Concierge and Hotel Features

Figure 26A:
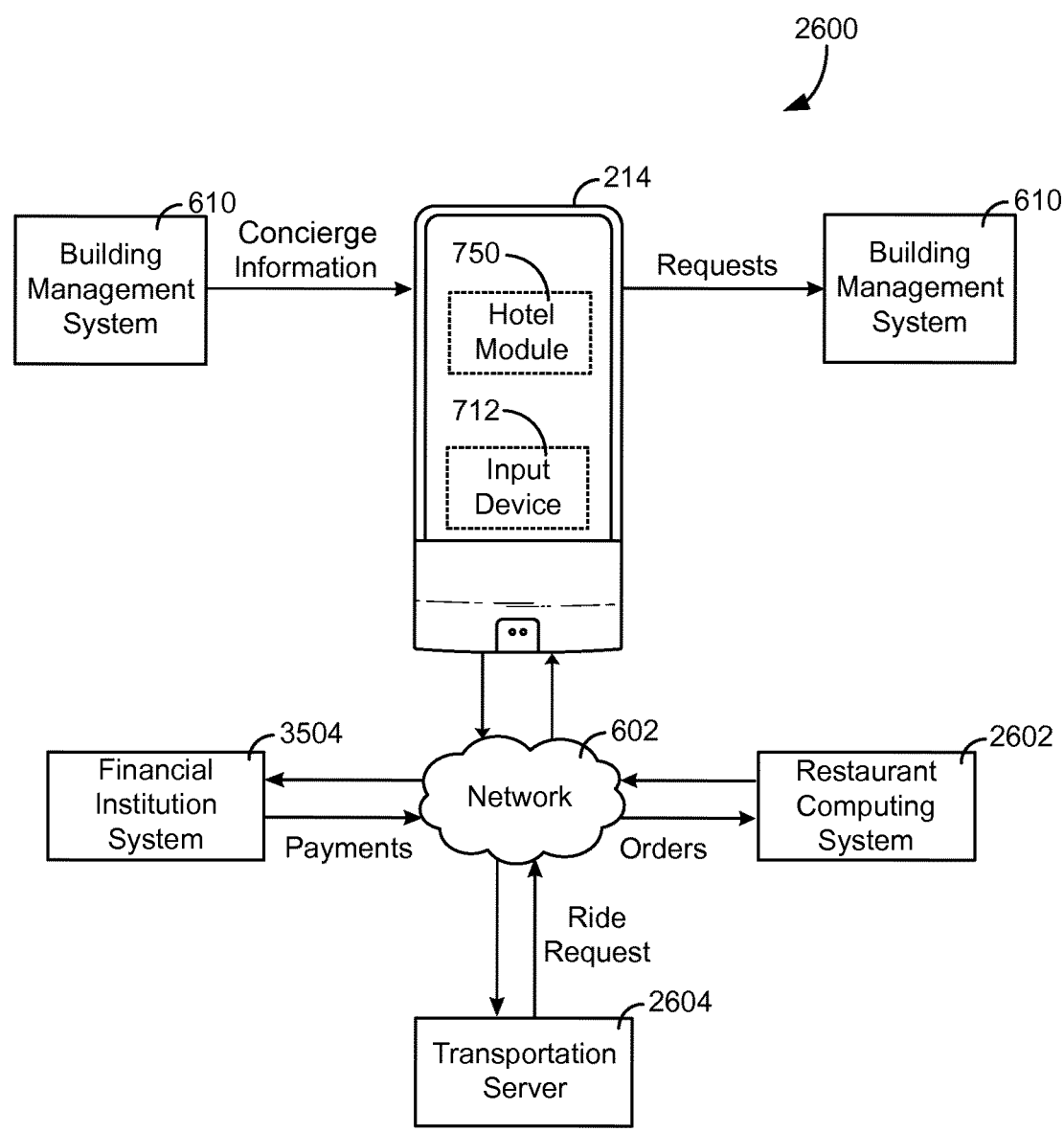
FIG. 26A is a diagram of the control device of FIG. 7 for hotel use, according to an exemplary embodiment.

Referring now to FIG. 26A, a diagram of control device 214 is shown for use in a hotel, according to an exemplary embodiment. In some embodiments, control device 214 receives concierge information from building management system 610. In some embodiments, the concierge information may include local attractions, local restaurants, and/or any other concierge related information. In some embodiments, hotel module 750 is configured to cause control device 214 to send a request for specific concierge information to building management system 610 via network 602 when a user requests concierge information via user interface 702 and/or microphone 726. In some embodiments, hotel module 750 may cause control device 214 to search for concierge information via the Internet (e.g., network 602) if the building management system does not have the requested concierge information.

In some embodiments, hotel module 750 is configured to process orders for food from local restaurants. In some embodiments, control device 214 (i.e., hotel module 750) may send a request to a restaurant computing system 2602 for a menu. Control device 214 may display the menu to the user via user interface 702 and may allow the user to order food directly through user interface 702 (i.e., enter orders through user interface 702). In some embodiments, the user may be able to send a reservation request to restaurant computing system 2602 via hotel module 750 and display device 702. A user may place an order via user interface 702 causing hotel module 750 to communicate with restaurant computing system 2602 via network 602. Hotel module 750 may cause payment module 758 to process any payment transactions for food orders with financial institution system 3504. Payment transactions are described in further detail at FIGS. 35-39.

In some embodiments, hotel module 750 is configured to process requests for taxis, busses, subways, trains, and/or planes. In some embodiments, control device 214 communicates with transportation server 2604. Transportation server 2604 may be Uber, Lyft, and/or any other taxi service. In some embodiments, transportation server 2604 is an airline server, a bus server, a train server, etc. Hotel module 750 may allow a user to request a ride from transportation server 2604 and may cause payment module 750 to process payment transactions via network 602 and financial institution system 3504. In some embodiments, input device 712 may be configured to scan credit and/or debit cards for payment for transactions with restaurant computing system 2602 and/or transportation server 2604. In some embodiments, payment module 758 facilitates the transaction with financial institution system 3504. Input device 712 is described in further detail in FIGS. 35-39.

Figure 26B:
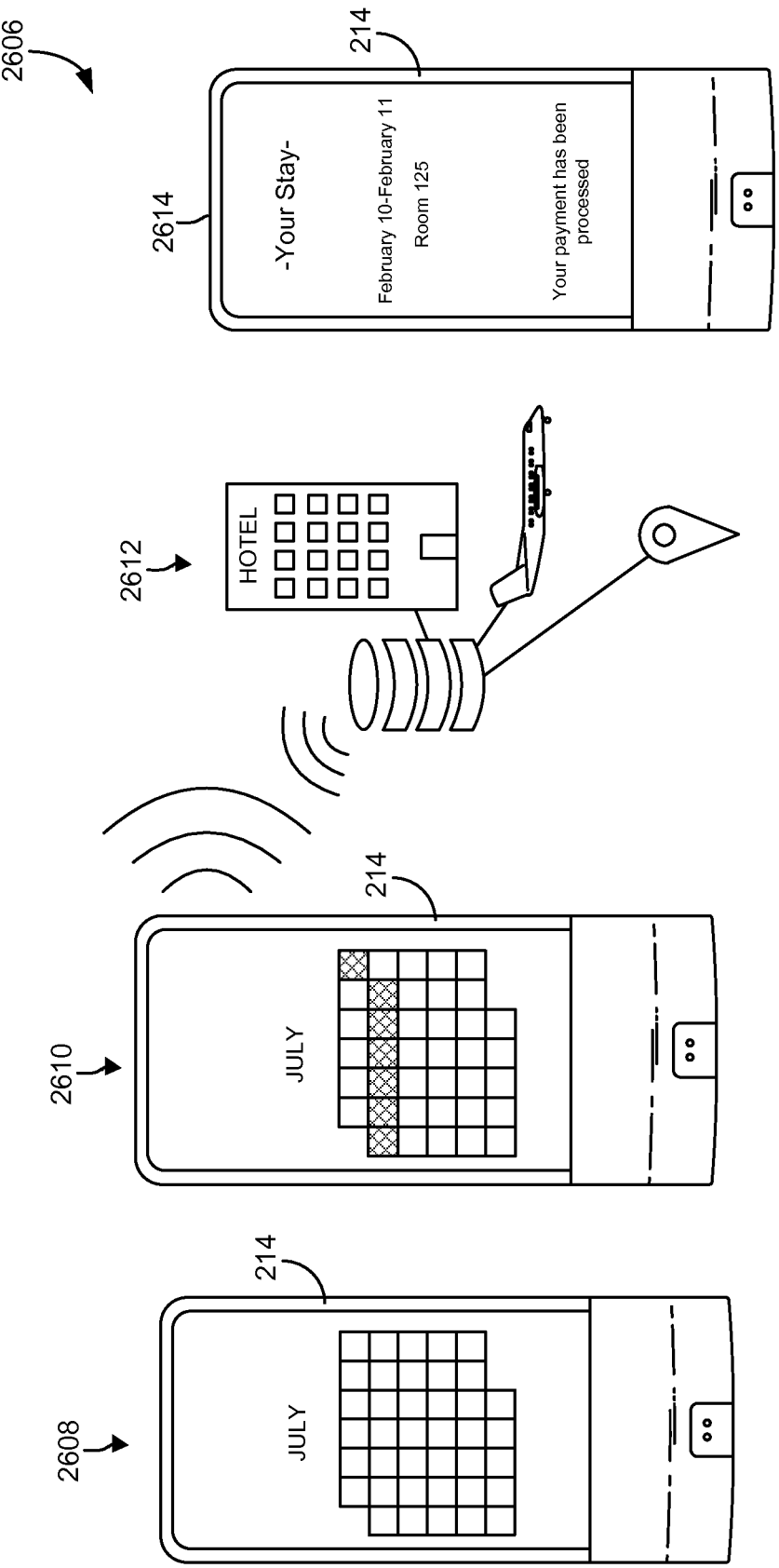
FIG. 26B is a flow diagram of operations for scheduling hotel reservations with the control device of FIG. 7, according to an exemplary embodiment.

Referring now to FIG. 26B, a process 2606 for scheduling a stay at a hotel is shown, according to some embodiments. In some embodiments, process 2606 is performed by hotel module 750 of control device 214. Process 2606 may be applied to scheduling any event, and is not limited to hotels, cruises, etc. Process 2606 begins with step 2608, in which a user provides input to a control device 214. The user may provide input through any means. For example, the user may provide input by voice command, tactile input to a user interface (e.g., user interface 702), gesture input, input to a mobile device (e.g., user device 612), etc.

According to this exemplary embodiment, a calendar interface may be provided to a user via the user interface and/or the mobile device. In some embodiments, the calendar interface may show the user's appointments and events. For example, a user's work and personal calendar events may be displayed on the calendar interface. In other embodiments, multiple users' schedules may be displayed on the calendar interface.

The calendar interface may show information such as availabilities for a hotel. In some embodiments, the control device 214 is located inside the hotel which it displays availability for. In some embodiments, the calendar interface may provide all availabilities. In other embodiments, the calendar interface may be sorted according to room size, amenities, etc. The calendar interface may not be specific to a single hotel. In some embodiments, the calendar interface may display availabilities for multiple hotels. The hotels shown may be selected by a user. In other embodiments, control device 214 may automatically select multiple hotels according to criteria such as price range, length of stay, amenities, distance to destinations, hotel ratings, etc.

The information may be displayed in any format. For example, control device 214 may display the information as drop-down boxes, check boxes, etc. In some embodiments, control device 214 may display content directly from a hotel's website, a travel website, etc. In other embodiments, control device 214 may display content parsed from a website, in a format native to control device 214.

Process 2606 continues with step 2610, in which a user selects a range of days for her stay at the hotel. In some embodiments, a user selects a range of consecutive days. In other embodiments, a user may select a set of non-consecutive days. The user may enter other information, such as billing information, number of guests, destination, etc. In some embodiments, the calendar interface may display the range of days selected as darkened days, checked boxes, etc. The information input by the user is transmitted from control device 214 to a building management system for a hotel (e.g., building management system 610) and/or any other server for the hotel.

Process 2606 continues with step 2612, the information transmitted from control device 214 is received by a database. In some embodiments, control device 214 may book a stay at the hotel directly using entered billing information. In other embodiments, control device 214 connects the user to a travel agent, to the hotel's booking website with the fields pre-populated, etc. The information transmitted from control device 214 may be received by any system, and is not limited to databases. In some embodiments, the database is connected to a hotel's main system, and hotel staff are notified. In some embodiments, the hotel's main system is building management system 610.

The database may be connected to additional services, such as destinations, airlines, etc. For example, control device 214 may automatically suggest flights from a billing address entered by the user to the destination entered by the user. In some embodiments, control device 214 may automatically select flights and present the user with a confirmation dialog. In other embodiments, control device 214 presents a set of available flights for the scheduled hotel stay. Control device 214 may also suggest, book, etc. activities, such as local attractions, tours, ground transportation, etc.

Control device 214 may learn from information entered by the user with his permission. For example, control device 214 may store information such as a user's preferences for flight times, direct vs. non-direct flights, seat preferences, hotel chain preferences, pillow firmness preferences, attractions, tours, ground transportation, etc. A user may be presented with a dialog confirming that she is allowing control device 214 to store or analyze such data. In some embodiments, the data is stored remotely. In other embodiments, the data is stored locally on control device 214.

Process 2606 continues with step 2614 in which control device 214 provides the user with information. In some embodiments, control device 214 provides a confirmation of all bookings made. In other embodiments, control device 214 provides a list of prospective bookings, contact information for each option, etc. Control device 214 may provide the user with any information. In some embodiments, control device 214 may not provide the user with further information.

In this exemplary embodiment, control device 214 is shown to provide the user with information through a user interface (e.g., user interface 702). In other embodiments, control device 214 may provide the user with information through any medium, format, etc. For example, control device 214 may provide the user with information through speakers (e.g., speakers 710), a mobile device (e.g., user device 612), etc.

Figure 27:
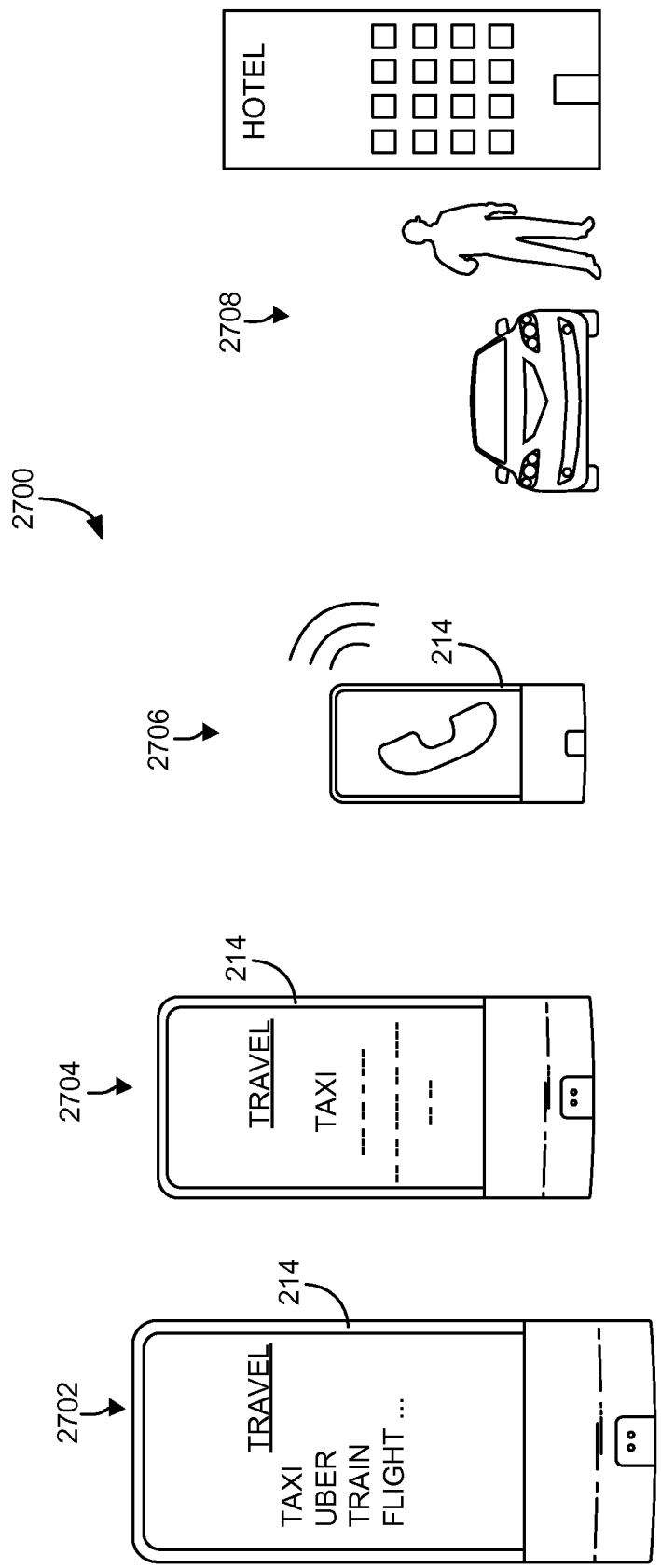
FIG. 27 is a flow diagram of operations for calling a taxi with the control device of FIG. 7, according to an exemplary embodiment.

Referring now to FIG. 27, a process 2700 for arranging transportation via control device 214 is shown, according to some embodiments. In some embodiments, process 2700 is performed by voice command module 744 and/or hotel module 750. Process 2700 begins with step 2702, in which a user is presented with a screen having options for arranging transportation. In some embodiments, process 2700 is performed automatically. In other embodiments, a user may choose to enter a transportation mode to arrange transportation via control device 214.

Process 2700 continues with step 2704, in which control device 214 may present the user with a list of available modes of transportation. For example, control device 214 may present the user with a list of links to different sites of different modes of transportation. In some embodiments, each option is a link which takes the user to a set of available options. Availability may be determined by criteria such as the current time, the desired time, the location, the distance, the mode of travel, extra considerations for the passenger (oversize luggage, animals, etc.), etc. In some embodiments, the user may enter the criteria via user interface 702. In various embodiments, the user may enter the criteria via microphone 726 and voice command module 744. Control device 214 may suggest the closest form of transportation if the selected mode is unavailable. In some embodiments, control device 214 may make suggestions and/or arrange the list of modes of transportation (i.e., most relevant mode of transportation to least relevant mode of transportation) based on the most commonly used, least expensive, fastest, a target destination, etc. For example, if no taxis are available at the desired time, control device 214 may suggest taking the subway.

Process 2700 continues with step 2706, in which control device 214 may make arrangements for the final selection. For example, once the user has selected the taxi company, times, options, etc., control device 214 may place a call to the company to make arrangements. In some embodiments, control device 214 may enter the information in the company's website. In other embodiments, control device 214 may present the information to the user, who will make the final arrangements himself.

Process 2700 continues with step 2708, in which the user is connected with her transportation. In some embodiments, the transportation travels to pick up the user. In other embodiments, the user travels to board the transportation. The travel arrangements may be made for travelling to a destination, travelling from a destination, etc. Travel arrangements may be made for any purpose.

Figure 28:
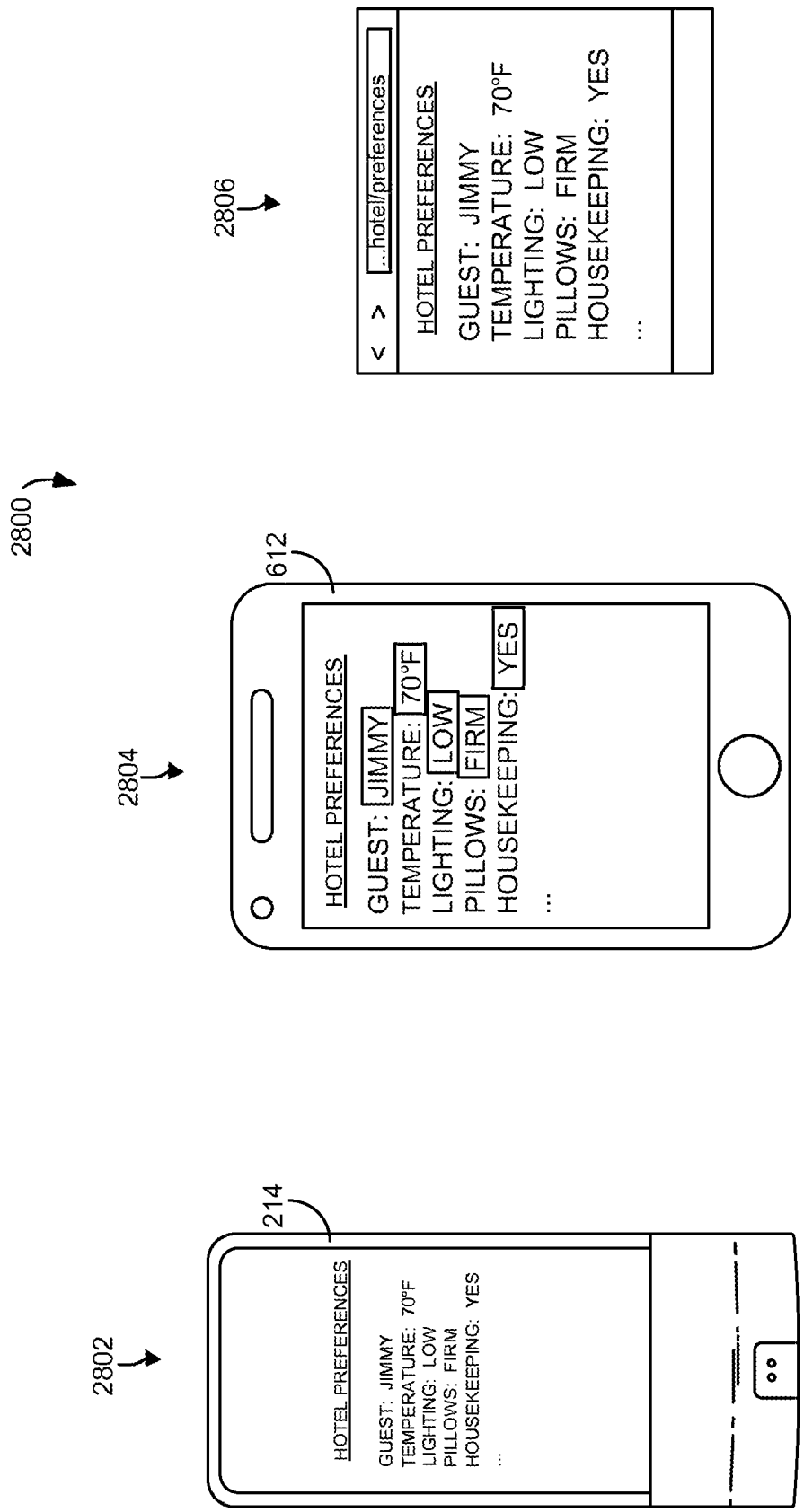
FIG. 28 is a set of drawings of screen displays for selecting room preference of a hotel with the control device of FIG. 7, according to an exemplary embodiment.

Referring now to FIG. 28, drawings of embodiments 2802, 2804, and 2806 are shown illustrating options to set arrangement preferences, according to some embodiments. Some embodiments are useful in hotel arrangements. In other embodiments, a user may select preferences for any arrangements, such as travel (e.g., flights, ground transportation, etc.). Embodiment 2802 shows a preferences interface displayed on control device 214. Available options may include guest name, temperature preference, lighting preference, pillow firmness preference, housekeeping preference, etc. Any options may be available for a user to select, and a user may be able to change her preferences. For example, a user may prefer low lighting in the summer and medium lighting in the winter. Embodiment 2804 shows a preferences interface displayed on user device 612 of a user. Embodiment 2806 shows a preferences interface displayed on a web browser.

Other ways of making arrangements may be available via control device 214. In some embodiments, a user may be able to set preferences through voice command, gesture input, etc. In other embodiments, a user may set preferences through specific applications, the hotel's website, etc. In some embodiments, the control device 214 can send payment and/or credit card information for the transportation. In some embodiments, hotel module 750 may process payment with input device 712 and payment module 758.

Figure 29:
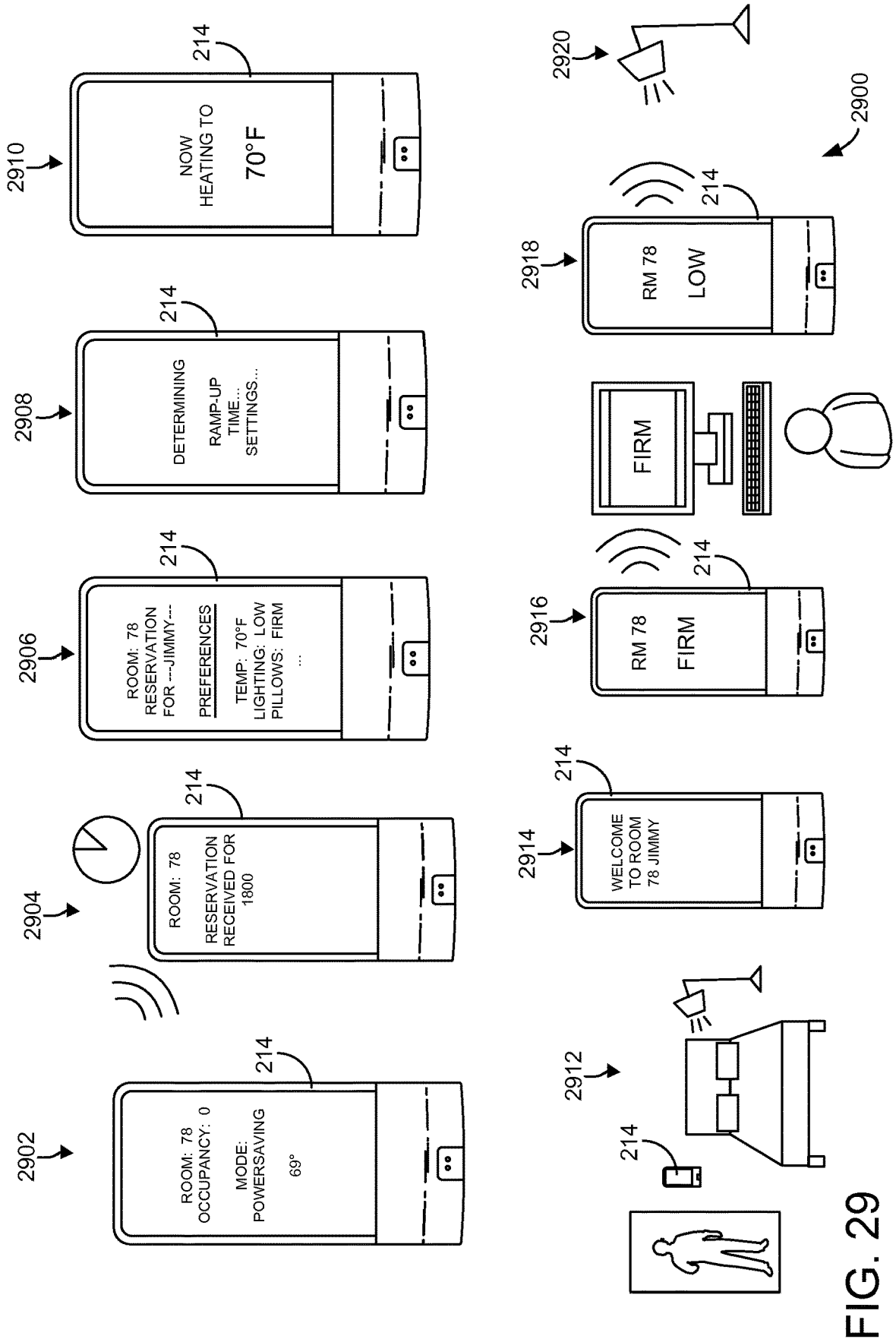
FIG. 29 is a flow diagram of operations for preparing a hotel room for an occupant with the control device of FIG. 7, according to an exemplary embodiment.

Referring now to FIG. 29, a process 2900 is shown for preparing a hotel room for a guest's stay, according to some embodiments. Process 2900 begins with step 2902, in which a control device 214 installed in an unoccupied room is in a power-saving state. Control device 214 may display relevant information for the room, such as the room number, the current occupancy, the mode, and the current conditions. Control device 214 may display more information. In some embodiments, control device 214 may display less information. Control device 214 may be customized to display the information needed for each situation.

Process 2900 continues with step 2904, in which control device 214 receives reservation information for the room at a first time. Control device 214 may display a confirmation message. In some embodiments, control device 214 may send a confirmation message to the front desk, main system, etc. In other embodiments, control device 214 may send a confirmation message to the user. In this exemplary embodiment, the reservation information is received at 1 p.m. local time, and the reservation is for 6 p.m. local time.

Process 2900 continues with step 2906, in which the reservation information and/or preferences are analyzed. The received information may include room number, temperature, humidity, lighting level, pillow firmness, etc. Other information and preferences may be set. The format in which the information is presented to the system, control device 214, etc. may be any format. For example, the system may receive the information as raw data while control device 214 receives data parsed into packets for each category of preference.

Process 2900 continues with step 2908, in which control device 214 may determine the amount of time needed to reach the guest's preferred settings, and when to begin preparing. Control device 214 may determine the approximate time of arrival of a guest and the approximate amount of time needed to reach the environmental setpoints of the guest.

Process 2900 continues with step 2910, in which control device 214 has determined the amount of time needed, the time at which to begin preparing, etc. For example, the preparation for a guest Jimmy arriving at 6 p.m. is shown to begin at 4 p.m. Control device 214 may begin to change the temperature, humidity, etc. of the room. For example, control device 214 may begin to heat the room from 69° F. to Jimmy's preferred 70° F.

Process 2900 continues with step 2912, in which control device 214 informs hospitality services of the guest's preferences. In this exemplary embodiment, Jimmy prefers firm pillows. Control device 214 is shown to inform the front desk of Jimmy's preference. In some embodiments, control device 214 communicates directly with the front desk (e.g., a computer at the front desk). In other embodiments, control device 214 goes through an intermediary (e.g., network 602) to communicate with the front desk. Control device 214 may communicate with the front desk through any means, and may transmit any information. Control device 214 may be compliant with all privacy rules and regulations.

Process 2900 continues with step 2914, in which control device 214 communicates with hotel equipment (e.g., HVAC equipment 738) to achieve the guest's preferences. In this exemplary embodiment, Jimmy prefers low lighting. Control device 214 may communicate with lights (e.g., HVAC Equipment 738) of the room to dim. In some embodiments, control device 214 may communicate directly with lights 2920. In other embodiments, control device 214 may communicate through an intermediary, such as hotel automation system (e.g., building management system 610), network 602, etc. Control device 214 may communicate with hotel equipment (e.g., HVAC Equipment 738) through any communications protocol, and is not limited to those specifically enumerated.

Process 2900 continues with step 2916, in which the guest arrives at the room at a time indicated by his reservation information transmitted to control device 214. In this exemplary embodiment, Jimmy arrives at Room 78 at 6 p.m. local time. Control device 214 is shown to display one or more room settings. For example, control device 214 is shown to be mounted to a wall of the room, and displays the current room temperature—Jimmy's preferred 70° F. Lighting 2920 may be at Jimmy's preferred low setting. In some embodiments, accommodations such as bed inclination level/mattress firmness (e.g., hotel module 750) may be adjusted. In other embodiments, fewer settings may be adjusted.

Process 2900 continues with step 2918, in which the guest is greeted by control device 214. In some embodiments, control device 214 greets the guest purely visually. For example, control device 214 may display text saying "Welcome to Room 12, Aaron." In other embodiments, control device 214 may greet the guest using sound. For example, control device 214 may say "Welcome to Room 78, Jimmy." Control device 214 may greet the user through any means. Control device 214 may be customizable to use a greeting a user has selected, or a greeting specific to the hotel, the room, etc. the user is staying in. Control device 214 may provide options to the user, such as a call for room service, access to the front desk, concierge, etc. In some embodiments, control device 214 performs many of the functions of the concierge desk. In other embodiments, control device 214 connects a user to the concierge desk.

Figure 30:
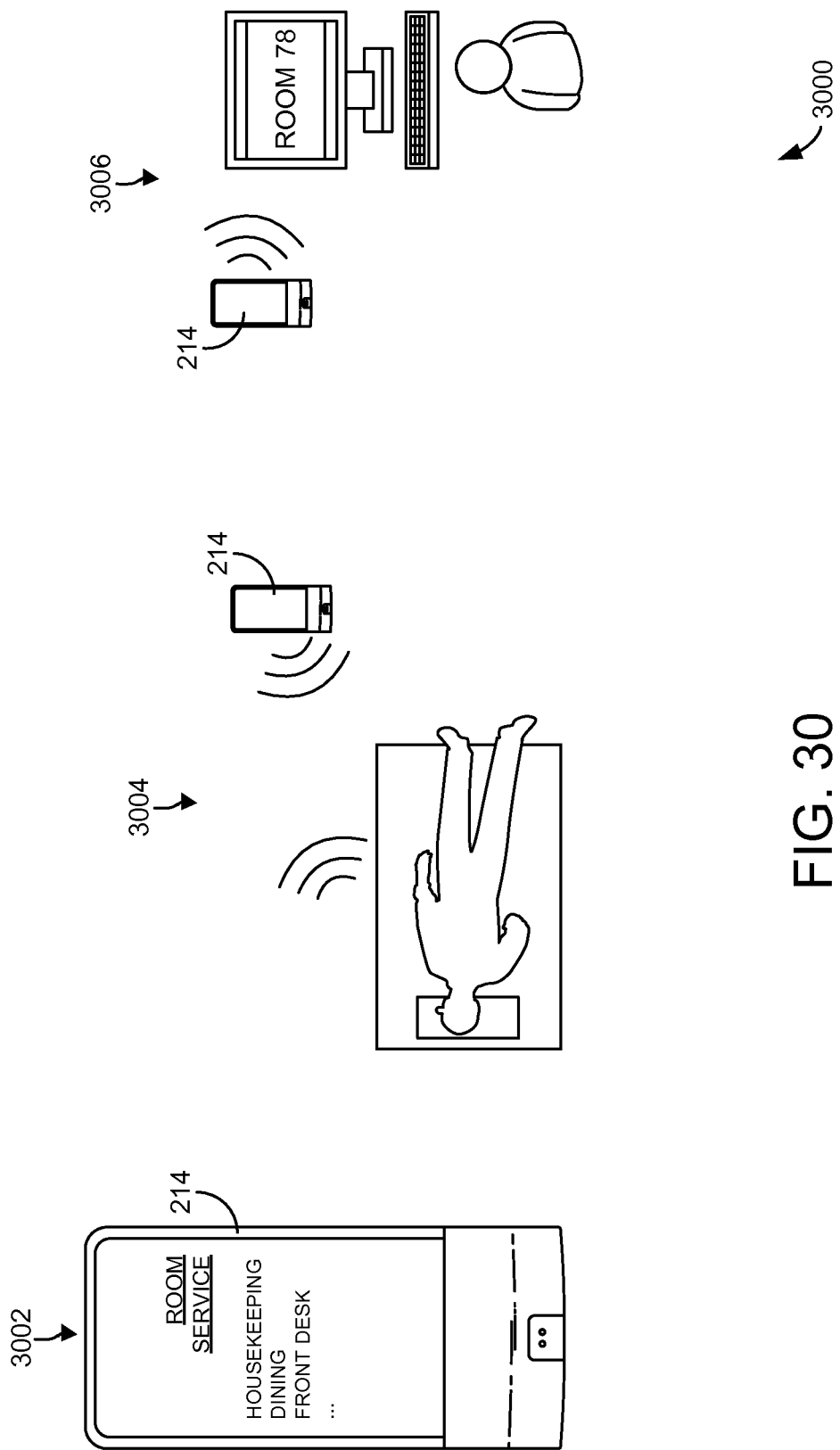
FIG. 30 is a flow diagram of operations for communicating with a front desk with the control device of FIG. 7, according to an exemplary embodiment.

Referring now to FIG. 30, a process 3000 is shown for communicating with a front desk in the event of a service call. In some embodiments, process 3000 is performed by voice command module 744 and/or hotel module 750. In some embodiments, the service call can be made via a voice command and/or through user interface 702. Process 3000 begins with step 3002, in which a set of options available for a user to make a service call regarding is shown on control device 214. In some embodiments, the options are displayed through another medium, such as a mobile device (e.g., user device 612) of a user. Each option displayed may be a link. In some embodiments, the link may take the user to a page with more information about the option. In other embodiments, the link may trigger the service call to be made.

Process 3000 continues with step 3004, in which the user chooses an option and inputs the selection to control device 214. In some embodiments, the user may provide the input as a voice command. In other embodiments, the user may provide the selection as a button press, a tactile input, a gesture, etc via a user interface (e.g., user interface 702). Any input method may be used.

Process 3000 continues with step 3006, in which the selection is transmitted from control device 214 to the appropriate system. In some embodiments, the appropriate system is building management system 610. For example, if the selection made is a request for new towels, housekeeping would be notified. In some embodiments, housekeeping may be notified via building management system 610. In some embodiments, selections made indicate that other departments, such as the front desk, billing, etc. are contacted. In some embodiments, the front desk and billing are connected to building management system 610.

In other embodiments, the request made can be executed automatically by control device 214. For example, if the user requests that the light be turned off when there are multiple lights in the room, control device 214 may use voice command detection (e.g., voice control module 748). Control device 214 may detect which occupancy sensor (e.g., sensors 714) detected the user's voice, or which sensor detected the voice the "loudest." Control device 214 may decide the location of the user using an algorithm and turn off the light nearest that location.

Figure 31:
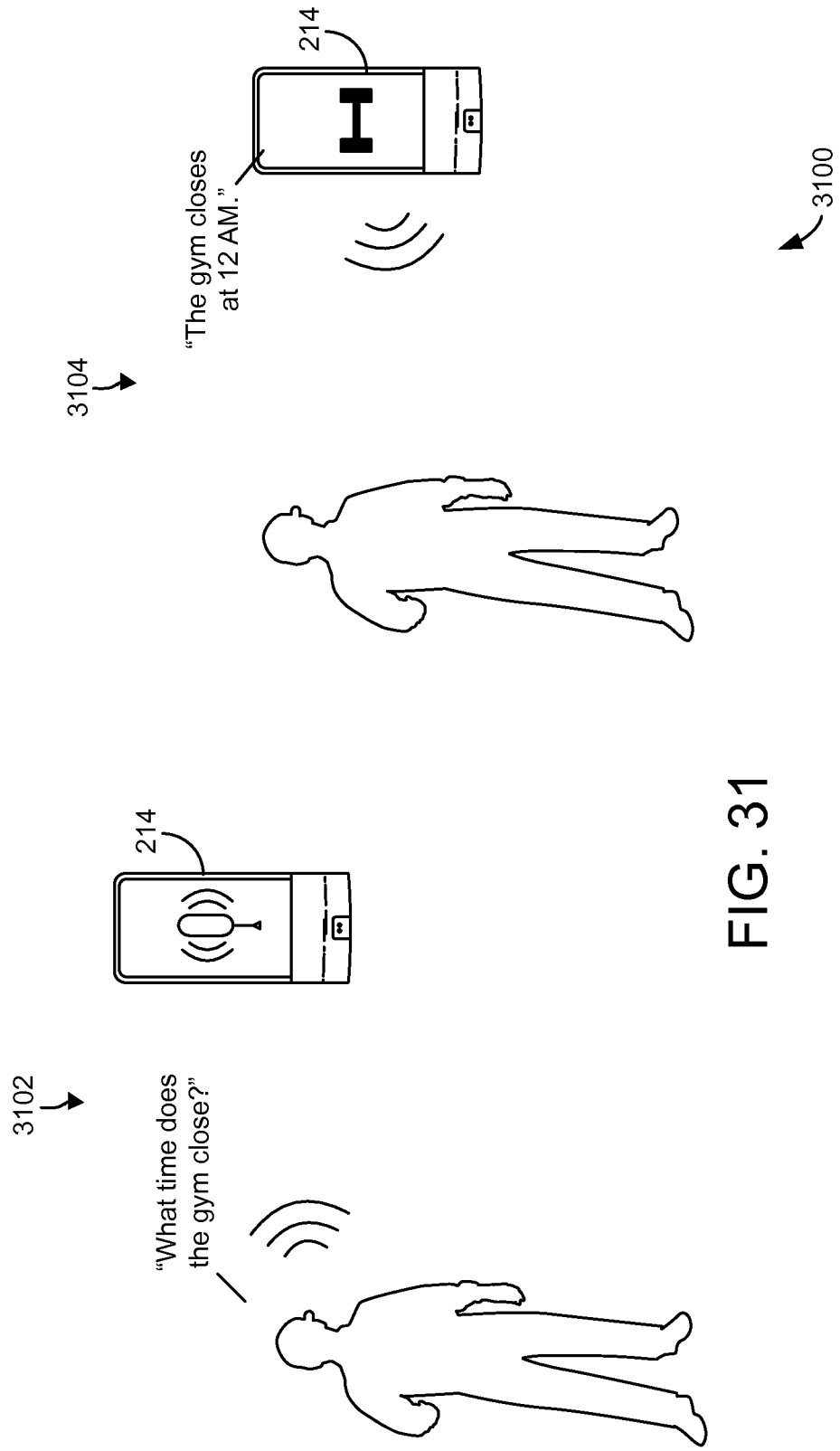
FIG. 31 is a flow diagram of operations for using a concierge feature of the control device of FIG. 7, according to an exemplary embodiment.

Referring now to FIG. 31, a process 3100 is shown for utilizing a concierge feature of control device 214, according to some embodiments. In some embodiments, process 3100 is performed by voice command module 744 and/or hotel module 750. Process 3100 begins with step 3102, in which a user asks control device 214 "What time does the gym close?" Control device 214 may access the requested information. In some embodiments, the information is stored remotely from control device 214. In other embodiments, the information is stored locally on control device 214. In yet other embodiments, control device 214 may search for the information, call the front desk, etc.

The user may request information in any way. In some embodiments, the user may request information through voice commands. In other embodiments, the user may request information through tactile input (e.g., via user interface 702), via a mobile device (e.g., user device 612), etc.

Process 3100 continues with step 3104, in which user control device has obtained the requested information, and transmits the information to the user. In some embodiments, control device 214 provides the information to the user through speakers. For example, control device 214 may say "The gym closes at 12 a.m." In other embodiments, control device 214 may transmit the information through text, images, etc. Control device 214 may present the information to the user via a user interface (e.g., user interface 702), a mobile device (e.g., user device 612), etc.

In some embodiments, control device 214 provides information to the user in the same way the user requested the information. For example, if the user asked a question using a voice command, control device 214 would answer the question via speakers. In other embodiments, control device 214 may provide information to the user according to her preferences. In yet other embodiments, control device 214 would answer the question via a default method, which may be customizable.

Referring now to FIG. 32, a process 3200 is shown for utilizing a concierge feature of control device 214, according to another exemplary embodiment. In some embodiments, process 3200 may be performed by hotel module 750 of control device 214 and/or voice command module 744.

Process 3200 begins with step 3202, in which a user asks control device 214 "What are some local restaurants?" Control device 214 may access the requested information. In some embodiments, the information is stored remotely from control device 214. In other embodiments, the information is stored remotely on building management system 604. In yet other embodiments, control device 214 may search for the information on the Internet (e.g., via network 602), call the front desk, etc.

The user may request information in any way. In some embodiments, the user may request information through voice commands. In other embodiments, the user may request information through tactile input (e.g., via user interface 702), via a mobile device (e.g., user device 612), etc.

Process 3200 continues with step 3204, in which user control device has obtained the requested information, and transmits the information to the user. In some embodiments, control device 214 provides the information to the user through speakers. In other embodiments, control device 214 may transmit the information through text, images, etc. if the answer is too long or too complicated to answer over speakers. For example, if the information requested is an explanation for why the sky is blue, user control device may, as a default, present the information to the user through text. Control device 214 may present the information to the user via user interface 702, user device 612, etc.

Figure 33:
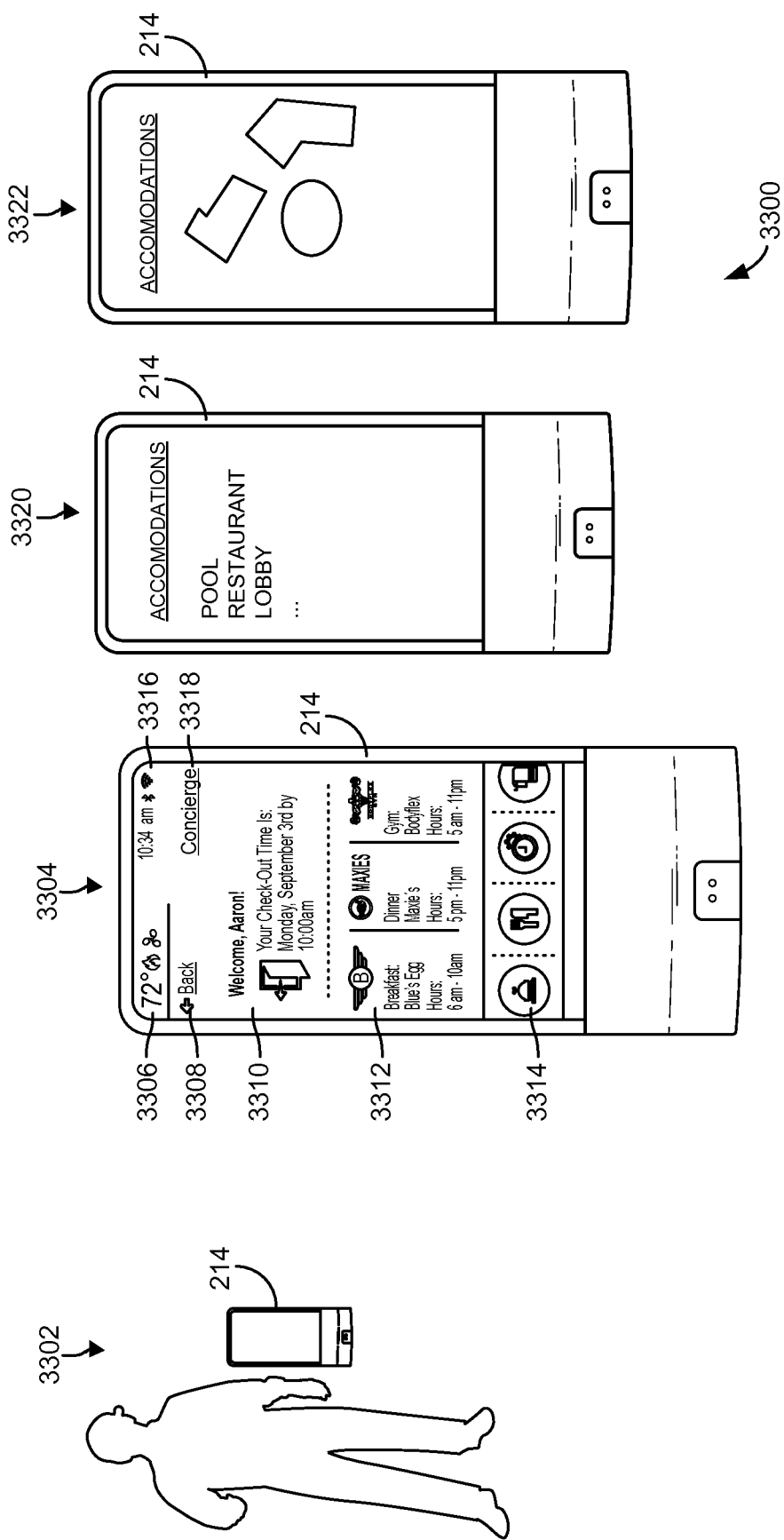
FIG. 33 is a flow diagram of operations for requesting hotel accommodations with the control device of FIG. 7, according to an exemplary embodiment.

Referring now to FIG. 33, a process 3300 for requesting accommodation information from control device 214 is shown, according to some embodiments. Process 3300 begins with step 3302, in which a user requests information from control device 214. In some embodiments, the user may request information via voice command. In other embodiments, the user may request information via a tactile input through user interface 702, gesture input, etc. Control device 214 may access the requested information. In some embodiments, the information is stored remotely from control device 214. In other embodiments, the information is stored locally on control device 214. In yet other embodiments, control device 214 may search for the information, call the front desk, etc.

The user may request information in any way. In some embodiments, the user may request information through voice commands. In other embodiments, the user may request information through tactile input (e.g., user interface 702), via a mobile device (e.g., user device 612), etc.

Process 3300 continues with step 3304, in which user control device has obtained the requested information, and transmits the information to the user. In some embodiments, control device 214 provides the information to the user through speakers. In other embodiments, control device 214 may transmit the information through text, images, etc. In this exemplary embodiment, the information is presented through an interface of a companion application for control device 214. The exemplary embodiment includes a room status indicator 3306. The exemplary embodiment also includes a menu option 3308. The exemplary embodiment includes a message 3310 that greets the user and provides relevant information. For example, if the user is leaving the hotel on that day, message 3310 may include the time of checkout.

The exemplary embodiment includes an information section 3312 that provides relevant information regarding attractions and accommodations. In some embodiments, attractions and accommodations are local to the hotel. In other embodiments, a user may specify the location, distance, price, etc. Control device 214 may store the information. In some embodiments, control device 214 may access the information from an outside site, such as Yelp, Google Reviews, etc.

The exemplary embodiment includes a navigation section 3314 that provides navigation tools. In some embodiments, the tools are buttons represented by icons. In other embodiments, the tools may be text links, check boxes, etc. Navigation section 3314 may be customized to provide relevant options. The exemplary embodiment further includes a system indicator 3316. The exemplary embodiment further includes a page title 3318.

Process 3300 continues with step 3318, in which a screen shows accommodations available at the hotel. A user may input a selection through control device 214 by any means previously described.

Process 3300 continues with step 3320, in which a screen showing a floorplan is displayed on control device 214. In some embodiments, the floorplan may display a user selection, such as a pool. In this exemplary embodiment, the user selected the pool from the screen of control device 214. The location of the pool on the floorplan is shown on the screen. In other embodiments, other information may be shown on control device 214, as described earlier.

Figure 34:
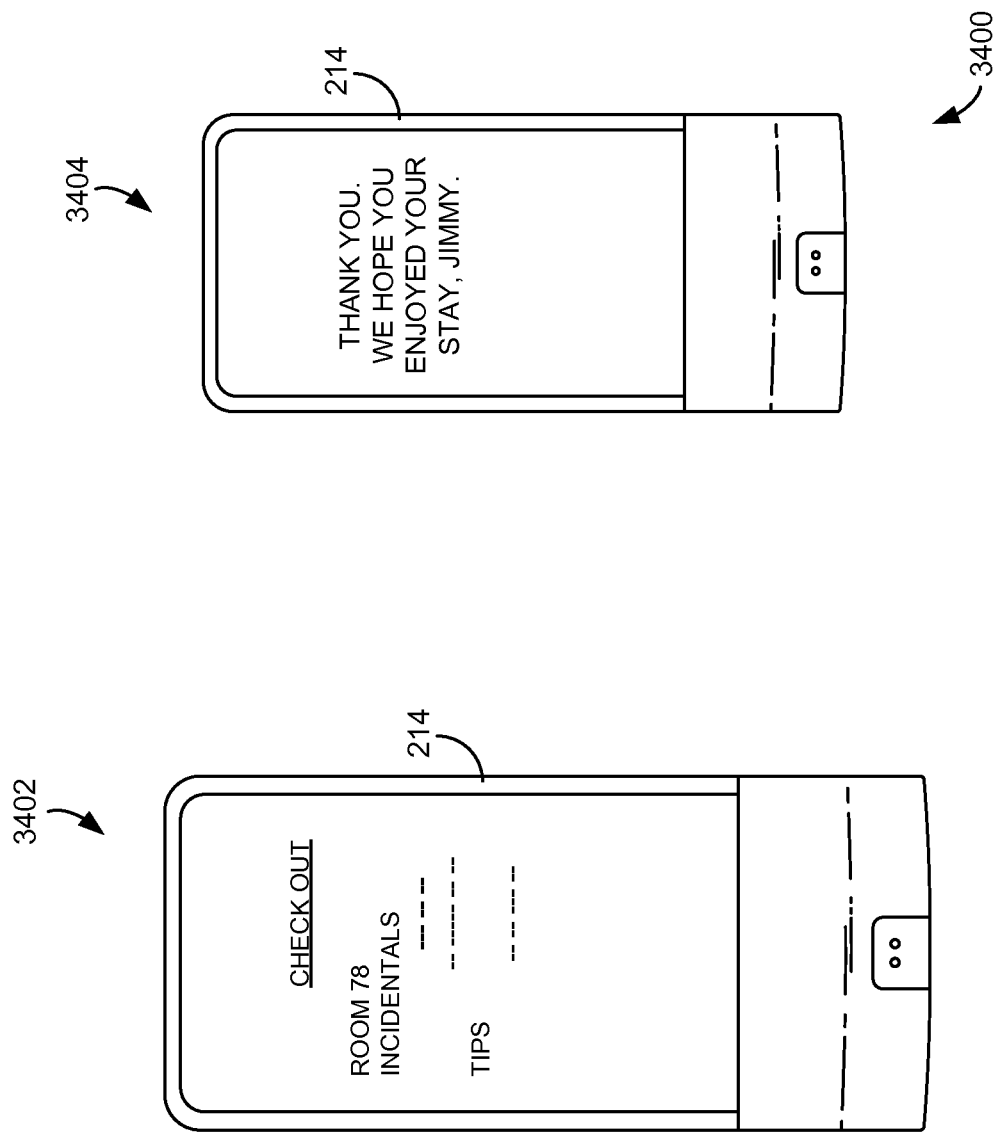
FIG. 34 is a flow diagram of operations for checking out of a hotel room with the control device of FIG. 7, according to an exemplary embodiment.

Referring now to FIG. 34, a process 3400 is shown for assisting a user with checkout without having to go to the front desk. Process 3400 begins with step 3402, in which control device 214 presents a checkout screen to the user. In some embodiments, the screen is presented automatically at checkout time. In other embodiments, the screen may be requested by the user. The screen may include information such as the room number, incidental charges, total charges, tip amounts, etc. Process 3400 may not proceed without confirmation from the user that the information presented is correct, and that she accepts all charges shown.

Process 3400 continues with step 3404, in which control device 214 thanks the user for staying with the hotel with a parting message. In some embodiments, the parting message may be customized to the user's liking. In other embodiments, the parting message is customized for the hotel. The parting message may be delivered in any way. In some embodiments, the parting message is delivered via speakers. In other embodiments, the parting message is delivered as text, images, etc. The parting message may be accompanied by a receipt for the total of the stay. In some embodiments, the receipt may be printed by control device 214. In other embodiments, the receipt may be printed at the front desk and delivered to or picked up by the user. Process 3400 may be executed by control device 214 and/or hotel module 750.

In some embodiments, control device 214 prompts the user to enter payment information and/or swipe a credit and/or debit card via input device 712. This may allow the user to pay for their stay and/or any additional charges without stopping at the front desk. In some embodiments, the control device facilitates transfer of funds from a financial account associated with a user to a financial account associated with the hotel. The financial account may be held with financial institution system 3504 and control device 214 may facilitate the transfer of funds with hotel module 750 and payment module 758. In some embodiments, the user is required to swipe their card with input device 712 at the beginning of their stay and simply confirm the amount and/or leave a tip when their stay expires.

Payment Features

Referring to FIGS. 35-39, in some embodiments, control device 214 may include payment features allowing a user to make payments with a variety of different devices using a variety of different payment protocols. For example, control device 214 may be installed in any location in which a user may make a payment directly, without the involvement of a cashier or other worker, such as in a vehicle (e.g., a taxi), a parking structure, a public transportation station, a hotel, or a retail location (e.g., a store checkout line, a trade show, a convention, etc.).

Figure 35:
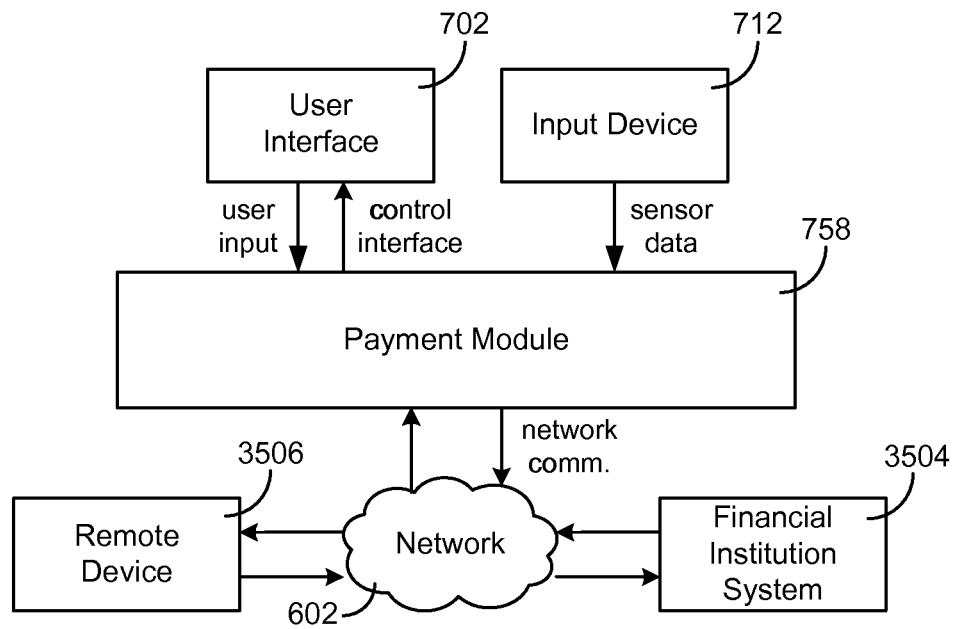
FIG. 35 is a block diagram illustrating the payment module of FIG. 7 in greater detail, according to an exemplary embodiment.

Referring specifically to FIG. 35, payment module 758 is shown in detail. Payment module 758 is shown to interact with user interface 702, input device 712, financial institution system 3504, and network 602. In some embodiments, payment module 758 may interact with a remote device 3506. Remote device 3506 may be any device providing data related to a financial transaction. For example, remote device 3506 may be a cash register or terminal, a taximeter, a mobile device, or any other device capable of providing data related to a financial transaction. The remote device may be directly coupled to control device 214 and directly communicates with control device 214 with a wired or wireless connection. In some embodiments, remote device 3506 is coupled to control device 486 through network 602 and communicates with control device 214 through the network 602.

Figure 36:
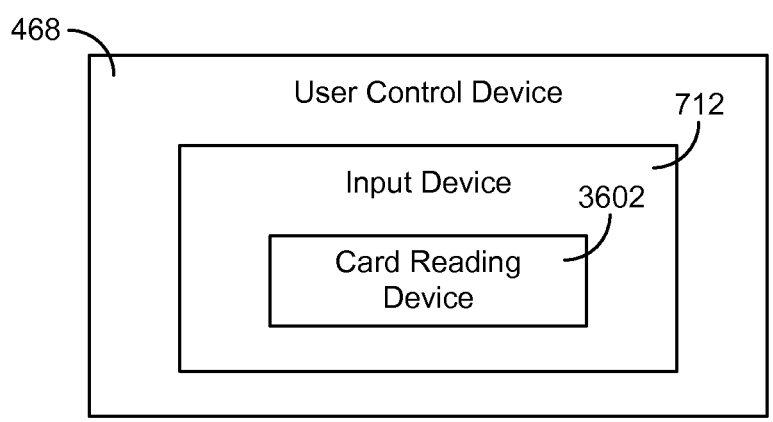
FIG. 36 is a block diagram illustrating the input device of FIG. 7 in greater detail, according to an exemplary embodiment.

Referring now to FIG. 36, a block diagram illustrating an input device 712 of user control device 468 is shown, according to an exemplary embodiment. Input device 712 is shown to include a card reading device 3602. Card reading device 3602 may be any device that is able to receive information from a card (e.g., credit card, debit card, gift card, commuter card, etc.).

Figure 37:
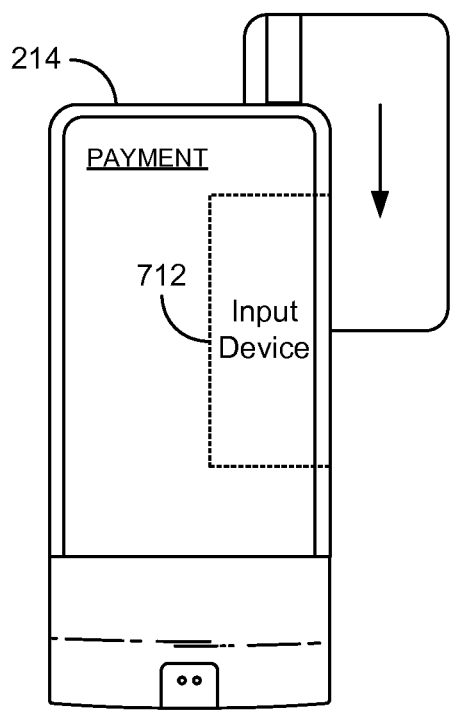
FIG. 37 is a drawing illustrating the control device of FIG. 7 receiving a payment, according to an exemplary embodiment.

Referring to FIG. 37, a diagram of a control device processing payment with an input device, according to an exemplary embodiment. In one embodiment, card reading device 3602 may be a magnetic strip reader that is configured to receive information encoded in a magnetic strip on the card. Information encoded on a magnetic strip of the user's card may be read by the card reading device by inserting the card into the card reading device or by swiping the card through the card reading device. In another embodiment, card reading device 3602 may be a chip reader that is configured to receive information encoded on a microchip on the card. Information encoded on the microchip of the user's card may be read by the card reading device by inserting the card into card reading device 3602. In another embodiment, card reading device 3602 may use another technology to receive information encoded on the user's card. For example, card reading device 3602 may include an infrared scanning mechanism to read information encoded in a bar code on the user's card.

In some embodiments, input device 712 (e.g., card reader, wireless reader, etc.) may be integrated into the user control device. For example, input device 712 may be integrally formed with the display or the base. In other embodiments, input device 712 may be coupled to the display or the base (e.g., as an aftermarket device, etc.). In other embodiments, input device 712 may be separate from control device 214 and may be connected to control device 214 through a wired connection or a wireless connection.

Figure 38:
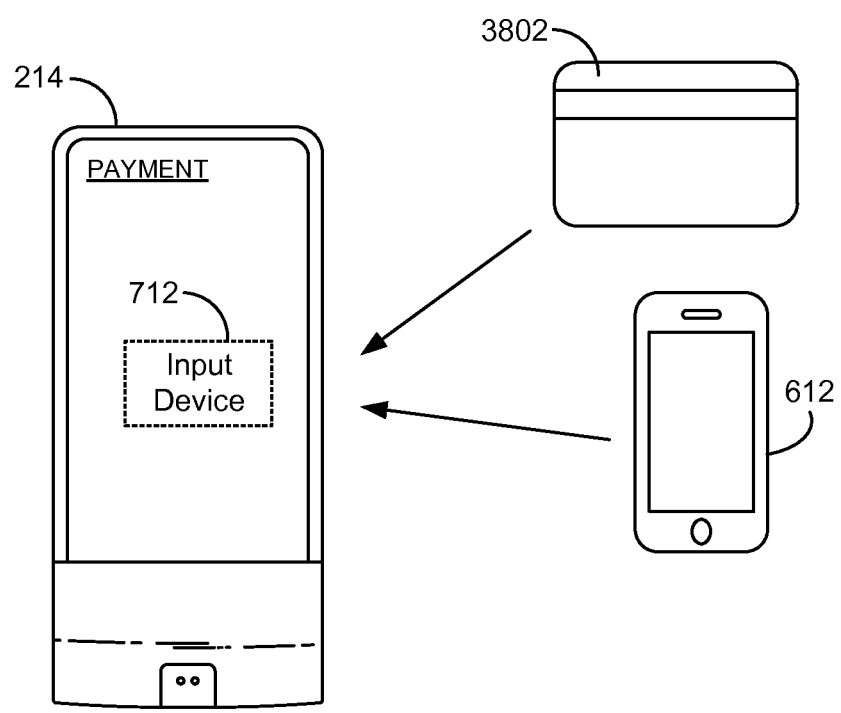
FIG. 38 is another drawing illustrating the control device of FIG. 7 receiving a payment, according to an exemplary embodiment.

Referring now to FIG. 38, a diagram of control device 214 processing a payment with input device 712 is shown, according to an exemplary embodiment. In FIG. 38, control device 214 is shown to include input device 712 that is able to receive information from card 3802 (e.g., credit card, debit card, gift card, commuter card, etc.) or user device 612 without physically interacting with the card or mobile device using a wireless protocol (e.g., ZigBee, Bluetooth, Wi-Fi, NFC, RFID, etc.). In one exemplary embodiment, a user may make a payment by passing a device capable of NFC communication in close proximity to the user control device to make a payment using a mobile payment service (e.g., Apple Pay, Google Wallet, Android Pay, etc.).

Figure 39:
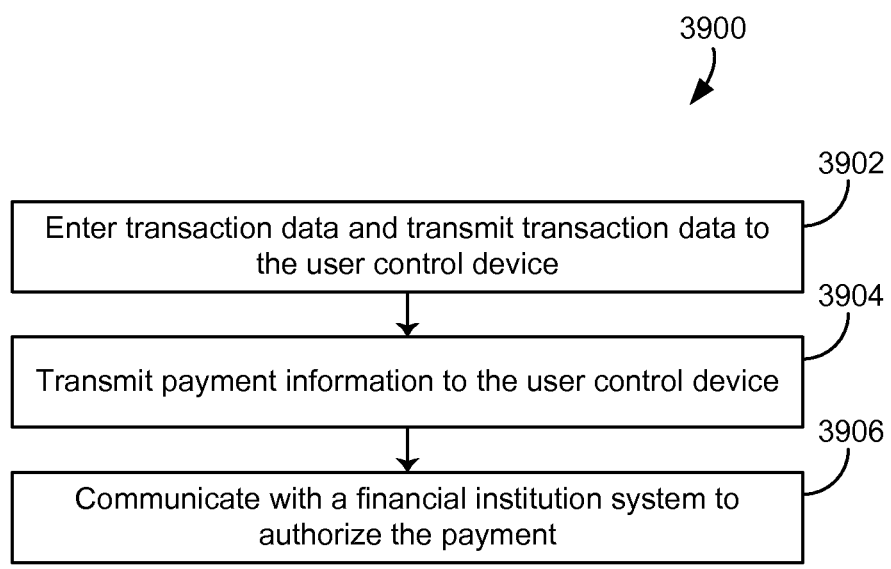
FIG. 39 is a flowchart of operations for processing a transaction with the control device of FIG. 7, according to an exemplary embodiment.

Referring now to FIG. 39, a process 3900 for making a payment with user control device 214 is shown according to some embodiments. In some embodiments, process 3900 is performed by payment module 758 of control device 214. Process 3900 begins with step 3902 in which transaction data is entered and the transaction data is communicated to control device 214. In some embodiments, the transaction data may be entered directly into control device 214 with user interface 702. In some embodiments, the transaction data is received from a remote device. For example, transaction data may be received from a cash register, a payment terminal, a taximeter, a mobile device, etc.

The process continues with step 3904 in which payment data is received by user control device 214. Payment data may be received, for example, by swiping a card through a card reader (e.g., input device 712, card reading device 3602, etc.), inserting a card into a card reader, passing a card under a sensor (e.g., an infrared sensor), or holding a card or mobile device close to control device 214. The payment data may include various information such as authentication data, encryption data, decryption data, etc.

The process continues with step 3906 in which user control device 214 communicates with financial institution system 3504 to authorize the payment. Financial institution system 3504 may, for example, be a credit card company or a banking network. The control device 214 communicates a variety of information to financial institution system 3504 including payment data and transaction data to authorize the payment.

Configuration of Exemplary Embodiments

The construction and arrangement of the systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements may be reversed or otherwise varied and the nature or number of discrete elements or positions may be altered or varied. Accordingly, all such modifications are intended to be included within the scope of the present disclosure. The order or sequence of any process or method steps may be varied or re-sequenced according to alternative embodiments. Other substitutions, modifications, changes, and omissions may be made in the design, operating conditions and arrangement of the exemplary embodiments without departing from the scope of the present disclosure.

The present disclosure contemplates methods, systems and program products on any machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. Combinations of the above are also included within the scope of machine-readable media. Machine-executable instructions include, for example, instructions and data which cause a general purpose computer, special purpose computer, or special purpose processing machines to perform a certain function or group of functions.

Although the figures show a specific order of method steps, the order of the steps may differ from what is depicted. Also two or more steps may be performed concurrently or with partial concurrence. Such variation will depend on the software and hardware systems chosen and on designer choice. All such variations are within the scope of the disclosure. Likewise, software implementations could be accomplished with standard programming techniques with rule based logic and other logic to accomplish the various connection steps, processing steps, comparison steps and decision steps.

What is claimed is:

1. A multi-function thermostat for a building, the thermostat comprising:
a sensor configured to measure an environmental condition of a building space;
a communications interface configured to:
provide at least one signal to HVAC equipment based on a measurement from the sensor to control the environmental condition of the building space;
communicate with an emergency server; and
receive occupant health data from a health sensor configured to monitor an occupant, wherein the occupant health data comprises a health value indicating a measured biological condition of the occupant; and
a processing circuit configured to:
calculate a health metric associated with the occupant based on the health value, wherein the health metric is a function of the health value and indicates health of the occupant; and
cause the communications interface to send a medical distress message to the emergency server when the health metric associated with the occupant indicates a medical emergency of the occupant.

2. The thermostat of claim 1, wherein the communications interface is configured to cause the thermostat to generate an alert when the health metric associated with the occupant indicates the medical emergency.

3. The thermostat of claim 1, wherein the communications interface is configured to communicate with occupancy sensors;
wherein the processing circuit is configured to identify the occupant based on occupancy data received from the occupancy sensors.

4. The thermostat of claim 1, wherein the health sensor is a smart wrist band and the health value comprises at least one of a heart rate or a body temperature.

5. The thermostat of claim 1, wherein the processing circuit is configured to determine the health metric associated with the occupant by:
comparing the health value indicating the measured biological condition of the occupant to a stored threshold value, wherein the health value comprises at least one of a body temperature of the occupant, a heat rate of the occupant, or an insulin level of the occupant; and calculating the health metric based on a result of the comparing.

6. The thermostat of claim 1, wherein:
the health value comprises a measured heart rate of the occupant; and
the processing circuit is configured to determine the health metric associated with the occupant by monitoring the measured heart rate for heart arrhythmia.

7. The thermostat of claim 1, wherein:
the emergency server comprises at least one of an emergency response operator server, a nurses' station computing system, and a hospital server; and
the medical distress message comprises a description of the medical emergency associated with the occupant.

8. The thermostat of claim 1, wherein the processing circuit is configured to push health messages to a user device, wherein the health messages comprise at least one of the medical distress message, a reminder to take medication, and a reminder for an appointment.

9. The thermostat of claim 1,
wherein the medical distress message of the medical emergency further comprises an indication of a location of the occupant in the building.

10. A method for operating a multi-function thermostat for a building, the thermostat comprising a sensor configured to measure an environmental condition of a building space and a communications interface configured to provide operating parameters to HVAC equipment based on a measurement from the sensor to control the environmental condition of the building space, the method comprising:
receiving occupant health data comprising a health value indicating a measured biological condition of an occupant from a health sensor via the communications interface of the thermostat;
calculating a health metric associated with the occupant based on the health value, wherein the health metric is a function of the health value and indicates health of the occupant; and
causing the communications interface to send a medical distress message to an emergency server when the health metric associated with the occupant indicates a medical emergency of the occupant.

11. The method of claim 10, further comprising causing the thermostat to generate an alert when the health metric associated with the occupant indicates the medical emergency.

12. The method of claim 10, further comprising:
receiving occupancy data from an occupancy sensor via the communications interface; and
identifying the occupant based on occupancy data received from the occupancy sensor.

13. The method of claim 10, wherein the health sensor comprises a smart wrist band and the health value comprises at least one of a heart rate and a body temperature.

14. The method of claim 10, wherein:
the health value comprises a heart rate; and
determining the health metric comprises monitoring the heart rate for heart arrhythmia.

15. The method of claim 10, wherein the emergency server comprises at least one of an emergency response operator server, a nurses' station computing system, and a hospital server, and the medical distress message comprises a description of the medical emergency associated with the occupant.

16. The method of claim 10, wherein the medical distress message of the medical emergency further comprises an indication of a location of the occupant in the building.

17. A multi-function thermostat for a building, the thermostat comprising:
one or more sensors configured to measure an environmental condition of a building space;
a communications interface configured to:
provide at least one signal to HVAC equipment based on a measurement from the a sensor to control the environmental condition of the building space;
communicate with a second thermostat for the building, the second thermostat located in a different location within the building than the thermostat; and
receive occupant health data from a health sensor configured to monitor an occupant within the building space, wherein the health data comprises a health value indicating a measured biological condition of the occupant; and
a processing circuit configured to:
cause the communications interface to send a medical distress message to the second thermostat when the health value associated with the occupant indicates a medical emergency of the occupant.

18. The thermostat of claim 17, wherein the health sensor comprises a wearable health sensor, wherein the wearable health sensor comprises a smart wrist band, and wherein the health value comprises at least one of a heart rate and a body temperature.

19. The thermostat of claim 17, wherein the processing circuit is configured to determine a health metric by:
monitoring the health data for heart arrhythmia when the health value comprises a heart rate; and
monitoring the heart rate for tachycardia or bradycardia when the health value comprises the heart rate.

20. The thermostat of claim 17, wherein the health sensor comprises a wearable health sensor, wherein the wearable health sensor is an insulin pump, and wherein the health value comprises an insulin level of the occupant;
wherein the processing circuit is configured to:
compare the measured insulin level to a stored threshold value; and
calculate a health metric based on a result of the comparing.

* * * * *